(12) United States Patent
Lin et al.

(10) Patent No.: US 9,096,605 B2
(45) Date of Patent: Aug. 4, 2015

(54) PYRAZOLOPYRIMIDINE DERIVATIVES AS PI3 KINASE INHIBITORS

(75) Inventors: Hong Lin, Collegeville, PA (US); Juan Ignacio Luengo, Collegeville, PA (US); Michael Lee Moore, Collegeville, PA (US); Junya Qu, Collegeville, PA (US); Ralph A. Rivero, Collegeville, PA (US); Rosanna Tedesco, Collegeville, PA (US); Hongyi Yu, Collegeville, PA (US)

(73) Assignee: GlaxoSmithKline LLC, Wilmington, DE (US)

( * ) Notice: Subject to any disclaimer, the term of this patent is extended or adjusted under 35 U.S.C. 154(b) by 0 days.

(21) Appl. No.: 14/233,896

(22) PCT Filed: Jun. 29, 2012

(86) PCT No.: PCT/US2012/044782
§ 371 (c)(1),
(2), (4) Date: Jan. 21, 2014

(87) PCT Pub. No.: WO2013/028263
PCT Pub. Date: Feb. 28, 2013

(65) Prior Publication Data
US 2014/0187545 A1    Jul. 3, 2014

Related U.S. Application Data

(60) Provisional application No. 61/526,718, filed on Aug. 24, 2011.

(51) Int. Cl.
*C07D 413/04*    (2006.01)
*C07D 487/04*    (2006.01)

(52) U.S. Cl.
CPC ............ *C07D 487/04* (2013.01); *C07D 413/04* (2013.01)

(58) Field of Classification Search
CPC ..................................................... C07D 413/04
USPC ........................................ 514/233.2; 544/117
See application file for complete search history.

(56) References Cited

U.S. PATENT DOCUMENTS

| 7,528,138 B2 * | 5/2009 | Knegtel et al. ............. 514/259.3 |
| 2009/0124609 A1 | 5/2009 | Albrecht et al. |
| 2010/0311729 A1 | 12/2010 | Capraro et al. |

* cited by examiner

*Primary Examiner* — Rebecca Anderson
(74) *Attorney, Agent, or Firm* — J. Scott Young

(57) ABSTRACT

PI3Kβ selective compounds having the structure

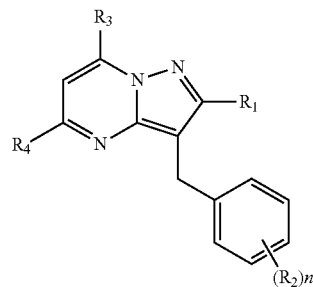

2 Claims, No Drawings

PYRAZOLOPYRIMIDINE DERIVATIVES AS PI3 KINASE INHIBITORS

CROSS-REFERENCE TO RELATED APPLICATIONS

This application is filed pursuant to 35 USC 371 as a United States National Phase Application of International Patent Application Serial No. PCT/US2012/044782 filed on Jun. 29, 2012, which claims priority from 61/526,718 filed on Aug. 24, 2011 in the United States.

FIELD OF THE INVENTION

This invention relates to the use of pyrazolopyrimidine derivatives for the modulation, notably the inhibition of the activity or function of the phosphoinositide 3' OH kinase family (hereinafter PI3 kinases), suitably, PI3Kα, PI3Kδ, PI3Kβ, and/or PI3Kγ. Suitably, the present invention relates to the use of pyrazolopyrimidines in the treatment of one or more disease states selected from: autoimmune disorders, inflammatory diseases, cardiovascular diseases, neurodegenerative diseases, allergy, asthma, pancreatitis, multiorgan failure, kidney diseases, platelet aggregation, cancer, sperm motility, transplantation rejection, graft rejection and lung injuries. More suitably, the present invention relates to PI3Kβ selective pyrazolopyrimidine inhibitors for treating cancer.

BACKGROUND OF THE INVENTION

The phosphoinositide 3-kinase (PI3K) pathway is among the most commonly activated in human cancer and the importance in carcinogenesis is well established. (Samuels Y and Ericson K. Oncogenic PI3K and its role in cancer. *Current Opinion in Oncology*, 2006; 18:77-82) Initiation of signaling begins with the phosphorylation of phosphatidylinositol-4,5-bisphosphate (PIP2) to produce phosphatidylinositol-3,4,5-P3 (PIP3). PIP3 is a critical second messenger which recruits proteins that contain pleckstrin homology domains to the cell membrane where they are activated. The most studied of these proteins is AKT which promotes cell survival, growth and proliferation.

The PI3K family consists of 15 proteins that share sequence homology, particularly within their kinase domains, but have distinct substrate specificities and modes of regulation. (Vivanco I and Sawyers C L. The phosphatidylinositol 3-kinase-AKT pathway in human cancer. *Nature Reviews Cancer*, 2002; 2:489-501) Class I PI3Ks are heterodimers consisting of a p110 catalytic subunit complexed to one of several regulatory subunits collectively referred to as p85 and have been the most extensively studied in the context of tumorgenesis. The class 1A PI3K catalytic subunits comprise the p110α, p110β, and p110δ isoforms, which associate with one of five different regulatory subunits encoded by three separate genes. A single class 1B PI3K catalytic isoform p110γ interacts with one of two associated regulatory subunits. (Crabbe T, Welham M J, Ward S G, The PI3k inhibitor arsenal: choose your weapon *Trends in Biochem Sci*, 2007; 32:450-456) Class 1 PI3Ks are primarily responsible for phosphorylating the critical PIP2 signaling molecule.

The link between the PI3K pathway and cancer was confirmed by a study which identified somatic mutations in the PIK3CA gene encoding the p110α protein. Subsequently, mutations in PIK3CA have been identified in numerous cancers including colorectal, breast, glioblastomas ovarian and lung. In contrast to PIK3CA, no somatic mutations in the β isoform have been identified. However, in overexpression studies the PI3Kβ isoform has been implicated as necessary for transformation induced by the loss or inactivation of the PTEN tumor suppressor both in vitro and in vivo. (Torbett N E, Luna A, Knight Z A, et al., A chemical screen in diverse breast cancer cell lines reveals genetic enhancers and suppressors of sensitivity to PI3K isotype-selective inhibition. *Biochem J* 2008; 415:97-110; Zhao J J, Liu Z, Wang L, Shin E, Loda M F, Roberts T M, The oncogenic properties of mutant p110a and p110b phosphatidylinositol 3-kinases in human mammary epithelial cells. *Proc Natl Acad Sci USA* 2005; 102:18443-8) Consistent with this finding, overexpression of the PIK3CB gene has been identified in some bladder, colon, glioblastomas and leukemias and siRNA mediated knockdown of p110β in glioblastoma cell lines results in suppression of tumor growth in vitro and in vivo. (Pu P, Kang C, Zhang Z, et al., Downregulation of PIK3CB by siRNA suppresses malignant glioma cell growth in vitro and in vivo. *Technolo Cancer Res Treat* 2006; 5:271-280) More recent data using shRNA demonstrated that downregulation of p110β and not p110α resulted in PI3K pathway inactivation and subsequent inactivation of tumor cell growth in PTEN deficient cancers cells both in vitro and in vivo. (Wee S, Wiederschain, Maira S-M, Loo A, Miller C, et al., PTEN-deficient cancers depend on PIK3CB. *Proc Natl Acad Sci* 2008; 105:13057-13062) Consistent with a role of PIK3CB signaling in PTEN null tumors, p110β was reported to be essential to the transformed phenotype in a PTEN-null prostate cancer model. (Jia S, Liu Z, Zhang S, Liu P, Zhang L, et al., Essential roles of PI(3)K-p110b in cell growth, metabolism and tumorgenesis. *Nature* 2008; 10:1038) Further, it has been reported that fibrogenesis, including systemic sclerosis (SSc), arthritis, nephropahty, liver cirrhosis, and some cancers, are related to PTEN deficiency and corresponding PI3K-Akt overexpression. (Parapuram, S. K., et al., Loss of PTEN expression by dermal fibroblasts causes skin fibrosis. J. of Investigative Dermatology, advance online publication 9 Jun. 2011; doi: 10.1038/jid.2011.156) Taken together, these findings indicate PI3K p110β as a promising target for cancer and other syndromes related to PTEN loss (Hollander, M. Christine; Blumenthal, Gideon M.; Dennis, Phillip P.; PTEN loss in the continuum of common cancers, rare syndromes and mouse models. *Nature Reviews/Cancer* 2011; 11: 289-301).

SUMMARY OF THE INVENTION

This invention relates to compounds of formula (I):

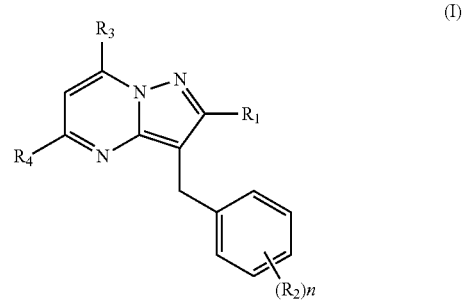

wherein
R1 is H, $C_{1-6}$alkyl, —OH, $C_{1-6}$alkoxy, $NH_2$, or $CF_3$;
each R2 is H, $C_{1-6}$alkyl, halo, $CF_3$, or
two R2's combine with the phenyl ring to which they are attached to form a bicyclic aryl or bicyclic heteroaryl;

R3 is H, —CN, OH, NH$_2$, halo, C$_{1-6}$alkyl, C$_{1-6}$alkoxy, —C(O)Ra, —NH(O)Ra, =O, or a 5 or 6 membered heterocycle containing 1-3 heteroatoms selected from N and O;

R4 is a 5 or 6 membered heterocycle or 5 or 6 membered heteroaryl containing 1-3 heteroatoms selected from N and O, optionally substituted with C$_{1-6}$alkyl or =O;

Ra is OH, NH$_2$, or C$_{1-6}$alkyl; and n is 0-2, or a pharmaceutically acceptable salt thereof.

In another aspect of the present invention, there is provided a pharmaceutical composition comprising a compound of formula (I) (including any particular sub-generic formula described herein) or a pharmaceutically acceptable salt thereof. In one embodiment, the pharmaceutical composition further comprises one or more of pharmaceutically acceptable carriers, diluents or excipients.

In another aspect of the present invention, there is provided a method of treating a susceptible neoplasm in a mammal in need thereof, comprising administering to the mammal a therapeutically effective amount of a compound of formula (I) (including any particular sub-generic formula described herein) or a pharmaceutically acceptable salt thereof. Susceptible neoplasms include e.g., Barret's adenocarcinoma; biliary tract carcinomas; breast cancer; cervical cancer; cholangiocarcinoma; central nervous system tumors including primary CNS tumors such as glioblastomas, astrocytomas (e.g., glioblastoma multiforme) and ependymomas, and secondary CNS tumors (i.e., metastases to the central nervous system of tumors originating outside of the central nervous system); colorectal cancer including large intestinal colon carcinoma; gastric cancer; carcinoma of the head and neck including squamous cell carcinoma of the head and neck; hematologic cancers including leukemias and lymphomas such as acute lymphoblastic leukemia, acute myelogenous leukemia (AML), myelodysplastic syndromes, chronic myelogenous leukemia, Hodgkin's lymphoma, non-Hodgkin's lymphoma, megakaryoblastic leukemia, multiple myeloma and erythroleukemia; hepatocellular carcinoma; lung cancer including small cell lung cancer and non-small cell lung cancer; ovarian cancer; endometrial cancer; pancreatic cancer; pituitary adenoma; prostate cancer; renal cancer; sarcoma; skin cancers including melanomas; and thyroid cancers.

In another aspect of the present invention, there is provided a method of treating fibrosis in a mammal in need thereof, comprising administering to the mammal a therapeutically effective amount of a compound of formula (I) (including any particular sub-generic formula described herein) or a pharmaceutically acceptable salt thereof. Fibrosis includes, alternatively or collectively, systemic sclerosis (SSc), arthritis, nephropahty, and liver cirrhosis.

In another aspect of the present invention, there is provided a compound of formula (I), (including any particular sub-generic formula described herein) or a pharmaceutically acceptable salt thereof for use in therapy.

In another aspect, there is provided a compound of formula (I) (including any particular sub-generic formula described herein) or a pharmaceutically acceptable salt thereof for use in the treatment of a susceptible neoplasm.

In a another aspect of the present invention, there is provided the use of a compound of formula (I) (including any particular sub-generic formula described herein) or a pharmaceutically acceptable salt thereof, in the preparation of a medicament for use in the treatment of a susceptible neoplasm in a mammal (e.g., human) in need thereof.

DETAILED DESCRIPTION OF THE INVENTION

This invention relates to compounds of formula (I):

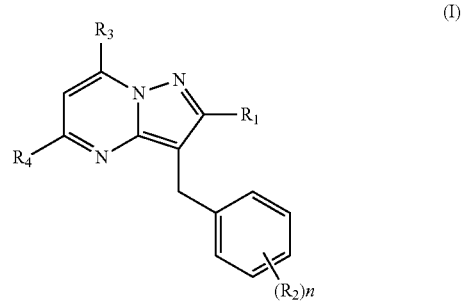

(I)

wherein

R1 is H, C$_{1-6}$alkyl, —OH, C$_{1-6}$alkoxy, NH$_2$, or CF$_3$;

each R2 is H, C$_{1-6}$alkyl, halo, CF$_3$, or two R2's combine with the phenyl ring to which they are attached to form a bicyclic aryl or bicyclic heteroaryl;

R3 is H, —CN, OH, NH$_2$, halo, C$_{1-6}$alkyl, C$_{1-6}$alkoxy, —C(O)Ra, —NH(O)Ra, =O, or a 5 or 6 membered heterocycle containing 1-3 heteroatoms selected from N and O;

R4 is a 5 or 6 membered heterocycle or 5 or 6 membered heteroaryl containing 1-3 heteroatoms selected from N and O, optionally substituted with C$_{1-6}$alkyl or =O;

Ra is OH, NH$_2$, or C$_{1-6}$alkyl; and n is 0-2, or a pharmaceutically acceptable salt thereof.

In a particular embodiment of the invention, there are provided compounds of formula (Ia)

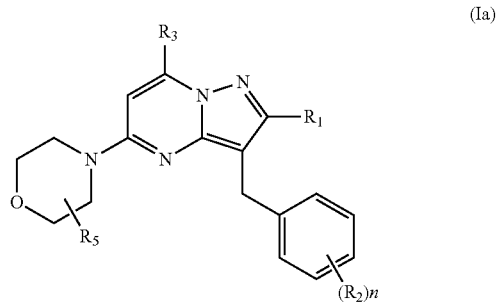

(Ia)

wherein

R1 is H, C$_{1-6}$alkyl, —OH, C$_{1-6}$alkoxy, NH$_2$, or CF$_3$;

each R2 is H, C$_{1-6}$alkyl, halo, CF$_3$, or two R2's combine with the phenyl ring to which they are attached to form napthyl;

R3 is H, —CN, OH, NH$_2$, halo, C$_{1-6}$alkyl, C$_{1-6}$alkoxy, —C(O)Ra, —NH(O)Ra, =O, or a 5 or 6 membered heterocycle containing 1-3 heteroatoms selected from N and O;

R5 is C$_{1-6}$alkyl or =O;

Ra is OH, NH$_2$, or C$_{1-6}$alkyl; and n is 0-2, or a pharmaceutically acceptable salt thereof.

According to one embodiment, there are provided compounds of formula (I) as defined above wherein n=2, R2's are selected independently from $C_{1-6}$alkyl, halo, and $CF_3$, and the R2's are located ortho and meta on the phenyl group to which they are attached.

According to one embodiment, there are provided compounds of formula (Ia) as defined above wherein n=2, R2's are selected independently from $C_{1-6}$alkyl, halo, and $CF_3$, and the R2's are located ortho and meta on the phenyl group to which they are attached.

In a particular embodiment of the invention, there are provided compounds of formula (I) wherein R1 is H, $C_{1-6}$alkyl, —OH, $C_{1-6}$alkoxy, $NH_2$, or $CF_3$; each R2 is H, $C_{1-6}$alkyl, halo, $CF_3$, or two R2's combine with the phenyl ring to which they are attached to form napthyl; R3 is H, —CN, OH, $NH_2$, halo, $C_{1-6}$alkyl, $C_{1-6}$alkoxy, —C(O)Ra, —NH(O)Ra, =O, or a 5 or 6 membered heterocycle containing 1-3 heteroatoms selected from N and O; R4 is a 5 or 6 membered heterocycle or 5 or 6 membered heteroaryl containing 1-3 heteroatoms selected from N and O, optionally substituted with $C_{1-6}$alkyl or =O; Ra is OH, $NH_2$, or $C_{1-6}$alkyl; and n is 0-2, or a pharmaceutically acceptable salt thereof.

In a particular embodiment of the invention, there are provided compounds of formula (I) wherein R1 is H, $C_{1-6}$alkyl, —OH, $C_{1-6}$alkoxy, $NH_2$, or $CF_3$; each R2 is H, $C_{1-6}$alkyl, halo, or $CF_3$; R3 is H, —CN, OH, $NH_2$, halo, $C_{1-6}$alkyl, $C_{1-6}$alkoxy, —C(O)Ra, —NH(O)Ra, =O, or a 5 or 6 membered heterocycle containing 1-3 heteroatoms selected from N and O; R4 is a 5 or 6 membered heterocycle or 5 or 6 membered heteroaryl containing 1-3 heteroatoms selected from N and O, optionally substituted with $C_{1-6}$alkyl or =O; Ra is OH, $NH_2$, or $C_{1-6}$alkyl; and n is 0-2, or a pharmaceutically acceptable salt thereof.

This invention encompasses the following compounds:
2-methyl-3-(2-methyl-3-(trifluoromethyl)benzyl)-5-morpholinopyrazolo[1,5-a]pyrimidin-7-ol,
2-methyl-3-(2-methyl-3-(trifluoromethyl)benzyl)-5-(2-methylmorpholino)pyrazolo[1,5-a]pyrimidin-7-ol,
4-(7-hydroxy-2-methyl-3-(2-methyl-3-(trifluoromethyl)benzyl)pyrazolo[1,5-a]pyrimidin-5-yl)morpholin-3-one,
2-methyl-3-(2-methyl-3-(trifluoromethyl)benzyl)-5-(tetrahydro-2H-pyran-4-yl)pyrazolo[1,5-a]pyrimidin-7-ol,
2-methyl-3-(2-methyl-3-(trifluoromethyl)benzyl)-5-(tetrahydro-2H-pyran-4-yl)pyrazolo[1,5-a]pyrimidine,
2-methyl-3-(2-methyl-3-(trifluoromethyl)benzyl)-5-(pyridin-4-yl)pyrazolo[1,5-a]pyrimidin-7-amine,
3-(2,3-dichlorobenzyl)-5-morpholino-2-(trifluoromethyl)pyrazolo[1,5-a]pyrimidin-7-ol,
3-(2,3-dichlorobenzyl)-5-(2-methylmorpholino)-2-(trifluoromethyl)pyrazolo[1,5-a]pyrimidin-7-ol,
3-(2,3-dichlorobenzyl)-5-(tetrahydro-2H-pyran-4-yl)-2-(trifluoromethyl)pyrazolo[1,5-a]pyrimidin-7-ol,
4-(7-chloro-3-(2-methyl-3-(trifluoromethyl)benzyl)pyrazolo[1,5-a]pyrimidin-5-yl)morpholine,
3-(2-methyl-3-(trifluoromethyl)benzyl)-5-morpholinopyrazolo[1,5-a]pyrimidin-7-ol,
4-(7-methoxy-3-(2-methyl-3-(trifluoromethyl)benzyl)pyrazolo[1,5-a]pyrimidin-5-yl)morpholine,
3-(2-methyl-3-(trifluoromethyl)benzyl)-5-(pyridin-4-yl)pyrazolo[1,5-a]pyrimidin-7-ol,
3-(2,3-dimethylbenzyl)-5-(pyridin-4-yl)pyrazolo[1,5-a]pyrimidin-7-ol,
3-(2,3-dichlorobenzyl)-2-ethyl-5-(tetrahydro-2H-pyran-4-yl)pyrazolo[1,5-a]pyrimidin-7-ol,
1-(2-methyl-3-(2-methyl-3-(trifluoromethyl)benzyl)-5-morpholinopyrazolo[1,5-a]pyrimidin-7-yl)urea,
2-methyl-3-(2-methyl-3-(trifluoromethyl)benzyl)-5-morpholinopyrazolo[1,5-a]pyrimidin-7-amine,
N-(2-methyl-3-(2-methyl-3-(trifluoromethyl)benzyl)-5-morpholinopyrazolo[1,5-a]pyrimidin-7-yl)acetamide,
3-(2-methyl-3-(trifluoromethyl)benzyl)-5-(tetrahydro-2H-pyran-4-yl)pyrazolo[1,5-a]pyrimidine-2,7-diol,
3-(2,3-dichlorobenzyl)-5-morpholinopyrazolo[1,5-a]pyrimidin-7-amine,
3-(2-chlorobenzyl)-2-hydroxy-5-(pyridin-4-yl)pyrazolo[1,5-a]pyrimidin-7(4H)-one,
2-methyl-5-morpholino-3-(naphthalen-1-ylmethyl)pyrazolo[1,5-a]pyrimidin-7-ol,
2-amino-5-morpholino-3-(naphthalen-1-ylmethyl)pyrazolo[1,5-a]pyrimidin-7-ol,
2-amino-3-(2-methyl-3-(trifluoromethyl)benzyl)-5-morpholinopyrazolo[1,5-a]pyrimidin-7-ol,
2-amino-3-(2-methyl-3-(trifluoromethyl)benzyl)-5-(tetrahydro-2H-pyran-4-yl)pyrazolo[1,5-a]pyrimidin-7-ol,
2-amino-3-(2,3-dichlorobenzyl)-5-(tetrahydro-2H-pyran-4-yl)pyrazolo[1,5-a]pyrimidin-7-ol hydrochloride,
2-methyl-5-morpholino-3-(naphthalen-1-ylmethyl)pyrazolo[1,5-a]pyrimidin-7-amine,
4,4'-(2-methyl-3-(naphthalen-1-ylmethyl)pyrazolo[1,5-a]pyrimidine-5,7-diyl)dimorpholine,
2-methyl-3-(2-methylbenzyl)-5-(pyridin-4-yl)pyrazolo[1,5-a]pyrimidin-7-ol,
3-(2,3-dichlorobenzyl)-2-methyl-5-(pyridin-4-yl)pyrazolo[1,5-a]pyrimidin-7-ol,
3-(2,3-dichlorobenzyl)-2-ethyl-5-(pyridin-4-yl)pyrazolo[1,5-a]pyrimidin-7-ol,
3-(2,3-dichlorobenzyl)-5-(pyridin-4-yl)-2-(trifluoromethyl)pyrazolo[1,5-a]pyrimidin-7-ol,
3-(2,3-dichlorobenzyl)-1,2-dimethyl-5-(pyridin-4-yl)pyrazolo[1,5-a]pyrimidin-7(1H)-one,
3-(2,3-dichlorobenzyl)-7-methoxy-2-methyl-5-(pyridin-4-yl)pyrazolo[1,5-a]pyrimidine,
3-(2,3-dichlorobenzyl)-2-methoxy-5-(pyridin-4-yl)pyrazolo[1,5-a]pyrimidin-7-ol,
2-methyl-3-(2-methyl-3-(trifluoromethyl)benzyl)-5-morpholinopyrazolo[1,5-a]pyrimidine-7-carboxylic acid,
2-methyl-5-morpholino-3-(naphthalen-1-ylmethyl)pyrazolo[1,5-a]pyrimidine-7-carboxylic acid,
2-methyl-5-morpholino-3-(naphthalen-1-ylmethyl)pyrazolo[1,5-a]pyrimidine-7-carboxamide,
2-methyl-3-(2-methyl-3-(trifluoromethyl)benzyl)-5-morpholinopyrazolo[1,5-a]pyrimidine-7-carboxamide,
4-(2-methyl-3-(naphthalen-1-ylmethyl)-7-(1H-1,2,4-triazol-3-yl)pyrazolo[1,5-a]pyrimidin-5-yl)morpholine,
4-(2-methyl-3-(2-methyl-3-(trifluoromethyl)benzyl)-7-(1H-1,2,4-triazol-3-yl)pyrazolo[1,5-a]pyrimidin-5-yl)morpholine,
4-(2-methyl-3-(naphthalen-1-ylmethyl)-7-(1H-pyrazol-3-yl)pyrazolo[1,5-a]pyrimidin-5-yl)morpholine,
4-(7-(1H-imidazol-2-yl)-2-methyl-3-(naphthalen-1-ylmethyl)pyrazolo[1,5-a]pyrimidin-5-yl)morpholine,
4-(7-(1H-imidazol-1-yl)-2-methyl-3-(naphthalen-1-ylmethyl)pyrazolo[1,5-a]pyrimidin-5-yl)morpholine,
2-methyl-3-(2-methyl-3-(trifluoromethyl)benzyl)-5-morpholinopyrazolo[1,5-a]pyrimidine-7-carbonitrile,
4-(2-methyl-3-(2-methyl-3-(trifluoromethyl)benzyl)-7-(2H-tetrazol-5-yl)pyrazolo[1,5-a]pyrimidin-5-yl)morpholine,
4-(2-methyl-3-(naphthalen-1-ylmethyl)-7-(1H-tetrazol-5-yl)pyrazolo[1,5-a]pyrimidin-5-yl)morpholine,
4-(3-(2-methyl-3-(trifluoromethyl)benzyl)-7-(1H-pyrazol-4-yl)pyrazolo[1,5-a]pyrimidin-5-yl)morpholine,
2-methyl-3-(2-methylbenzyl)-7-(1H-pyrazol-4-yl)-5-(pyridin-4-yl)pyrazolo[1,5-a]pyrimidine, 3-(2,3-dichlorobenzyl)-7-hydroxy-1-methyl-5-(pyridin-4-yl)pyrazolo[1,5-a]pyrimidin-2(1H)-one, and
1,2-dimethyl-3-(2-methylbenzyl)-5-(pyridin-4-yl)pyrazolo[1,5-a]pyrimidin-7(1H)-one, and pharmaceutically acceptable salts thereof.

By the term "alkoxy" as used herein is meant —O(alkyl) including —OCH$_3$, —OCH$_2$CH$_3$ and —OC(CH$_3$)$_3$ where alkyl is as described herein.

By the term "heteroaryl" as used herein, unless otherwise defined, is meant an aromatic ring system containing carbon(s) and at least one heteroatom. Heteroaryl may be monocyclic or polycyclic. A monocyclic heteroaryl group may have 1 to 3 heteroatoms in the ring, while a polycyclic heteroaryl may contain 1 to 10 hetero atoms. A polycyclic heteroaryl ring may contain fused, spiro or bridged ring junctions, for example, bicyclic heteroaryl is a polycyclic heteroaryl. Bicyclic heteroaryl rings may contain from 8 to 12 member atoms. Monocyclic heteroaryl rings may contain from 5 to 8 member atoms (carbons and heteroatoms). Exemplary heteroaryl groups include: benzofuran, benzothiophene, furan, imidazole, indole, isothiazole, oxazole, pyrazine, pyrazole, pyridazine, pyridine, pyrimidine, pyrrole, quinoline, quinazoline, quinoxaline, thiazole, and thiophene.

By the term "heterocycle" as used herein is meant a non-aromatic, unsaturated or saturated, monocyclic or polycyclic, heterocyclic ring containing 4-6 member atoms which include at least one carbon and at least one heteroatom. Exemplary monocyclic heterocyclic rings include: piperidine, piperazine, pyrrolidine, and morpholine. Exemplary polycyclic heterocyclic rings include quinuclidine.

By the term "substituted" as used herein, unless otherwise defined, is meant that the subject chemical moiety has one to five substituents, suitably from one to three, selected from the group consisting of: hydrogen, halogen, C1-C6alkyl, amino, trifluoromethyl, carboxylic acid, C3-C7cycloalkyl, heterocycloalkyl, cyano, hydroxy, alkoxy, alkylthio, acetyl, nitro, oxo, and heteroaryl, wherein the heteroaryl are optionally substituted with one to three groups independently selected from halogen and C1-3alkyl.

By the term "heteroatom" as used herein is meant oxygen, nitrogen or sulfur.

By the term "halogen" or "halo" as used herein is meant a substituent selected from bromide, iodide, chloride and fluoride.

By the term "alkyl" and derivatives thereof and in all carbon chains as used herein, is meant a linear or branched, substituted or unsubstituted, saturated or unsaturated hydrocarbon chain, and unless otherwise defined, the carbon chain will contain from 1 to 12 carbon atoms.

By the term "co-administering" and derivatives thereof as used herein is meant either simultaneous administration or any manner of separate sequential administration of a PI3 kinase inhibiting compound, as described herein, and a further active ingredient or ingredients. The term further active ingredient or ingredients, as used herein, includes any compound or therapeutic agent known to or that demonstrates advantageous properties when administered to a patient in need of treatment. Suitably, if the administration is not simultaneous, the compounds are administered in a close time proximity to each other. Furthermore, it does not matter if the compounds are administered in the same dosage form, e.g. one compound may be administered topically and another compound may be administered orally.

The term "compound" as used herein includes all isomers of the compound. Examples of such isomers include: enantiomers, tautomers, rotamers.

Certain compounds described herein may contain one or more chiral atoms, or may otherwise be capable of existing as two enantiomers, or two or more diastereoisomers. Accordingly, the compounds of this invention include mixtures of enantiomers/diastereoisomers as well as purified enantiomers/diastereoisomers or enantiomerically/diastereoisomerically enriched mixtures. Also included within the scope of the invention are the individual isomers of the compounds represented by Formula (I) above as well as any wholly or partially equilibrated mixtures thereof. The present invention also covers the individual isomers of the compounds represented by the formulas above as mixtures with isomers thereof in which one or more chiral centers are inverted. The present invention also includes isotopomers of the compounds of Formula (I). Examples of such isotopomers include but not limited to compounds with one of more deuterium atoms.

Compounds of Formula (I) are included in the pharmaceutical compositions of the invention. Where a —COOH or —OH group is present, pharmaceutically acceptable esters can be employed, for example methyl, ethyl, pivaloyloxymethyl, and the like for —COOH, and acetate maleate and the like for —OH, and those esters known in the art for modifying solubility or hydrolysis characteristics, for use as sustained release or prodrug formulations.

It will be appreciated by those skilled in the art that the compounds of formula (I) may be utilized as a pharmaceutically acceptable salt version thereof. The pharmaceutically acceptable salts of the compounds of formula (I) include conventional salts formed from pharmaceutically acceptable (i.e., non-toxic) inorganic or organic acids or bases as well as quaternary ammonium salts. Representative salts include the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, ethanol amine, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate (methanesulfonate), methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate (methylbenzenesulfonate), triethiodide, trimethylammonium and valerate. Other salts, such as oxalic and trifluoroacetic, which are not themselves pharmaceutically acceptable, may be useful in the preparation of salts useful as intermediates in obtaining compounds of this invention and these form a further aspect of the invention. In one embodiment, the compound of formula (I) is in the form of the free base.

Processes for preparing pharmaceutically acceptable salts of compounds such as the compounds of formula (I) are conventional in the art. See, e.g., Burger's Medicinal Chemistry And Drug Discovery 5th Edition, Vol 1: Principles And Practice.

As will be apparent to those skilled in the art, in the processes described below for the preparation of compounds of formula (I), certain intermediates, may be in the form of pharmaceutically acceptable salts of the compound. Processes for preparing pharmaceutically acceptable salts of intermediates are known in the art and are analogous to the processes for preparing pharmaceutically acceptable salts of other compounds such as the compounds of formula (I).

It has now been found that compounds of the present invention are inhibitors of the Phosphatoinositides 3-kinases (PI3Ks). When the phosphatoinositides 3-kinase (PI3K) enzyme is inhibited by a compound of the present invention, PI3K is unable to exert its enzymatic, biological and/or pharmacological effects. The compounds of the present invention are therefore useful in the treatment of autoimmune disorders, inflammatory diseases, cardiovascular diseases, neurodegenerative diseases, allergy, asthma, pancreatitis, multiorgan failure, kidney diseases, platelet aggregation, cancer, sperm motility, transplantation rejection, graft rejection and lung injuries.

As used herein, the term "treatment" or "treating" in the context of therapeutic methods, refers to alleviating the specified condition, eliminating or reducing the symptoms of the condition, slowing or eliminating the progression, invasion, or metastatic spread of the condition and preventing or delaying the reoccurrence of the condition in a previously afflicted subject. The present invention further provides use of the compounds of the invention for the preparation of a medicament for the treatment of several conditions in a mammal (e.g., human) in need thereof.

By the term "prophylaxis" or "prophylatic therapy" is meant the institution of measures to protect a person from a disease to which he or she has been, or may be, exposed. Also called preventive treatment.

Compounds according to Formula (I) are suitable for the modulation, notably the inhibition of the activity of phosphatoinositides 3-kinases (PI3K), suitably phosphatoinositides 3-kinase (PI3Kβ). Therefore the compounds of the present invention are also useful for the treatment of disorders which are mediated by PI3Ks. Said treatment involves the modulation—notably the inhibition or the down regulation—of the phosphatoinositides 3-kinases.

Because the pharmaceutically active compounds of the present invention are active as PI3 kinase inhibitors, particularly the compounds that inhibit PI3Kβ, either selectively or in conjunction with one or more of PI3Kδ, PI3Kα, and/or PI3Kγ, they exhibit When a compound of Formula (I) is administered for the treatment of cancer, the term "co-administering" and derivatives thereof as used herein is meant either simultaneous administration or any manner of separate sequential administration of a PI3 kinase inhibiting compound, as described herein, and a further active ingredient or ingredients, known to be useful in the treatment of cancer, including chemotherapy and radiation treatment. The term further active ingredient or ingredients, as used herein, includes any compound or therapeutic agent known to or that demonstrates advantageous properties when administered to a patient in need of treatment for cancer. Preferably, if the administration is not simultaneous, the compounds are administered in a close time proximity to each other. Furthermore, it does not matter if the compounds are administered in the same dosage form, e.g. one compound may be administered topically and another compound may be administered orally.

Typically, any anti-neoplastic agent that has activity versus a susceptible tumor being treated may be co-administered in the treatment of cancer in the present invention. Examples of such agents can be found in Cancer Principles and Practice f Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracycline, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; non-receptor tyrosine kinase angiogenesis inhibitors; immunotherapeutic agents; proapoptotic agents; and cell cycle signaling inhibitors.

Examples of a further active ingredient or ingredients for use in combination or co-administered with the present PI3 kinase inhibiting compounds are chemotherapeutic agents.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that operate at the $G_2$/M phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)—N-benzoyl-3-phenylisoserine; is a natural diterpene product isolated from the Pacific yew tree *Taxus brevifolia* and is commercially available as an injectable solution TAXOL®. It is a member of the taxane family of terpenes. It was first isolated in 1971 by Wani et al. J. Am. Chem, Soc., 93:2325. 1971), who characterized its structure by chemical and X-ray crystallographic methods. One mechanism for its activity relates to paclitaxel's capacity to bind tubulin, thereby inhibiting cancer cell growth. Schiff et al., Proc. Natl. Acad, Sci. USA, 77:1561-1565 (1980); Schiff et al., Nature, 277:665-667 (1979); Kumar, J. Biol, Chem, 256: 10435-10441 (1981). For a review of synthesis and anticancer activity of some paclitaxel derivatives see: D. G. I. Kingston et al., Studies in Organic Chemistry vol. 26, entitled "New trends in Natural Products Chemistry 1986", Attaur-Rahman, P. W. Le Quesne, Eds. (Elsevier, Amsterdam, 1986) pp 219-235.

Paclitaxel has been approved for clinical use in the treatment of refractory ovarian cancer in the United States (Markman et al., Yale Journal of Biology and Medicine, 64:583, 1991; McGuire et al., Ann. Intem, Med., 111:273, 1989) and for the treatment of breast cancer (Holmes et al., J. Nat. Cancer Inst., 83:1797, 1991.) It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p. 16-23, 1995).

Docetaxel, (2R,3S)—N-carboxy-3-phenylisoserine, N-tert-butyl ester, 13-ester with 5β,20-epoxy-1,2α,4,7β,10β, 13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree. The dose limiting toxicity of docetaxel is neutropenia.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleukoblastine[R—(R*,R*)-2,3-dihydroxybutanedioate (1:2) (salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer. The primary dose limiting side effects of cisplatin are nephrotoxicity, which may be controlled by hydration and diuresis, and ototoxicity.

Carboplatin, platinum, diammine[1,1-cyclobutane-dicarboxylate(2-)-O,O'], is commercially available as PARAPLATIN® as an injectable solution. Carboplatin is primarily indicated in the first and second line treatment of advanced ovarian carcinoma. Bone marrow suppression is the dose limiting toxicity of carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxy, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias. Alopecia, nausea, vomiting and leukopenia are the most common dose limiting side effects of cyclophosphamide.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Bone marrow suppression is the most common dose limiting side effect of chlorambucil.

Busulfan, 1,4-butanediol dimethanesulfonate, is commercially available as MYLERAN® TABLETS. Busulfan is indicated for the palliative treatment of chronic myelogenous leukemia. Bone marrow suppression is the most common dose limiting side effects of busulfan.

Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas. Delayed myelosuppression is the most common dose limiting side effects of carmustine.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease. Nausea, vomiting, and anorexia are the most common dose limiting side effects of dacarbazine.

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Dactinomycin, also know as Actinomycin D, is commercially available in injectable form as COSMEGEN®. Dactinomycin is indicated for the treatment of Wilm's tumor and rhabdomyosarcoma. Nausea, vomiting, and anorexia are the most common dose limiting side effects of dactinomycin.

Daunorubicin, (8S-cis-)-8-acetyl-10-[(3-amino-2,3,6-trideoxy-α-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Myelosuppression is the most common dose limiting side effect of daunorubicin.

Doxorubicin, (8S,10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas. Myelosuppression is the most common dose limiting side effect of doxorubicin.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas. Pulmonary and cutaneous toxicities are the most common dose limiting side effects of bleomycin.

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers. Myelosuppression is the most common side effect of etoposide. The incidence of leucopenia tends to be more severe than thrombocytopenia.

Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children. Myelosuppression is the most common dose limiting side effect of teniposide. Teniposide can induce both leucopenia and thrombocytopenia.

Antimetabolite neoplastic agents are phase specific anti-neoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mecaptopurine, thioguanine, and gemcitabine.

5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Myelosuppression and mucositis are dose limiting side effects of 5-fluorouracil. Other fluoropyrimidine analogs include 5-fluoro deoxyuridine (floxuridine) and 5-fluorodeoxyuridine monophosphate.

Cytarabine, 4-amino-1-β-D-arabinofuranosyl-2 (1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Cytarabine induces leucopenia, thrombocytopenia, and mucositis.

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. Myelosuppression and gastrointestinal mucositis are expected side effects of mercaptopurine at high doses. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Myelosuppression, including leucopenia, thrombocytopenia, and anemia, is the most common dose limiting side effect of thioguanine administration. However, gastrointestinal side effects occur and can be dose limiting. Other purine analogs include pentostatin, erythrohydroxynonyladenine, fludarabine phosphate, and cladribine.

Gemcitabine, 2'-deoxy-2',2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer. Myelosuppression, including leucopenia, thrombocytopenia, and anemia, is the most common dose limiting side effect of gemcitabine administration.

Methotrexate, N-[4[[(2,4-diamino-6-pteridinyl)methyl] methylamino]benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder. Myelosuppression (leucopenia, thrombocytopenia, and anemia) and mucositis are expected side effect of methotrexate administration.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperidinopiperidino) carbonyloxy]-1H-pyrano[3',4',6,7]indolizino[1,2-b]quinoline-3,14(4H,12H)-dione hydrochloride, is commercially available as the injectable solution CAMPTOSAR®.

Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I:DNA:irintecan or SN-38 ternary complex with replication enzymes. Irinotecan is indicated for treatment of metastatic cancer of the colon or rectum. The dose limiting side effects of irinotecan HCl are myelosuppression, including neutropenia, and GI effects, including diarrhea.

Topotecan HCl, (S)-10-[(dimethylamino)methyl]-4-ethyl-4,9-dihydroxy-1H-pyrano[3',4',6,7]indolizino[1,2-b]quinoline-3,14-(4H,12H)-dione monohydrochloride, is commercially available as the injectable solution HYCAMTIN®. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer. The dose limiting side effect of topotecan HCl is myelosuppression, primarily neutropenia.

Also of interest, is the camptothecin derivative of formula A following, currently under development, including the racemic mixture (R,S) form as well as the R and S enantiomers:

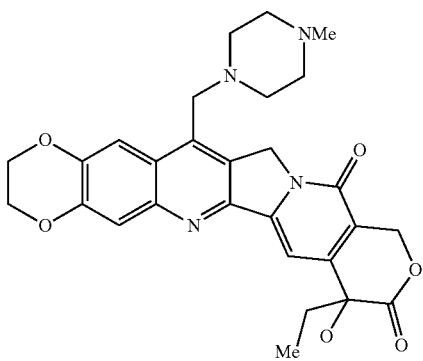

A known by the chemical name "7-(4-methylpiperazino-methylene)-10,11-ethylenedioxy-20(R,S)-camptothecin (racemic mixture) or "7-(4-methylpiperazino-methylene)-10,11-ethylenedioxy-20(R)-camptothecin (R enantiomer) or "7-(4-methylpiperazino-methylene)-10,11-ethylenedioxy-20(S)-camptothecin (S enantiomer). Such compound as well as related compounds are described, including methods of making, in U.S. Pat. Nos. 6,063,923; 5,342,947; 5,559,235; 5,491,237 and pending U.S. patent application Ser. No. 08/977,217 filed Nov. 24, 1997.

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, androgens, and anti-androgens such as flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene, iodoxyfene, as well as selective estrogen receptor modulators (SERMS) such those described in U.S. Pat. Nos. 5,681,835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagagonists such as goserelin acetate and luprolide.

Signal transduction pathway inhibitors are those inhibitors, which block or inhibit a chemical process which evokes an intracellular change. As used herein this change is cell proliferation or differentiation. Signal transduction inhibitors useful in the present invention include inhibitors of receptor tyrosine kinases, non-receptor tyrosine kinases, SH2/SH3domain blockers, serine/threonine kinases, phosphotidyl inositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by overexpression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath, John C., Exp. Opin. Ther. Patents (2000) 10(6):803-818; Shawver et al DDT Vol 2, No. 2 Feb. 1997; and Lofts, F. J. et al, "Growth factor receptors as targets", New Molecular Targets for Cancer Chemotherapy, ed. Workman, Paul and Kerr, David, CRC press 1994, London.

Tyrosine kinases, which are not growth factor receptor kinases are termed non-receptor tyrosine kinases. Non-receptor tyrosine kinases useful in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S. and Corey, S. J., (1999) Journal of Hematotherapy and Stem Cell Research 8 (5): 465-80; and Bolen, J. B., Brugge, J. S., (1997) Annual review of Immunology. 15: 371-404.

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, AKT kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P., Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; U.S. Pat. No. 6,268,391; and Martinez-Iacaci, L., et al, Int. J. Cancer (2000), 88(1), 44-52.

Inhibitors of Phosphotidyl inositol-3 Kinase family members including blockers of PI3-kinase, ATM, DNA-PK, and Ku are also useful in the present invention. Such kinases are discussed in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer res, (2000) 60(6), 1541-1545.

Also useful in the present invention are Myo-inositol signaling inhibitors such as phospholipase C blockers and Myo-inositol analogues. Such signal inhibitors are described in Powis, G., and Kozikowski A., (1994) New Molecular Targets for Cancer Chemotherapy ed., Paul Workman and David Kerr, CRC press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9 (2) 99-102; and BioChem. Biophys. Acta, (19899) 1423(3):19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imclone C225 EGFR specific antibody (see Green, M. C. et al, Monoclonal Antibody Therapy for Solid Tumors, Cancer Treat. Rev., (2000), 26(4), 269-286); Herceptin® erbB2 antibody (see Tyrosine Kinase Signalling in Breast cancer:erbB Family Receptor Tyrosine Kinases, Breast cancer Res., 2000, 2(3), 176-183); and 2CB VEGFR2 specific antibody (see Brekken, R. A. et al, Selective Inhibition of VEGFR2 Activity by a monoclonal Anti-VEGF antibody blocks tumor growth in mice, Cancer Res. (2000) 60, 5117-5124).

Non-receptor kinase angiogenesis inhibitors may also find use in the present invention. Inhibitors of angiogenesis related VEGFR and TIE2 are discussed above in regard to signal transduction inhibitors (both receptors are receptor tyrosine kinases). Angiogenesis in general is linked to erbB2/EGFR signaling since inhibitors of erbB2 and EGFR have been shown to inhibit angiogenesis, primarily VEGF expression. Thus, the combination of an erbB2/EGFR inhibitor with an inhibitor of angiogenesis makes sense. Accordingly, non-receptor tyrosine kinase inhibitors may be used in combination with the EGFR/erbB2 inhibitors of the present invention. For example, anti-VEGF antibodies, which do not recognize VEGFR (the receptor tyrosine kinase), but bind to the ligand; small molecule inhibitors of integrin (alpha$_v$, beta$_3$) that will inhibit angiogenesis; endostatin and angiostatin (non-RTK) may also prove useful in combination with the disclosed erb family inhibitors. (See Bruns C J et al (2000), Cancer Res., 60: 2926-2935; Schreiber A B, Winkler M E, and Derynck R. (1986), Science, 232: 1250-1253; Yen L et al. (2000), Oncogene 19: 3460-3469).

Agents used in immunotherapeutic regimens may also be useful in combination with the compounds of formula (I). There are a number of immunologic strategies to generate an immune response against erbB2 or EGFR. These strategies are generally in the realm of tumor vaccinations. The efficacy of immunologic approaches may be greatly enhanced through combined inhibition of erbB2/EGFR signaling pathways using a small molecule inhibitor. Discussion of the immunologic/tumor vaccine approach against erbB2/EGFR are found in Reilly R T et al. (2000), Cancer Res. 60: 3569-3576; and Chen Y, Hu D, Eling D J, Robbins J, and Kipps T J. (1998), Cancer Res. 58: 1965-1971.

Agents used in proapoptotic regimens (e.g., bcl-2 antisense oligonucleotides) may also be used in the combination of the present invention. Members of the Bcl-2 family of proteins block apoptosis. Upregulation of bcl-2 has therefore been linked to chemoresistance. Studies have shown that the epidermal growth factor (EGF) stimulates anti-apoptotic members of the bcl-2 family (i.e., mcl-1). Therefore, strategies designed to downregulate the expression of bcl-2 in tumors have demonstrated clinical benefit and are now in Phase II/III trials, namely Genta's G3139 bcl-2 antisense oligonucleotide. Such proapoptotic strategies using the antisense oligonucleotide strategy for bcl-2 are discussed in Water J S et al. (2000), J. Clin. Oncol. 18: 1812-1823; and Kitada S et al. (1994), Antisense Res. Dev. 4: 71-79.

Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania et al, Exp. Opin. Ther. Patents (2000) 10(2):215-230.

In one embodiment, the cancer treatment method of the claimed invention includes the co-administration a compound of formula I and/or a pharmaceutically acceptable salt, hydrate, solvate or pro-drug thereof and at least one antineoplastic agent, such as one selected from the group consisting of anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, and cell cycle signaling inhibitors.

Because the pharmaceutically active compounds of the present invention are active as PI3 kinase inhibitors, particularly the compounds that modulate/inhibit PI3Kβ, either selectively or in conjunction with one or more of PI3Kα, PI3Kγ, and/or PI3Kδ, they exhibit therapeutic utility in treating a disease state selected from: autoimmune disorders, inflammatory diseases, cardiovascular diseases, neurodegenerative diseases, allergy, cancer, asthma, pancreatitis, multiorgan failure, kidney diseases, platelet aggregation, sperm motility, transplantation rejection, graft rejection and lung injuries.

When a compound of Formula (I) is administered for the treatment of a disease state selected from: autoimmune disorders, inflammatory diseases, cardiovascular diseases, neurodegenerative diseases, cancer, allergy, asthma, pancreatitis, multiorgan failure, kidney diseases, platelet aggregation, sperm motility, transplantation rejection, graft rejection or lung injuries, the term "co-administering" and derivatives thereof as used herein is meant either simultaneous administration or any manner of separate sequential administration of a PI3 kinase inhibiting compound, as described herein, and a further active ingredient or ingredients, known to be useful in the treatment of autoimmune disorders, inflammatory diseases, cardiovascular diseases, cancer, neurodegenerative diseases, allergy, asthma, pancreatitis, multiorgan failure, kidney diseases, platelet aggregation, sperm motility, transplantation rejection, graft rejection and/or lung injuries.

The pharmaceutically active compounds within the scope of this invention are useful as PI3 Kinase inhibitors in mammals, particularly humans, in need thereof.

The present invention therefore provides a method of treating diseases associated with PI3 kinase activation or PTEN inactivation, particularly: autoimmune disorders, inflammatory diseases, cardiovascular diseases, neurodegenerative diseases, allergy, asthma, pancreatitis, multiorgan failure, kidney diseases, platelet aggregation, cancer, sperm motility, transplantation rejection, graft rejection and lung injuries and other conditions requiring PI3 kinase modulation/inhibition, which comprises administering an effective compound of Formula (I) or a pharmaceutically acceptable salt, hydrate, solvate or pro-drug thereof. The compounds of Formula (I) also provide for a method of treating the above indicated disease states because of their ability to act as PI3 inhibitors. The drug may be administered to a patient in need thereof by any conventional route of administration, including, but not limited to, intravenous, intramuscular, oral, subcutaneous, intradermal, and parenteral.

The pharmaceutically active compounds of the present invention are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the presently invented pharmaceutically active compounds in a pharmaceutical dosage unit as described above will be an efficacious, nontoxic quantity preferably selected from the range of 0.001-100 mg/kg of active compound, preferably 0.001-50 mg/kg. When treating a human patient in need of a PI3K inhibitor, the selected dose is administered preferably from 1-6 times daily, orally or parenterally. Preferred forms of parenteral administration include topically, rectally, transdermally, by injection and continuously by infusion. Oral dosage units for human administration preferably contain from 0.05 to 3500 mg of active compound. Oral administration, which uses lower dosages is preferred. Parenteral administration, at high dosages, however, also can be used when safe and convenient for the patient.

Optimal dosages to be administered may be readily determined by those skilled in the art, and will vary with the particular PI3 kinase inhibitor in use, the strength of the preparation, the mode of administration, and the advancement of the disease condition. Additional factors depending on the particular patient being treated will result in a need to adjust dosages, including patient age, weight, diet, and time of administration.

The method of this invention of inducing PI3 kinase inhibitory activity in mammals, including humans, comprises administering to a subject in need of such activity an effective PI3 kinase modulating/inhibiting amount of a pharmaceutically active compound of the present invention.

The invention also provides for the use of a compound of Formula (I) in the manufacture of a medicament for use as a PI3 kinase inhibitor.

The invention also provides for the use of a compound of Formula (I) in the manufacture of a medicament for use in therapy.

The invention also provides for the use of a compound of Formula (I) in the manufacture of a medicament for use in treating autoimmune disorders, inflammatory diseases, cardiovascular diseases, neurodegenerative diseases, allergy, asthma, pancreatitis, multiorgan failure, kidney diseases, platelet aggregation, cancer, sperm motility, transplantation rejection, graft rejection and lung injuries.

The invention also provides for a pharmaceutical composition for use as a PI3 inhibitor which comprises a compound of Formula (I) and a pharmaceutically acceptable carrier.

The invention also provides for a pharmaceutical composition for use in the treatment of autoimmune disorders, inflammatory diseases, cardiovascular diseases, neurodegenerative diseases, allergy, asthma, pancreatitis, multiorgan failure, kidney diseases, platelet aggregation, cancer, sperm motility, transplantation rejection, graft rejection and lung injuries, which comprises a compound of Formula (I) and a pharmaceutically acceptable carrier.

No unacceptable toxicological effects are expected when compounds of the invention are administered in accordance with the present invention.

In addition, the pharmaceutically active compounds of the present invention can be co-administered with further active ingredients, including compounds known to have utility when used in combination with a PI3 kinase inhibitor.

Without further elaboration, it is believed that one skilled in the art can, using the preceding description, utilize the present invention to its fullest extent. The following examples are, therefore, to be construed as merely illustrative and not a limitation of the scope of the present invention in any way.

Schemes

Pyrazolopyrimidines as PI3K Inhibitors

Formula I

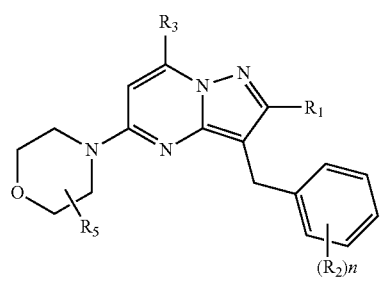

Many of the pyrazolopyrimidines of Formula I can be prepared using the general synthetic schemes described below:

Scheme I

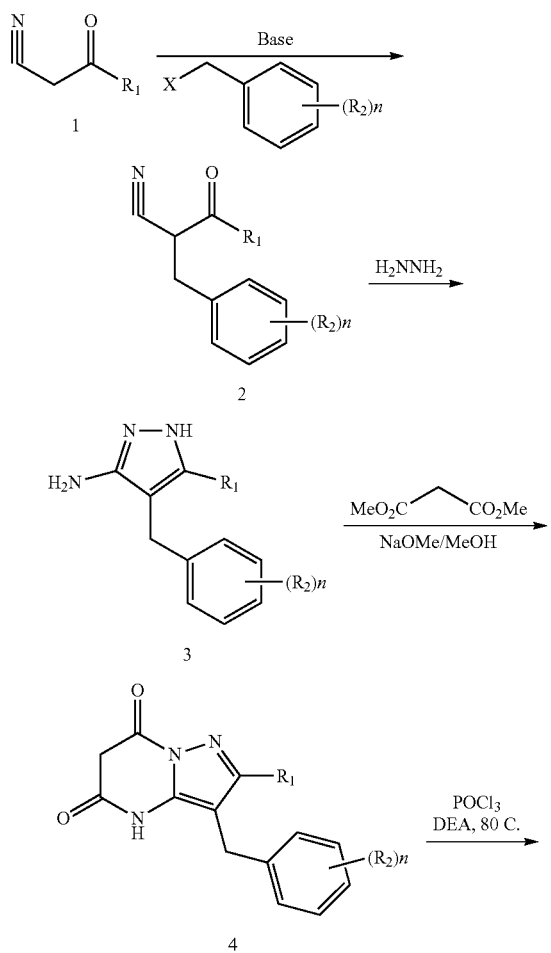

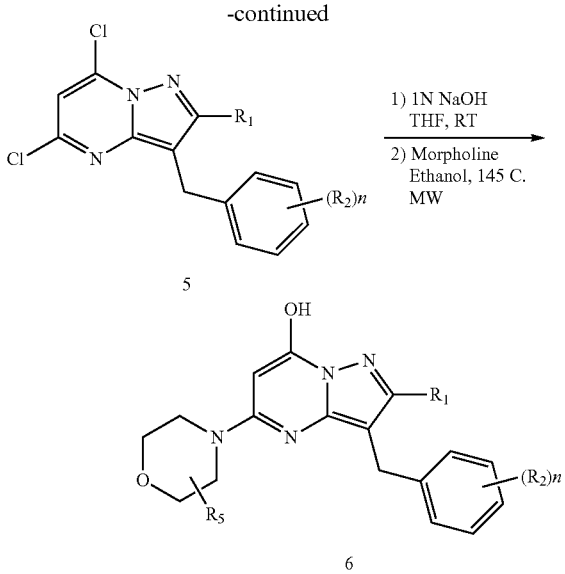

Beta-ketonitrile 1 can be alkylated with a variety of aryl or heteroaryl methyl halides to provide substituted beta-ketonitrile 2 which can be subsequently reacted with hydrazine in an alcoholic solvent to provide substituted amino pyrazole 3. Condensation of 3 with dimethyl malonate in the presence of strong base in methanol can afford substituted pyrazolopyrimidine-dione 4 which can then be converted to dichloride (5) in the presence of $POCl_3$. Selective hydrolysis of the 7-chloro with hydroxide, followed by reaction with morpholine can then provide the desired morpholine substituted pyrazolopyrimidinone 6.

Scheme II

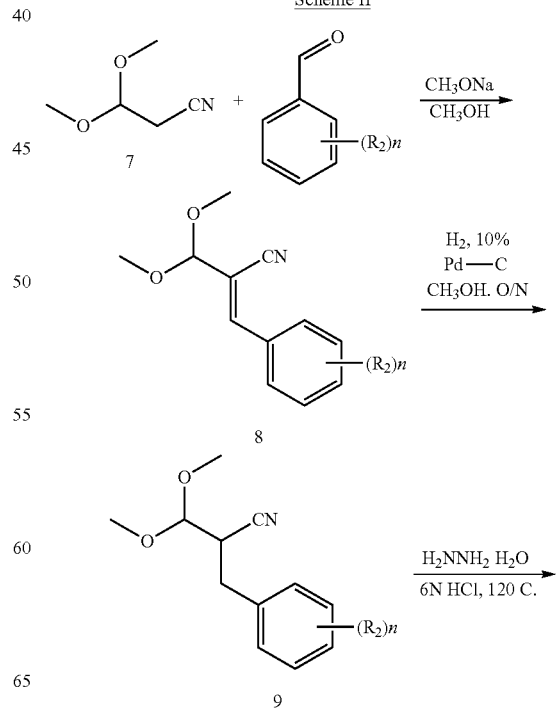

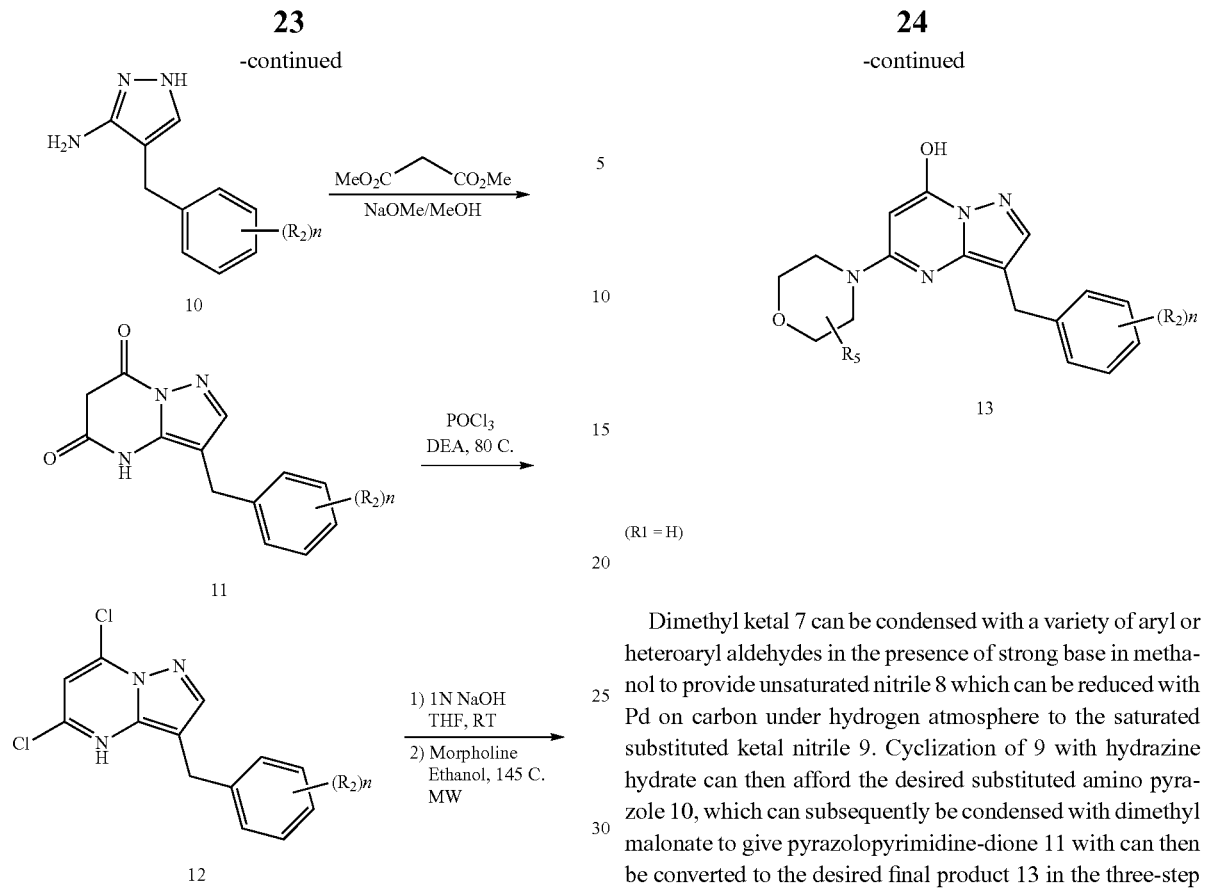

Dimethyl ketal 7 can be condensed with a variety of aryl or heteroaryl aldehydes in the presence of strong base in methanol to provide unsaturated nitrile 8 which can be reduced with Pd on carbon under hydrogen atmosphere to the saturated substituted ketal nitrile 9. Cyclization of 9 with hydrazine hydrate can then afford the desired substituted amino pyrazole 10, which can subsequently be condensed with dimethyl malonate to give pyrazolopyrimidine-dione 11 with can then be converted to the desired final product 13 in the three-step sequence as previously described in Scheme I.

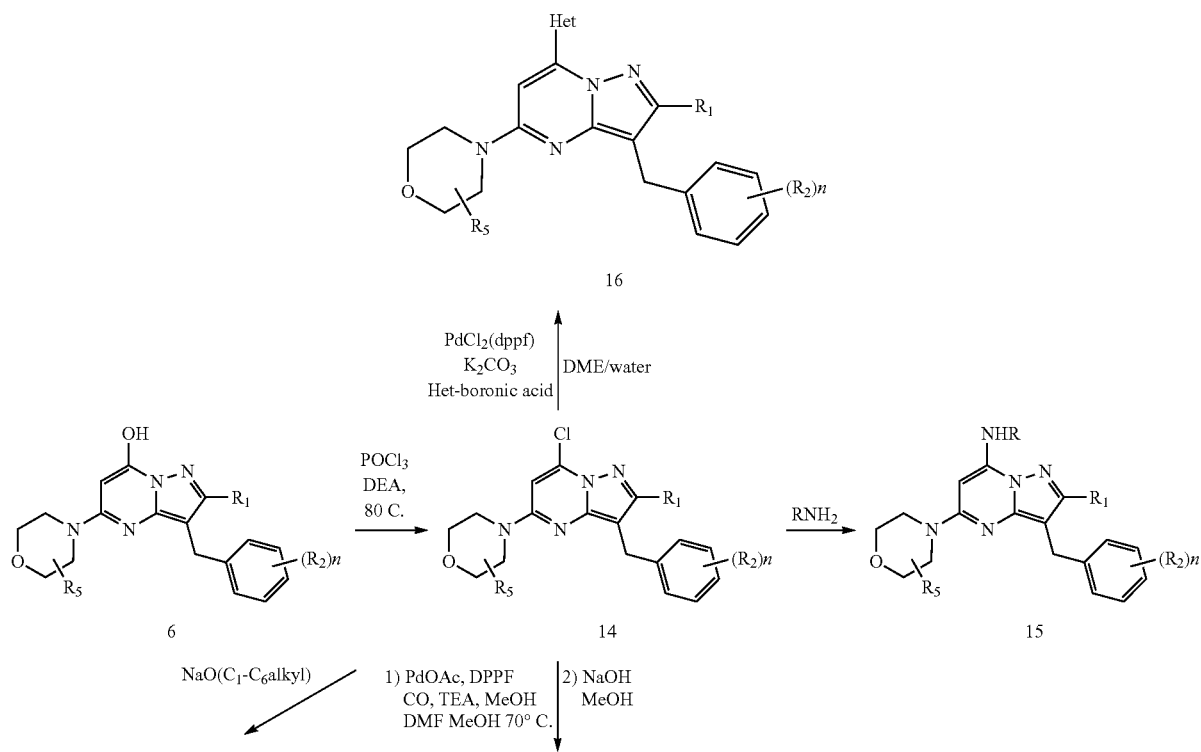

25

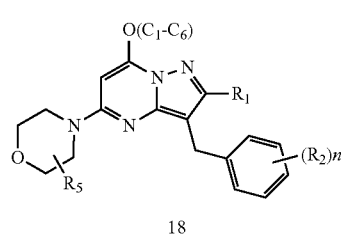

18

-continued

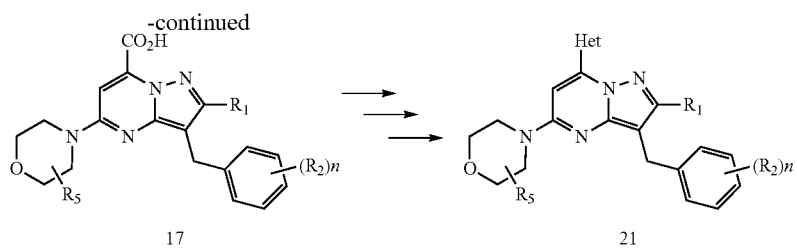

17 → 21

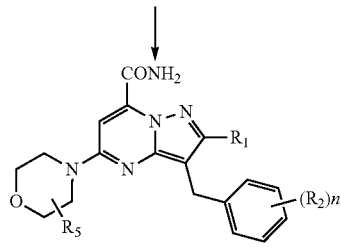

19

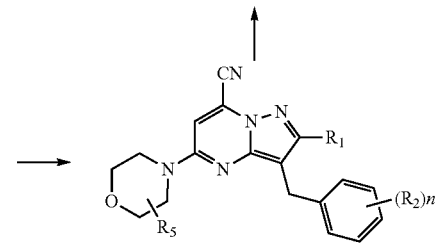

20

(R3 = Het, NHORa, CO2H, CONH2, CN, C1-6alkoxy)

Morpholine substituted pyrazolopyrimidinone 6 can be converted to the versatile intermediate 7-chloro analog (14) in the presence of POCl3. Using standard chemical transformations, 14 can be used to prepare 7-amino (15), 7-heteroaryl (16), 7-CO2H (17), 7-alkoxy (18) and 7-carboxamide (19) analogs. Dehydration of 7-carboxamide (19) analogs can be used to prepare 7-CN (20) analogs. Additionally, acid analog 17 or nitrile analog 19 can be used as precursors to prepare other heterocycles such as tetrazole and triazole analogs (21) using established chemical procedures.

Formula II

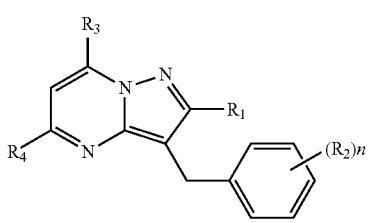

Many of the pyrazolopyrimidines of Formula II can be prepared using the general synthetic schemes described below:

Scheme IV

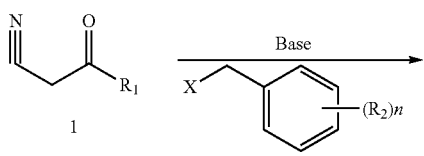

26

-continued

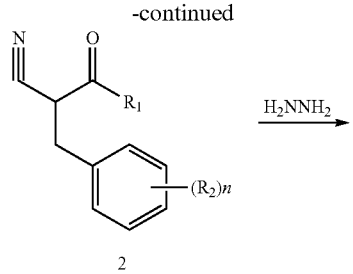

2

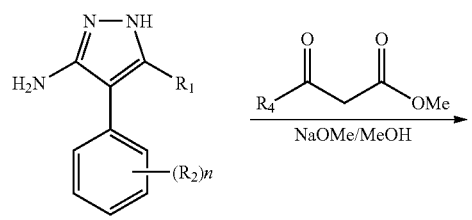

3

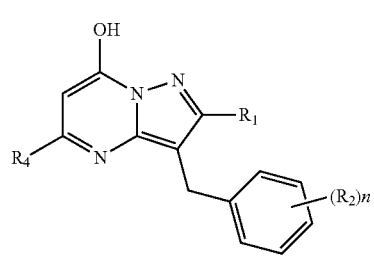

22

(R3 = OH, R4 = 4-Pyr, 4-THP)

Beta-ketonitrile 1 can be alkylated with a variety of aryl or heteroaryl methyl halides to provide substituted beta-ketonitrile 2 which can be subsequently reacted with hydrazine in an alcoholic solvent to provide substituted amino pyrazole 3. Condensation of 3 with a variety of beta-keto esters in the presence of strong base in methanol can provide the desired substituted 5-substituted pyrazolopyrimidinone 22.

EXPERIMENTAL PROCEDURES

Example 1

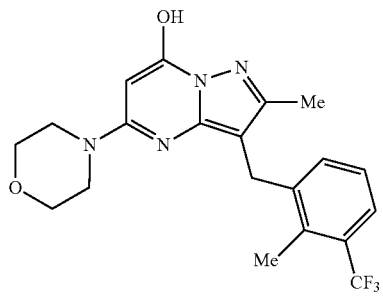

Preparation of 2-methyl-3-(2-methyl-3-(trifluoromethyl)benzyl)-5-morpholinopyrazolo[1,5-a]pyrimidin-7-ol a) 3-methyl-4-{[2-methyl-3-(trifluoromethyl)phenyl]methyl}-1H-pyrazol-5-amine

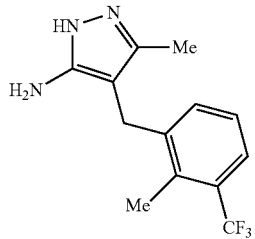 [SMILES: Cc1n[nH]c(N)c1Cc1cccc(C(F)(F)F)c1C]

To a solution of (1-cyano-2-oxopropyl)sodium (3.5 g, 33.2 mmol) in N,N-Dimethylformamide (25 mL) stirred under nitrogen at 0° C. was added a solution of 1-(bromomethyl)-2-methyl-3-(trifluoromethyl)benzene (7.0 g, 27.7 mmol) in 10 ml of DMF dropwise during 30 min. The reaction mixture was stirred at 40° C. for 2 hours. Then this solution was diluted with saturated ammonium chloride solution. This solution was extracted with ethyl acetate (100 mL×3). The combined organic layers were washed with water (30 mL) and brine (30 mL), dried, concentrated to dryness in vacuo. The crude product was purified with on a silica gel column to give 2-{[2-methyl-3-(trifluoromethyl)phenyl]methyl}-3-oxobutanenitrile. (5.2 g, 74%). To a solution of 2-{[2-methyl-3-(trifluoromethyl)phenyl]methyl}3-oxobutanenitrile (5.2 g, 20.4 mmol) in ethanol (400 mL) stirred under nitrogen at 20° C. was added neat hydrazine monohydrate (2.25 g, 30.6 mmol) dropwise during 5 minutes. The reaction mixture was stirred at 100° C. for overnight. After cooled to room temperature, the reaction mixture was evaporated to dryness in vacuo. The residue was purified on a silica gel column (methanol/DCM gradient solvent system) to provide titled product. (2.16 g, 39%); $^1$H NMR (400 MHz, DMSO-$d_6$) δ ppm 1.86 (s, 3H) 2.39 (s, 3H) 3.63 (s, 2H) 4.30 (br. s., 2H) 7.19 (d, J=7.58 Hz, 1H) 7.27 (t, J=7.71 Hz, 1H) 7.49 (s, 1H) 11.09 (br. s., 1H)

b) 2-methyl-3-{[2-methyl-3-(trifluoromethyl)phenyl]methyl}pyrazolo[1,5-a]pyrimidine-5,7(4H,6H)-dione

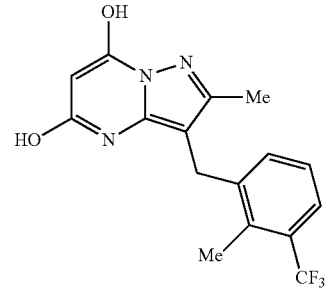 [SMILES: Cc1nn2c(O)cc(O)nc2c1Cc1cccc(C(F)(F)F)c1C]

To a solution of 3-methyl-4-{[2-methyl-3-(trifluoromethyl)phenyl]methyl}-1H-pyrazol-5-amine (2.0 g, 7.43 mmol), dimethyl propanedioate (1.03 g, 7.8 mmol) and in methanol (20 mL) stirred under nitrogen at 20° C. was added a solution of sodium methoxide (3.21 g, 14.9 mmol) in methanol (20 mL) dropwise during 15 minutes. The reaction mixture was stirred at 80° C. for overnight. After the reaction mixture was cooled to room temperature, precipitate was collected by filtration, then washed with methanol (5 mL×2). Product was dried under air. The product was then suspended with 1 N HCl (10 mL), stirred for 10 minutes, and filtered off HCl solution. The product was dried and used in next step without further purification. (2.41 g, 96%); LC/MS: MS (ES$^+$) m/e 338 (MH$^+$).

c) 5,7-dichloro-2-methyl-3-{[2-methyl-3-(trifluoromethyl)phenyl]methyl}pyrazolo[1,5-a]pyrimidine

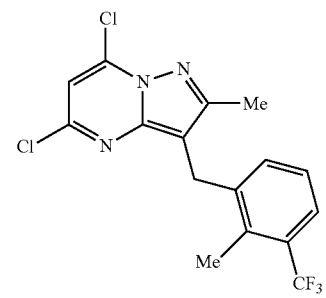 [SMILES: Cc1nn2c(Cl)cc(Cl)nc2c1Cc1cccc(C(F)(F)F)c1C]

To a suspension of N,N-diethylaniline (2.35 g, 15.7 mmol) and 2-methyl-3-{[2-methyl-3-(trifluoromethyl)phenyl]methyl}pyrazolo[1,5-a]pyrimidine-5,7(4H,6H)-dione (2.41 g, 7.2 mmol) stirred under nitrogen at 0° C. was added neat POCl$_3$ (3.33 ml, 35.7 mmol) dropwise during 15 minutes. The reaction mixture was stirred at 80° C. for 3 hrs. Reaction mixture was concentrated. The residue was dissolved with DCM (50 mL) and icy water (10 mL). The pH of aqueous layer was adjusted by 10 N NaOH solution to 8. Two layers were separated. Aqueous layer was extracted with DCM (30 mL) again. Combined DCM solution was dried, concentrated to dryness. Product was purified on silica gel column (ethyl acetate/hexane gradient solvent system). Product was obtained and used in the next step without purification. (1.31 g, 49%); LC/MS: MS (ES⁺) m/e 374 (MH⁺).

d) 5-chloro-2-methyl-3-{[2-methyl-3-(trifluoromethyl)phenyl]methyl}pyrazolo[1,5-a]pyrimidin-7(4H)-one

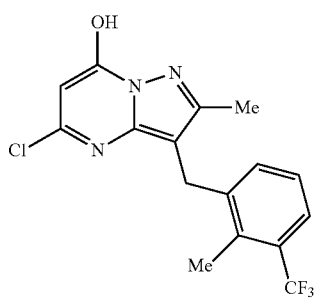

To a suspension of 5,7-dichloro-2-methyl-3-{[2-methyl-3-(trifluoromethyl)phenyl]methyl}pyrazolo[1,5-a]pyrimidine (1.30 g, 3.47 mmol) in tetrahydrofuran (25 ml) was added sodium hydroxide solution (3 mL, 17.37 mmol). The reaction mixture was stirred at 50° C. for 3 hours. Solvent was removed. The residue was dissolved with ethyl acetate (50 mL) and 5% HCl solution (20 mL). Organic layer was separated and dried. The crude material was purified on silica gel column (methanol/DCM, 0-10% gradient solvent system) to give the product. It was used for next step. (0.88 g, 68%); LC/MS: MS (ES⁺) m/e 356 (MH⁺).

e) Preparation of 2-methyl-3-(2-methyl-3-(trifluoromethyl)benzyl)-5-morpholinopyrazolo[1,5-a]pyrimidin-7-ol To a solution of 5-chloro-2-methyl-3-{[2-methyl-3-(trifluoromethyl)phenyl]methyl}pyrazolo[1,5-a]pyrimidin-7(4H)-one (55 mg, 0.155 mmol) in ethanol (1.5 mL) was added morpholine (40.4 mg, 0.464 mmol) in a microwave reaction vessel. It was sealed and irradiated (microwave) at 145° C. for 3 hour. The reaction mixture was then diluted with ethyl acetate (15 mL) and 5% HCl solution (3 mL). Two layers were separated. Organic layer was dried, concentrated and purified with silica gel column (methanol/DCM, 0-10%). The titled compound was obtained. (37 mg, 59%); LC/MS: MS (ES⁺) m/e 407 (MH⁺); 1H NMR (400 MHz, DMSO-d₆) δ ppm 2.08 (s, 3H) 2.45 (s, 3H) 3.31 (d, J=4.80 Hz, 3H) 3.29 (br. s., 1H) 3.69 (br. s., 1H) 3.67 (d, J=5.05 Hz, 3H) 3.96 (s, 2H) 5.07 (s, 1H) 7.15 (br. s., 1H) 7.25-7.32 (m, 1H) 7.54 (d, J=7.83 Hz, 1H).

Example 2

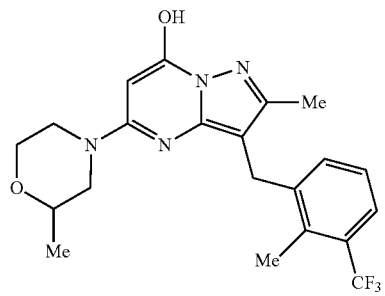 [SMILES: Cc1nn2c(O)cc(N3CCOC(C)C3)nc2c1Cc1cccc(C(F)(F)F)c1C]

Preparation of 2-methyl-3-(2-methyl-3-(trifluoromethyl)benzyl)-5-(2-methylmorpholino)pyrazolo[1,5-a]pyrimidin-7-ol To a solution of 5-chloro-2-methyl-3-{[2-methyl-3-(trifluoromethyl)phenyl]methyl}pyrazolo[1,5-a]pyrimidin-7(4H)-one (60 mg, 0.17 mmol), prepared as described in Example 1, step d, in ethanol (1.5 mL) was added 2-methylmorpholine (85 mg, 0.84 mmol) in a microwave reaction vessel. It was sealed and irradiated (microwave) at 145° C. for one hour. The reaction mixture was diluted with ethyl acetate (15 mL), washed with 5% HCl solution (3 mL). Organic layer was dried, filtered, and concentrated to dryness. The crude was purified by reverse-phase HPLC to provide the titled compound. (28 mg, 39%); LC/MS: MS (ES⁺) m/e 421 (MH⁺); 1H NMR (400 MHz, MeOD) δ ppm 1.17 (br. s., 2H) 1.19 (d, J=1.26 Hz, 1H) 2.13 (br. s., 3H) 2.47 (br. s., 3H) 2.66 (t, J=11.62 Hz, 1H) 2.68 (br. s., 1H) 2.94-3.06 (m, 1H) 3.63 (br. s., 3H) 4.01 (br. s., 2H) 7.11 (br. s., 1H) 7.23 (br. s., 1H) 7.51 (br. s., 1H).

Example 3

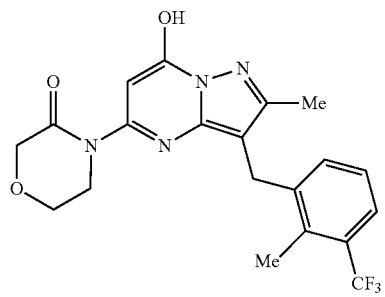 [SMILES: Cc1nn2c(O)cc(N3CCOCC3=O)nc2c1Cc1cccc(C(F)(F)F)c1C]

Preparation of 4-(7-hydroxy-2-methyl-3-(2-methyl-3-(trifluoromethyl)benzyl)pyrazolo[1,5-a]pyrimidin-5-yl)morpholin-3-one To a solution of 5-chloro-2-methyl-3-{[2-methyl-3-(trifluoromethyl)phenyl]methyl}pyrazolo[1,5-a]pyrimidin-7(4H)-one (355 mg, 1.0 mmol), 3-Oxo-morphorine (121 mg, 1.2 mmol) and bis(1,1-dimethylethyl)[3,4,5,6-tetramethyl-2',4',6'-tris(1-methylethyl)-2-biphenylyl]phosphane (24.0 mg, 0.05 mmol) in tert-butanol (25 mL) under nitrogen was added Pd2(dba)3 (18.3 mg, 0.02 mmol), then tripotassium phosphate (254 mg, 1.2 mmol) in one charge. The reaction mixture was stirred at 110° C. for 24 hours. Reaction mixture was concentrated and diluted with ethyl acetate (50 mL) and water (10 mL). Two layers were separated. Organic layer was washed, dried and concentrated to dryness. The crude product was purified with column chromatography to yield desired product. (8.5 mg, 2%); LC/MS: MS (ES$^+$) m/e 421 (MH$^+$); 1H NMR (400 MHz, MeOD) δ ppm 2.22 (s, 3H) 2.49 (d, J=1.52 Hz, 3H) 3.84 (d, J=5.31 Hz, 1H) 3.82 (s, 1H) 4.00 (dd, J=5.94, 4.42 Hz, 2H) 4.04 (s, 2H) 4.26 (s, 2H) 5.89 (s, 1H) 7.21 (d, J=4.55 Hz, 2H) 7.50 (s, 1H).

Example 4

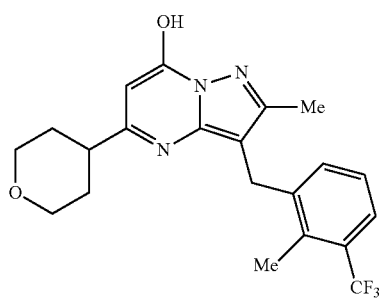

Preparation of 2-methyl-3-(2-methyl-3-(trifluoromethyl)benzyl)-5-(tetrahydro-2H-pyran-4-yl)pyrazolo[1,5-a]pyrimidin-7-ol To a suspension of ethyl 3-oxo-3-(tetrahydro-2H-pyran-4-yl)propanoate (98 mg, 0.49 mmol) in acetic acid (2 mL) was added 3-methyl-4-{[2-methyl-3-(trifluoromethyl)phenyl]methyl}-1H-pyrazol-5-amine (125 mg, 0.46 mmol), prepared as described in Example 1, step a, in microwave reaction vessel. It was sealed and heated with microwave reactor at 140° C. for 40 minutes. The reaction mixture was cooled, diluted with acetic acid (2 mL) and stood for overnight. Precipitate was observed, filtered. Solid was washed with cooled methanol. Solid was dried. The titled compound was obtained. (75 mg, 38%) LC/MS: MS (ES$^+$) m/e 406 (MH$^+$); 1H NMR (400 MHz, DMSO-d$_6$) δ ppm 1.68-1.80 (m, 4H) 2.05 (s, 3H) 2.46 (s, 3H) 2.75 (s, 1H) 3.37 (td, J=11.68, 2.40 Hz, 2H) 3.95 (d, J=14.40 Hz, 2H) 3.99 (s, 2H) 5.57 (s, 1H) 7.00 (d, J=7.33 Hz, 1H) 7.28 (t, J=7.45 Hz, 1H) 7.55 (d, J=7.58 Hz, 1H) 11.59 (d, J=1.01 Hz, 1H).

Example 5

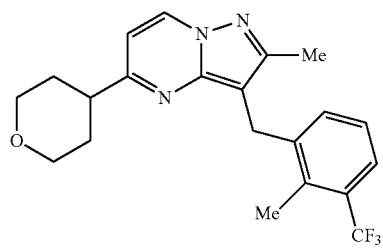 [SMILES: Cc1nn2ccc(C3CCOCC3)nc2c1Cc1cccc(C(F)(F)F)c1C]

Preparation of 2-methyl-3-(2-methyl-3-(trifluoromethyl)benzyl)-5-(tetrahydro-2H-pyran-4-yl)pyrazolo[1,5-a]pyrimidine a) 2-methyl-3-{[2-methyl-3-(trifluoromethyl)phenyl]methyl}-5-(tetrahydro-2H-pyran-4-yl)pyrazolo[1,5-a]pyrimidin-7(4H)-one

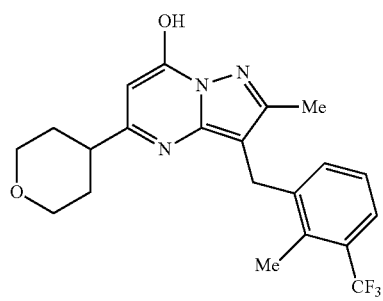

To a suspension of ethyl 3-oxo-3-(tetrahydro-2H-pyran-4-yl)propanoate (0.78 mg, 3.90 mmol) in acetic acid was added 3-methyl-4-{[2-methyl-3-(trifluoromethyl)phenyl]methyl}-1H-pyrazol-5-amine (1.0 g, 3.71 mmol) in microwave reaction vessel. It was sealed and heated with microwave reactor at 140° C. for 40 minutes. The reaction mixture was cooled, diluted with acetic acid (5 mL) and stood for overnight. Precipitate was observed, filtered. Solid was washed with acetic acid (2 mL) and cooled methanol (2 mL). Solid was dried. The b): 7-chloro-2-methyl-3-{[2-methyl-3-(trifluoromethyl)phenyl]methyl}-5-(tetrahydro-2H-pyran-4-yl)pyrazolo[1,5-a]pyrimidine

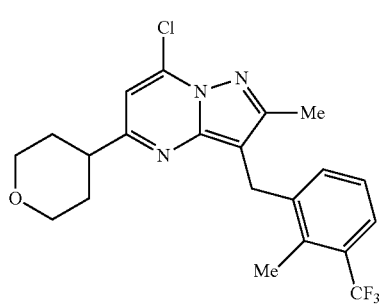 [SMILES: Cc1nn2c(Cl)cc(C3CCOCC3)nc2c1Cc1cccc(C(F)(F)F)c1C]

To a suspension of N,N-diethylaniline (0.83 g, 5.54 mmol) and 2-methyl-3-{[2-methyl-3-(trifluoromethyl)phenyl]methyl}-5-(tetrahydro-2H-pyran-4-yl)pyrazolo[1,5-a]pyrimidin-7(4H)-one (1.02 g, 2.52 mmol) stirred under nitrogen at 0° C. was added neat phosphoric trichloride (1.93 g, 12.6 mmol) dropwise during 5 minutes. The reaction mixture was stirred at 80° C. for 2 hr. Reaction mixture was concentrated. The residue was dissolved with DCM (50 mL) and icy water (15 mL). The pH of aqueous layer was adjusted by 10 N NaOH solution to 5. Two layers were separated. Organic layer was washed with brine (15 mL) again. Organic layer was dried, concentrated to dryness. Product was purified on a silica gel column (ethyl acetate/hexane gradient solvents). The product was obtained and used in subsequent steps. (463 mg, 43%); LC/MS: MS (ES+) m/e 424 (MH+).

c): Preparation of 2-methyl-3-(2-methyl-3-(trifluoromethyl)benzyl)-5-(tetrahydro-2H-pyran-4-yl)pyrazolo[1,5-a]pyrimidine To a suspension of 7-chloro-2-methyl-3-{[2-methyl-3-(trifluoromethyl)phenyl]methyl}-5-(tetrahydro-2H-pyran-4-yl)pyrazolo[1,5-a]pyrimidine (85 mg, 0.201 mmol) in ethanol (2 mL) and 1,4-dioxane (2 mL) were added hexaformylmolybdenum (27.1 mg, 0.100 mmol), Pd/C (1.0 mg, mmol) and DMAP (49 mg, 0.4 mmol) and diisopropylethylamine (26 mg, 0.2 mmol). The reaction mixture was irradiated (microwave) and stirred at 150° C. for 15 minutes. Reaction mixture was cooled down, diluted with ethyl acetate (30 mL) and 5% HCl solution. Two layers were separated. Organic layer was dried and concentrated to dryness. The crude product was purified to yield the titled compound (16 mg, 21%); LC/MS: MS (ES+) m/e 390 (MH+); 1H NMR (400 MHz, DMSO-d6) δ ppm 1.70-1.81 (m, 4H) 2.28 (s, 3H) 2.45-2.49 (m, 3H) 2.96 (s, 1H) 3.37-3.47 (m, 3H) 3.92 (br. s., 2H) 4.10 (s, 2H) 6.89 (d, J=7.33 Hz, 1H) 7.34 (s, 1H) 7.52 (s, 1H) 8.86 (d, J=7.33 Hz, 1H).

Example 6

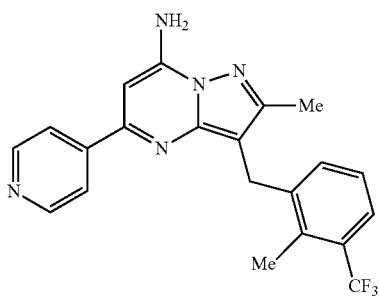 [SMILES: Cc1nn2c(N)cc(-c3ccncc3)nc2c1Cc1cccc(C(F)(F)F)c1C]

Preparation of 2-methyl-3-(2-methyl-3-(trifluoromethyl)benzyl)-5-(pyridin-4-yl)pyrazolo[1,5-a]pyrimidin-7-amine To a suspension of 3-methyl-4-{[2-methyl-3-(trifluoromethyl)phenyl]methyl}-1H-pyrazol-5-amine (100 mg, 0.37 mmol) in acetic acid (2 mL) was added 3-oxo-3-(4-pyridinyl)propanenitrile (54.3 mg, 0.37 mmol). The reaction mixture was irradiated (microwave) and stirred at 140° C. for 40 minutes. Reaction mixture was cooled down, diluted with acetic acid (2 mL) and stood still overnight. Precipitate was collected by filtration. The crude product was purified with column chromatography to provide titled product. (23 mg, 16%); LC/MS: MS (ES+) m/e 398 (MH+); 1H NMR (400 MHz, DMSO-d6) δ ppm 1.57 (s, 3H) 1.72 (s, 3H) 3.44 (s, 2H) 6.01 (s, 1H) 6.45 (d, J=7.58 Hz, 1H) 6.50-6.55 (m, 1H) 6.73 (d, J=7.58 Hz, 1H) 7.72-7.80 (m, 2H) 8.03-8.10 (m, 2H).

Example 7

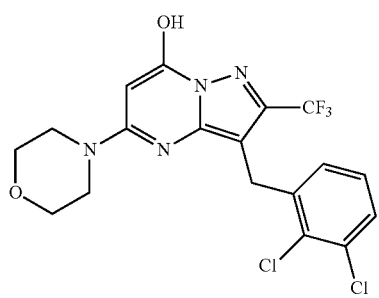 [SMILES: Oc1cc(N2CCOCC2)nc2c(Cc3cccc(Cl)c3Cl)c(C(F)(F)F)nn12]

Preparation of 3-(2,3-dichlorobenzyl)-5-morpholino-2-(trifluoromethyl)pyrazolo[1,5-a]pyrimidin-7-ol a) 5,7-dichloro-3-[(2,3-dichlorophenyl)methyl]-2-(trifluoromethyl)pyrazolo[1,5-a]pyrimidine

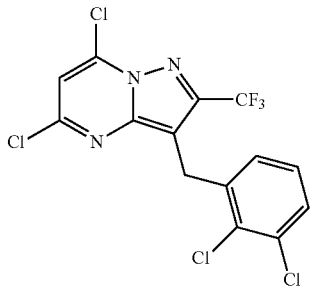 [SMILES: FC(F)(F)c1nn2c(Cl)cc(Cl)nc2c1Cc1cccc(Cl)c1Cl]

Into a suspension of 3-[(2,3-dichlorophenyl)methyl]-2-(trifluoromethyl)pyrazolo[1,5-a]pyrimidine-5,7(4H,6H)-dione (1.61 g, 4.26 mmol), prepared using similar methods to that used for the preparation of Example 1 step b, stirred under N₂ at 0° C. was added neat phosphoric trichloride (3.26 g, 21 mmol) dropwise during 5 min. The reaction mixture was stirred at 110° C. for 5 hrs. Reaction mixture was concentrated. The residue was dissolved with DCM (100 mL) and icy water (20 mL). The pH of aqueous layer was adjusted with 10 N NaOH solution to pH ~8. Two layers were separated. Aqueous layer was extracted with DCM (60 mL) again. Combined organic layers were dried and concentrated to dryness. Crude product was purified with silica gel column (ethyl acetate/hexane gradient solvent system). The product was obtained and used in the next step. (0.83 g, 47%); LC/MS: MS (ES⁺) m/e 414 (MH⁺).

b) 5-chloro-3-[(2,3-dichlorophenyl)methyl]-2-(trifluoromethyl)pyrazolo[1,5-a]pyrimidin-7-ol

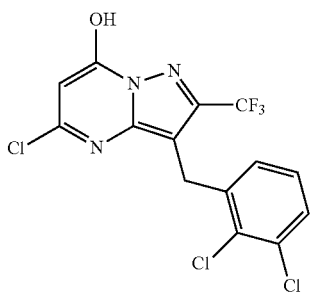 [SMILES: Oc1cc(Cl)nc2c(Cc3cccc(Cl)c3Cl)c(C(F)(F)F)nn12]

To a solution of 5,7-dichloro-3-[(2,3-dichlorophenyl)methyl]-2-(trifluoromethyl)pyrazolo[1,5-a]pyrimidine (0.83 g, 2.0 mmol) in THF (10 mL) and water (2.5 mL) was added 1.6 mL of 6N sodium hydroxide solution. Reaction mixture was stirred at 45° C. overnight. Reaction mixture was concentrated down to s small volume, and diluted with 10 mL of icy water. The pH of reaction solution was adjusted to ~7, and extracted with ethyl acetate (35 mL×2). Combined organic layers were dried over anhydrous sodium sulfate, and concentrated to dryness. The crude material was purified with column chromatography. Product was obtained and used without further purification in the next step. (0.273 g, 34%); LC/MS: MS (ES⁺) m/e 396 (MH⁺).

c) Preparation of 3-(2,3-dichlorobenzyl)-5-morpholino-2-(trifluoromethyl)pyrazolo[1,5-a]pyrimidin-7-ol To a solution of 5-chloro-3-[(2,3-dichlorophenyl)methyl]-2-(trifluoromethyl)pyrazolo[1,5-a]pyrimidin-7-ol (79 mg, 0.2 mmol) in ethanol (2 mL) was added morpholine (87 mg, 0.99 mmol) in a microwave reaction vessel. It was sealed and irradiated (microwave) at 150° C. for three hours. The reaction mixture was diluted with ethyl acetate (20 mL), washed with 5% HCl solution (5 mL). Organic layer was dried, filtered, and concentrated. The crude product was purified by reverse-phase HPLC to provide the titled compound. (28 mg, 31%); LC/MS: MS (ES⁺) m/e 447 (MH⁺); ¹H NMR (400 MHz, DMSO-d₆) δ ppm 3.35 (br. s., 4H) 3.65-3.75 (m, 4H) 4.19 (s, 2H) 5.22 (s, 1H) 6.84 (s, 1H) 7.25 (t, J=7.96 Hz, 1H) 7.52 (s, 1H) 11.28 (s, 1H).

Example 8

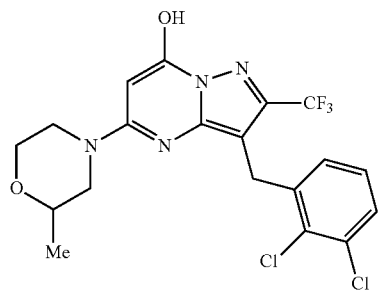 [SMILES: CC1CN(c2cc(O)n3nc(C(F)(F)F)c(Cc4cccc(Cl)c4Cl)c3n2)CCO1]

Preparation of 3-(2,3-dichlorobenzyl)-5-(2-methylmorpholino)-2-(trifluoromethyl)pyrazolo[1,5-a]pyrimidin-7-ol To a solution of 5-chloro-3-[(2,3-dichlorophenyl)methyl]-2-(trifluoromethyl)pyrazolo[1,5-a]pyrimidin-7-ol (79 mg, 0.2 mmol), prepared as described in Example 7 step b, in ethanol (2 mL) was added 2-methylmorpholine (101 mg, 1.0 mmol) in a microwave reaction vessel. It was sealed and irradiated (microwave) at 150° C. for seven hours. The reaction mixture was diluted with ethyl acetate (20 mL), washed with 5% HCl solution (5 mL). Organic layer was dried, filtered, and concentrated. The crude product was purified by reverse-phase HPLC to provide the titled compound. (17 mg, 18%); LC/MS: MS (ES⁺) m/e 461 (MH⁺); ¹H NMR (400 MHz, DMSO-d₆) δ ppm 1.13 (d, J=6.32 Hz, 3H) 2.68 (m, 1H)

2.96 (m, 1H) 3.56 (m, 2H) 3.71 (m, 2H) 3.88 (m, 1H) 4.20 (s, 2H) 5.23 (s, 1H) 6.85 (s, 1H) 7.25 (t, J=7.96 Hz, 1H) 7.53 (d, J=7.58 Hz, 1H) 11.24 (s, 1H).

Example 9

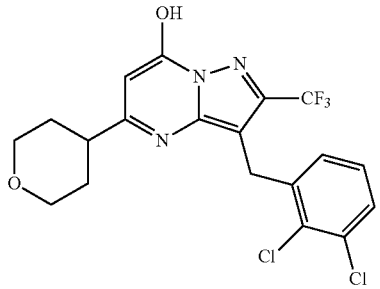 [SMILES: Oc1cc(C2CCOCC2)nc2c(Cc3cccc(Cl)c3Cl)c(C(F)(F)F)nn12]

Preparation of 3-(2,3-dichlorobenzyl)-5-(tetrahydro-2H-pyran-4-yl)-2-(trifluoromethyl)pyrazolo[1,5-a]pyrimidin-7-ol To a suspension of 4-[(2,3-dichlorophenyl)methyl]-5-(trifluoromethyl)-1H-pyrazol-3-amine TFA salt (201 mg, 0.48 mmol) in acetic acid (2 mL) was added ethyl 3-oxo-3-(tetrahydro-2H-pyran-4-yl)propanoate (100 mg, 0.50 mmol). The reaction vessel was sealed, stirred and irradiated (microwave) at 140° C. for 40 minutes. The reaction mixture was cooled and diluted with acetic acid (5 mL). It was stood still overnight. The precipitate was collected, washed with acetic acid (2 mL), then with cooled methanol (2 mL) and dried to give crude product. The crude material was purified by reverse-phase HPLC to provide titled compound. (16 mg, 7.5%); LC/MS: MS (ES$^+$) m/e 446 (MH$^+$); $^1$H NMR (400 MHz, DMSO-d$_6$) δ ppm 1.75-1.77 (m, 4H) 2.82 (s, 1H) 3.38-3.41 (m, 2H) 3.96 (dd, J=10.99, 2.91 Hz, 2H) 4.21 (s, 2H) 5.84 (s, 1H) 6.77-6.83 (m, 1H) 7.25 (t, J=7.96 Hz, 1H) 7.54 (dd, J=7.96, 1.39 Hz, 1H) 12.22 (s, 1H).

Example 10

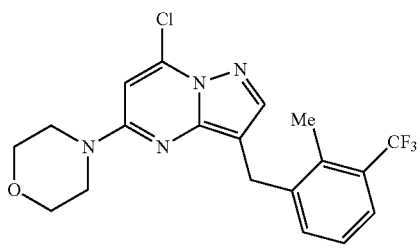 [SMILES: Cc1c(Cc2cnn3c(Cl)cc(N4CCOCC4)nc23)cccc1C(F)(F)F]

Preparation of 3-(2-methyl-3-(trifluoromethyl)benzyl)-5-morpholinopyrazolo[1,5-a]pyrimidin-7-ol a) (2E)-2-[bis(methyloxy)methyl]-3-[2-methyl-3-(trifluoromethyl)phenyl]-2-propenenitrile

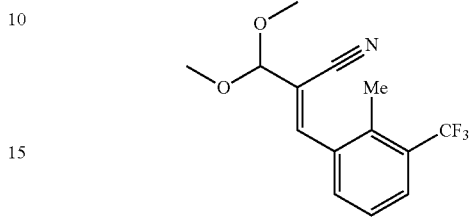

To a solution of 2-methyl-3-(trifluoromethyl)benzaldehyde (3.0 g, 16 mmol) and 3,3-bis(ethyloxy)propanenitrile (2.3 g, 20 mmol) in methanol (10 mL) was added a 25% sodium methoxide in methanol over 20 minutes. The mixture was stirred at room temperature overnight. Most of solvent was evaporated in vacuo and the residue was dissolved with ethyl acetate (30 mL) and water (15 mL). Two layers were separated. Organic layer was separated, washed with brine (15 mL), dried and solvent was evaporated in vacuo. The residue was then purified to give product. (3.66 g, 64%); 1H NMR (400 MHz, DMSO-d$_6$) δ ppm 2.40 (s, 3H) 2.94 (m, J=11.37 Hz, 1H) 3.08 (m, J=4.80 Hz, 1H) 3.20 (s, 1H) 3.43 (d, J=10.36 Hz, 1H) 3.42 (d, J=11.12 Hz, 6H) 3.45-3.52 (m, 1H) 4.60 (d, J=4.80 Hz, 1H) 7.39 (t, J=7.71 Hz, 1H) 7.59 (dd, J=17.18, 7.83 Hz, 2H).

b) 4-{[2-methyl-3-(trifluoromethyl)phenyl]methyl}-1H-pyrazol-3-amine

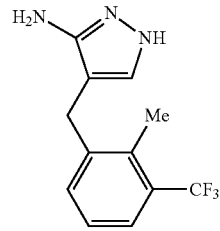 [SMILES: Cc1c(Cc2c[nH]nc2N)cccc1C(F)(F)F]

The suspension of (2E)-2-[bis(methyloxy)methyl]-3-[2-methyl-3-(trifluoromethyl)phenyl]-2-propenenitrile (2.62 g, 9.2 mmol) and 10% Pd/C (49 mg, 0.046 mmol) in methanol (25 mL) was hydrogenated using the Patt shaker (23° C., 50 bar) overnight. The catalyst was removed by filtration. Concentration of filtrate gave desired product. (2.41 g, 91%). To a solution of 3,3-bis(methyloxy)-2-{[2-methyl-3-(trifluoromethyl)phenyl]methyl}propanenitrile (2.41 g, 8.39 mmol), hydrazine monohydrate (2.12 g, 41.9 mmol) in ethanol (15 mL) was added a conc. HCl solution (6.89 g, 67.1 mmol) dropwise. The reaction mixture was stirred at 100° C. for 3 hours. Most of the solvent was evaporated in vacuo and the residue was dissolved with ethyl acetate (30 mL) and water (15 mL). The two layers were separated. Organic layer was washed with brine (15 mL), dried (MgSO4) and concentrated to dryness in vacuo. The residue was then purified column chromatography (methanol/DCM) to give product. (1.71 g, 80%); LC/MS: MS (ES⁺) m/e 256 (MH⁺).

c) 3-{[2-methyl-3-(trifluoromethyl)phenyl]methyl}pyrazolo[1,5-a]pyrimidine-5,7(4H,6H)-dione

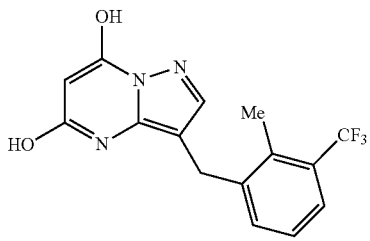 [SMILES: Cc1c(Cc2cnn3c(O)cc(O)nc23)cccc1C(F)(F)F]

To a solution of 4-{[2-methyl-3-(trifluoromethyl)phenyl]methyl}-1H-pyrazol-3-amine (1.71 g, 6.7 mmol) in methanol (10 mL) was added dimethyl malonate (0.93 g, 7.0 mmol), followed by adding a 25% sodium methoxide solution (2.95 g, 13.40 mmol). The reaction vessel was sealed and irradiated (microwave) to 125° C. for 45 minutes. After the reaction mixture was cooled, precipitate was collected by filtration. The solid was washed with cooled methanol (5 mL×2). Product was dried under air. The product was then suspended with 1 N HCl (30 mL), stirred for 10 minutes. Product was obtained by filtration. It was dried under vacuum oven and was used in next step. (2.13 g, 98%). LC/MS: MS (ES⁺) m/e 324 (MH⁺)

d) 5,7-dichloro-3-{[2-methyl-3-(trifluoromethyl)phenyl]methyl}pyrazolo[1,5-a]pyrimidine

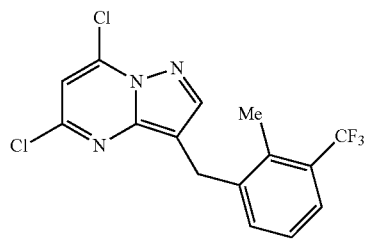 [SMILES: Cc1c(Cc2cnn3c(Cl)cc(Cl)nc23)cccc1C(F)(F)F]

To a suspension of 3-{[2-methyl-3-(trifluoromethyl)phenyl]methyl}pyrazolo[1,5-a]pyrimidine-5,7(4H,6H)-dione (2.1 g, 6.5 mmol), and N,N-diethylaniline (2.13 g, 14.3 mmol) stirred under nitrogen at 0° C. was added neat phosphoric trichloride (10 g, 65 mmol) in dropwise during 5 min. The reaction mixture was stirred at 110° C. for 5 hrs. Reaction mixture was concentrated. The residue was dissolved with DCM (100 mL) and icy water (20 mL). The pH of aqueous layer was adjusted with 10 N NaOH solution to pH ~8. Two layers were separated. Aqueous Layer was extracted with DCM (60 mL) again. Combined organic layers were dried, and concentrated to dryness. Crude product was then purified with silica gel column (ethyl acetate/hexane gradient solvent). Product was obtained and used in next step. (1.91 g, 82%); LC/MS: MS (ES⁺) m/e 360 (MH⁺).

e) 3-(2-methyl-3-(trifluoromethyl)benzyl)-5-morpholinopyrazolo[1,5-a]pyrimidin-7-ol

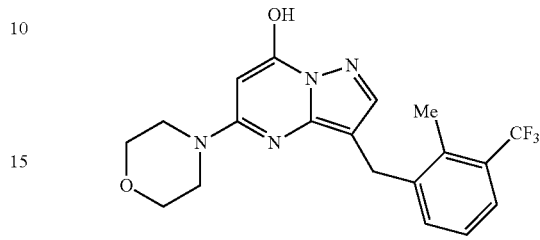

To a solution of 5,7-dichloro-3-{[2-methyl-3-(trifluoromethyl)phenyl]methyl}pyrazolo[1,5-a]pyrimidine (1.9 g, 5.28 mmol) in water (10.0 mL) and tetrahydrofuran (40 mL) stirred at 0° C. was added a solution of 1M NaOH solution (5.28 g, 13.2 mmol) in dropwise during 5 min. The reaction mixture was stirred at 40° C. for 1 hour. Excess solvent was removed. The residue was dissolved with ethyl acetate (100 mL) and water (25 mL). The pH of aqueous layer was adjusted to pH 7. Two layers were separated. Aqueous Layer was extracted with ethyl acetate (50 mL×2). Combined layers were dried and concentrated to dryness. The product was obtained and used in next step. (1.64 g, 91%); LC/MS: MS (ES⁺) m/e 342 (MH⁺). To a solution of 5-chloro-3-{[2-methyl-3-(trifluoromethyl)phenyl]methyl}pyrazolo[1,5-a]pyrimidin-7(4H)-one (1.21 g, 3.54 mmol) in ethanol (3 mL) stirred under nitrogen at 20° C. was added neat morpholine (0.925 g, 10.62 mmol). The reaction vessel was sealed and irradiated (microwave) at 145° C. for 4 hr. Reaction mixture diluted with ethyl acetate (50 mL) and water (15 mL). The pH of aqueous layer was adjusted with conc. HCl solution to 5. Two layers were separated. Aqueous layer was extracted with ethyl acetate (50 mL) again. Combined layers were dried and concentrated. The crude material was then purified with column chromatography (silica gel, CH3OH/DCM 0-10%). Desired product was obtained and used in next step. (520 mg, 37%); LC/MS: MS (ES⁺) m/e 393 (MH⁺).

f) 4-(7-chloro-3-(2-methyl-3-(trifluoromethyl)benzyl)pyrazolo[1,5-a]pyrimidin-5-yl)morpholine To a suspension of 3-{[2-methyl-3-(trifluoromethyl)phenyl]methyl}-5-(4-morpholinyl)pyrazolo[1,5-a]pyrimidin-7(4H)-one (0.52 g, 1.32 mmol) and N,N-diethylaniline (0.43 g, 2.92 mmol) under nitrogen was added neat phosphoric trichloride (1.12, 6.63 mmol) dropwise during 15 minutes. The reaction mixture was stirred at 80° C. for 3 hours. Reaction mixture was concentrated under reduce pressure. The residue was dissolved with DCM (50 mL) and water (15 mL). The pH of aqueous layer was adjusted to 8~9. Two layers were separated. Aqueous layer was then extracted with DCM (30 mL×3). The crude material was then purified with silica gel column chromatography (CH3OH/DCM 0-10%) to provide the titled product. (450 mg, 83%); LC/MS: MS (ES⁺) m/e 378 (MH⁺); ¹H NMR (400 MHz, DMSO-d₆) δ ppm 3.43 (br. s., 1H) 3.45 (d, J=5.05 Hz, 3H) 3.63-3.71 (m, 4H) 4.00 (s, 2H) 5.55 (s, 1H) 7.16 (s, 2H) 7.22-7.30 (m, 1H) 7.30-7.40 (m, 1H) 7.46 (dd, J=7.83, 1.77 Hz, 1H) 7.72 (s, 1H).

Example 11

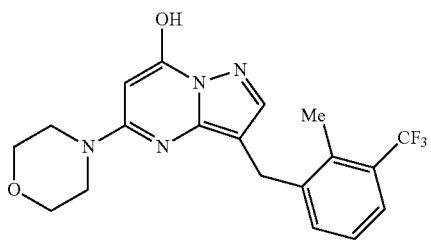 [SMILES: Cc1c(Cc2cnn3c(O)cc(N4CCOCC4)nc23)cccc1C(F)(F)F]

Preparation of 3-(2-methyl-3-(trifluoromethyl)benzyl)-5-morpholinopyrazolo[1,5-a]pyrimidin-7-ol a) 5-chloro-7-(methyloxy)-3-{[2-methyl-3-(trifluoromethyl)phenyl]methyl}pyrazolo[1,5-a]pyrimidine

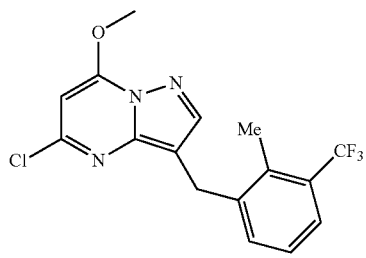 [SMILES: COc1cc(Cl)nc2c(Cc3cccc(C(F)(F)F)c3C)cnn12]

To a solution of 5,7-dichloro-3-{[2-methyl-3-(trifluoromethyl)phenyl]methyl}pyrazolo[1,5-a]pyrimidine (247 mg, 0.69 mmol) in methanol (2 ml) stirred under nitrogen at room temp was added a 25% sodium methoxide solution in methanol (163 mg, 0.75 mmol) dropwise. The reaction mixture was stirred at 25° C. for 30 minutes. Reaction mixture was diluted ethyl acetate (30 mL) and 5% HCl (10 mL). Two layers were separated. Organic layer was dried and concentrated. The titled product was obtained and used in next step. (193 mg, 79%); LC/MS: MS (ES$^+$) m/e 356 (MH$^+$).

b) Preparation of 3-(2-methyl-3-(trifluoromethyl)benzyl)-5-morpholinopyrazolo[1,5-a]pyrimidin-7-ol To a solution of 5-chloro-7-methoxy-3-(2-methyl-3-(trifluoromethyl)benzyl)pyrazol-[1,5-a]pyrimidine (190 mg, 0.53 mmol) in ethanol (2.5 mL) was added morpholine (233 mg, 2.7 mmol). It was sealed and irradiated (microwave) at 145° C. for one hour. Reaction mixture was cooled, concentrated and redissolved with ethyl acetate (30 mL), washed with 5% HCl solution (5 mL×2). Organic layer was concentrated. The crude product was purified by ISCO column system (eluted with methanol/DCM, 0-10% gradient solvent). Fractions were collected, concentrated and dried to provide the titled product. (48 mg, 23%); LC/MS: MS (ES$^+$) m/e 393 (MH$^+$); 1H NMR (600 MHz, DMSO-d6) δ ppm 2.45 (s, 3H) 3.32 (br. s., 4H) 3.64 (t, J=4.91 Hz, 4H) 3.84 (s, 2H) 4.85 (s, 1H) 7.27 (t, J=3.97 Hz, 2H) 7.47 (d, 1H) 7.54 (d, J=7.93 Hz, 1H);

Example 12

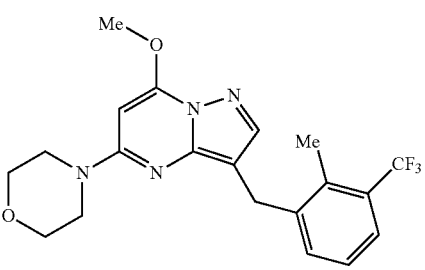 [SMILES: COc1cc(N2CCOCC2)nc2c(Cc3cccc(C(F)(F)F)c3C)cnn12]

Preparation of 4-(7-methoxy-3-(2-methyl-3-(trifluoromethyl)benzyl)pyrazolo[1,5-a]pyrimidin-5-yl)morpholine To a solution of 4-(7-chloro-3-(2-methyl-3-(trifluoromethyl)benzyl)pyrazolo[1,5-a]pyrimidin-5-yl)morpholine (181 mg, 0.44 mmol) in methanol (5 mL) stirred under nitrogen at 0° C. was added a 33% solution of sodium methoxide in dropwise. The reaction mixture was stirred at 40° C. for 1 hour. Solvent was removed in vacuo. The residue was dissolved with ethyl acetate (30 mL) and water (10 mL). Two layers were separated. Organic layer was dried and concentrated. The crude product was purified by reverse-phase HPLC to provide the titled compound. (15 mg, 8.4%); LC/MS: MS (ES$^+$) m/e 407 (MH$^+$); $^1$H NMR (400 MHz, DMSO-d$_6$) δ ppm 2.39-2.47 (m, 3H) 3.60 (br. s., 2H) 3.61 (d, J=4.55 Hz, 2H) 3.65-3.73 (m, 4H).

Example 13

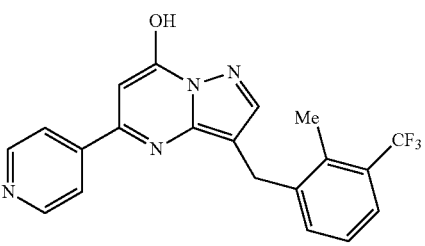 [SMILES: Cc1c(Cc2cnn3c(O)cc(-c4ccncc4)nc23)cccc1C(F)(F)F]

Preparation of 3-(2-methyl-3-(trifluoromethyl)benzyl)-5-(pyridin-4-yl)pyrazolo[1,5-a]pyrimidin-7-ol To a solution of 4-{[2-methyl-3-(trifluoromethyl)phenyl]methyl}-1H-pyrazol-3-amine (115 mg, 0.45 mmol) in acetic acid (2.0 mL) was added ethyl 3-oxo-3-(4-pyridinyl)propanoate (87 mg, 0.45 mmol) in a microwave reaction vessel. It was sealed and irradiated (microwave) at 140° C. for 60 minutes. The reaction mixture was cooled and stood for 2 hours. Precipitate was observed, filtered. Solid was washed with acetic acid (1 mL), then ethanol (1 mL×2). Solid was dried. The titled compound was obtained. (87 mg, 50%); LC/MS: MS (ES$^+$) m/e 385 (MH$^+$); 1H NMR (400 MHz, DMSO-d$_6$) δ ppm 2.44 (s, 3H) 4.12 (s, 2H) 6.14 (s, 1H) 7.34

(s, 2H) 7.56 (d, J=9.09 Hz, 1H) 7.67 (s, 1H) 7.81 (br. s., 2H) 8.78 (br. s., 2H) 12.37 (br. s., 1H).

Example 14

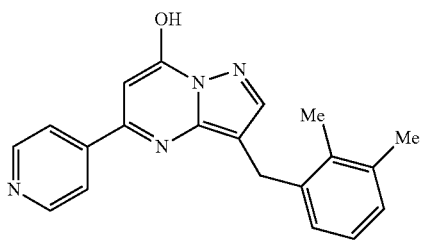 [SMILES: Cc1cccc(Cc2cnn3c(O)cc(-c4ccncc4)nc23)c1C]

Preparation of 3-(2,3-dimethylbenzyl)-5-(pyridin-4-yl)pyrazolo[1,5-a]pyrimidin-7-ol a) (2E)-2-[bis(methyloxy)methyl]-3-(2,3-dimethylphenyl)-2-propenenitrile

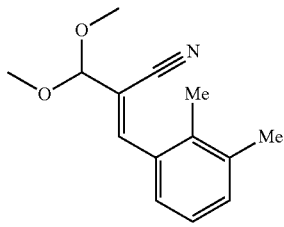 [SMILES: COC(OC)/C(C#N)=C/c1cccc(C)c1C]

To a solution of 3,3-bis(ethyloxy)propanenitrile (2.3 g, 20 mmol) and 2,3-dimethylbenzaldehyde (2.1 g, 16 mmol) in methanol (10 mL) was added a 25-30% of sodium methoxide in methanol over 20 minutes. The reaction mixture was stirred at room temperature overnight. Most of solvent was evaporated in vacuo and the residue was dissolved with ethyl acetate (30 mL) and water (15 mL). The two layers were separated. Organic layer was separated, washed with brine (15 mL), dried and concentrated in vacuo. The residue was then purified to give product. It was used in next step. (1.55 g, 33%); 1H NMR (600 MHz, DMSO-d6) δ ppm 2.20 (s, 3H) 2.28 (s, 3H) 3.37 (s, 6H) 5.13 (s, 1H) 7.17-7.22 (m, 1H) 7.27 (d, J=7.55 Hz, 1H) 7.39-7.45 (m, 1H) 7.79 (s, 1H).

b) 4-(2,3-dimethylbenzyl)-1H-pyrazol-3-amine

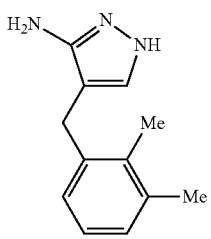 [SMILES: Cc1cccc(Cc2c[nH]nc2N)c1C]

The suspension of (2E)-2-[bis(methyloxy)methyl]-3-(2,3-dimethylphenyl)-2-propenenitrile (1.55 g, 9.2 mmol) and 10% Pd/C (36 mg, 0.33 mmol) in methanol (25 mL) was hydrogenated using the Parr shaker (23° C., 50 bar) overnight. The catalyst was removed by filtration. Concentration of filtrate gave desire product. (0.26 g, 17%). To a solution of 2-[(2,3-dimethylphenyl)methyl]-3,3-bis(methyloxy)propanenitrile (257 mg, 1.1 mmol) and hydrazine monohydrate (55.1 mg, 1.1 mmol) in ethanol (15 ml) stirred under nitrogen at room temperature was added a solution of 36% HCl (558 mg, 5.51 mmol) dropwise. The reaction mixture was stirred at 100° C. for overnight. Reaction mixture was concentrated and dissolved with ethyl acetate (30 mL) and water (10 mL). pH of aqueous layer was adjusted to 8~9. Two layers were separated. Organic layer was washed with brine (5 mL), dried and concentrated. Crude product was purified with silica gel column (0-10 methanol/DCM). Product was obtained and used in next step. (191 mg, 86%); LC/MS: MS (ES+) m/e 202 (MH+).

c) Preparation of 3-(2,3-dimethylbenzyl)-5-(pyridin-4-yl)pyrazolo[1,5-a]pyrimidin-7-ol To a solution of 4-(2,3-dimethylbenzyl)-1H-pyrazol-3-amine (189 mg, 0.93 mmol) in acetic acid (2.0 mL) was added ethyl 3-oxo-3-(4-pyridinyl)propanoate (185 mg, 0.96 mmol) in a microwave reaction vessel. It was sealed and irradiated (microwave) at 140° C. for 60 minutes. The reaction mixture was cooled and stood for 2 hours. Precipitate was observed, filtered. Solid was washed with acetic acid (1 mL), then ethanol (1 mL×2). Solid was dried. The titled compound was obtained. (107 mg, 34%); LC/MS: MS (ES+) m/e 331 (MH+); 1H NMR (400 MHz, DMSO-d6) δ ppm 2.20 (s, 3H) 2.26 (s, 3H) 4.02 (s, 2H) 6.12 (s, 1H) 6.98-7.06 (m, 3H) 7.56 (s, 1H) 7.82 (br. s., 1H) 7.81 (d, J=5.31 Hz, 1H) 8.80 (dd, J=4.55, 1.52 Hz, 2H) 12.37 (br. s., 1H).

Example 15

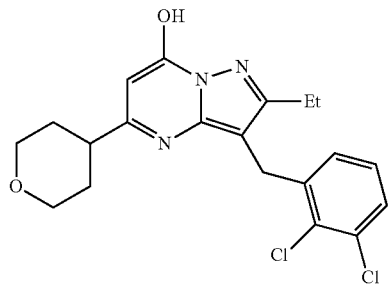 [SMILES: CCc1nn2c(O)cc(C3CCOCC3)nc2c1Cc1cccc(Cl)c1Cl]

Preparation of 3-(2,3-dichlorobenzyl)-2-ethyl-5-(tetrahydro-2H-pyran-4-yl)pyrazolo[1,5-a]pyrimidin-7-ol To a suspension of 4-[(2,3-dichlorophenyl)methyl]-3-ethyl-1H-pyrazol-5-amine (257 mg, 0.95 mmol) in acetic acid (2 mL) was added ethyl 3-oxo-3-(tetrahydro-2H-pyran-4-yl)propanoate (200, 1.0 mmol). The reaction vessel was sealed, stirred and irradiated (microwave) at 140° C. for 40 minutes. Reaction mixture was cooled and diluted with acetic acid (2 mL). It was stood still overnight. The precipitate was collected, washed with acetic acid (1 mL), then with methanol (2 mL×2) and dried to afford expected compound. (288 mg, 71%); LC/MS: MS (ES+) m/e 406 (MH+); 1H NMR (400 MHz, DMSO-d6) δ ppm 1.06 (t, J=7.45 Hz, 3H) 1.76 (br. s., 4H) 1.91 (s, 3H) 2.45 (q, J=7.41 Hz, 2H) 3.39 (br. s., 2H) 4.07 (s, 2H) 5.56 (s, 1H) 6.87 (s, 1H) 7.25 (s, 1H) 7.51 (s, 1H).

Example 16

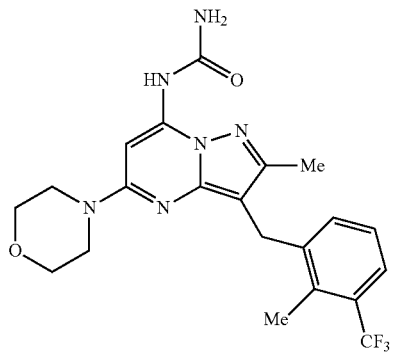 [SMILES: Cc1nn2c(NC(N)=O)cc(N3CCOCC3)nc2c1Cc1cccc(C(F)(F)F)c1C]

Preparation of 1-(2-methyl-3-(2-methyl-3-(trifluoromethyl)benzyl)-5-morpholinopyrazolo[1,5-a]pyrimidin-7-yl)urea a) 5-chloro-2-methyl-3-{[2-methyl-3-(trifluoromethyl)phenyl]methyl}pyrazolo[1,5-a]pyrimidin-7-amine

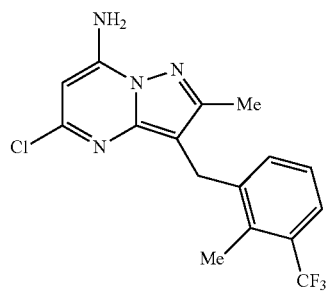 [SMILES: Cc1nn2c(N)cc(Cl)nc2c1Cc1cccc(C(F)(F)F)c1C]

To a suspension of 5,7-dichloro-2-methyl-3-{[2-methyl-3-(trifluoromethyl)phenyl]methyl}pyrazolo[1,5-a]pyrimidine (374 mg, 1.0 mmol), prepared as described in Example 1 step c, and 30% ammonium hydroxide solution (584 mg, 5.0 mmol) in 1,4-dioxane (5 mL) stirred at 20° C. for 30 hours. Reaction mixture was concentrated in vacuo. The residue was dissolved with ethyl acetate (50 mL) and 5 NaHCO3 solution (10 mL). Organic layer was separated, washed with brine (5 mL) and dried. Crude product was purified on silica gel column chromatography (methanol and DCM, 0-10%). Fractions were collected and concentrated to afford the titled product, which was in next step. (331 mg, 93%); LC/MS: MS (ES⁺) m/e 355 (MH⁺).

b) 2-methyl-3-{[2-methyl-3-(trifluoromethyl)phenyl]methyl}-5-(4-morpholinyl)pyrazolo[1,5-a]pyrimidin-7-amine

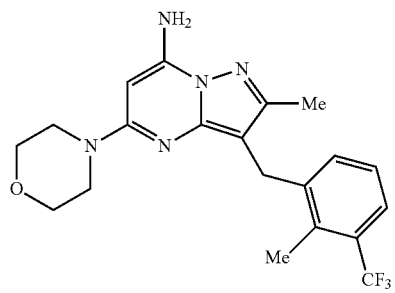 [SMILES: Cc1nn2c(N)cc(N3CCOCC3)nc2c1Cc1cccc(C(F)(F)F)c1C]

To a solution of 5-chloro-2-methyl-3-{[2-methyl-3-(trifluoromethyl)phenyl]methyl}pyrazolo[1,5-a]pyrimidin-7-amine (331 mg, 0.93 mmol) in ethanol (2 mL) was added morpholine (406 mg, 4.7 mmol). Reaction mixture was heated in microwave reactor at 140° C. for 7 hours. Reaction mixture was concentrated to dryness. It was diluted with ethyl acetate (30 mL) and 5% HCl solution (5 mL). Two layers were separated. Organic layer was dried and concentrated to dryness. Product was obtained and used in next step. (270 mg, 71%); LC/MS: MS (ES⁺) m/e 406 (MH⁺).

c) Preparation of 1-(2-methyl-3-(2-methyl-3-(trifluoromethyl)benzyl)-5-morpholinopyrazolo[1,5-a]pyrimidin-7-yl)urea To a solution of 2-methyl-3-{[2-methyl-3-(trifluoromethyl)phenyl]methyl}-5-(4-morpholinyl)pyrazolo[1,5-a]pyrimidin-7-amine (270 mg, 0.67 mmol) in DCM (5 mL) cooled to 0° C. was added DMAP (448 mg, 4.0 mmol), then added with bis(trichloromethyl) carbonate (65 mg, 0.22 mmol). Reaction mixture was allowed to warm up to room temperature, stirred overnight. The reaction mixture was cooled to 0° C. again, bubbled with ammonia gas for 3 minutes. The resulted reaction mixture was stirred for 15 minutes. Reaction mixture was diluted with DCM (25 mL) and 5% HCl (5 mL). Two layers were separated. Aqueous layer was extracted with DCM (25 mL) again. Combined organic layers were dried and concentrated. The crude material was purified with reversed phase HPLC to provide titled product. (96 mg, 31%); LC/MS: MS (ES⁺) m/e 449 (MH⁺); ¹H NMR (400 MHz, DMSO-d₆) δ ppm 2.24 (s, 3H) 2.46 (s, 3H) 3.44 (br. s., 1H) 3.45 (d, J=5.05 Hz, 3H) 3.59-3.71 (m, 4H) 3.94 (s, 2H) 7.11 (s, 1H) 7.28 (d, J=7.83 Hz, 1H) 7.36 (s, 1H) 7.50 (s, 1H) 9.52 (s, 1H).

Example 17

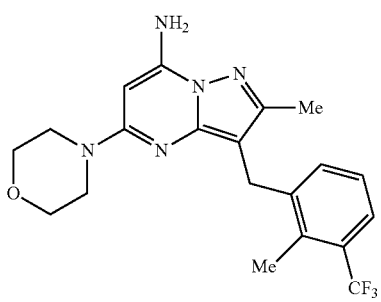

Preparation of 2-methyl-3-(2-methyl-3-(trifluoromethyl)benzyl)-5-morpholinopyrazolo[1,5-a]pyrimidin-7-amine To a suspension of 7-chloro-2-methyl-3-{{2-methyl-3-(trifluoromethyl)phenyl}methyl}-5-(4-morpholinyl)pyrazolo[1,5-a]pyrimidine (70 mg, 0.16 mmol) in methanol (2 mL) stirred under nitrogen at 0° C. was added a 2 M ammonia solution of in CH$_3$OH (0.82 mL, 1.64 mmol) dropwise. The reaction mixture was stirred at 135° C. for 3 hours. Reaction mixture was concentrated to dryness. Crude product was purified by reverse-phase HPLC to provide titled compound. (16 mg, 24%); LC/MS: MS (ES$^+$) m/e 406 (MH$^+$); 1H NMR (400 MHz, MeOD) δ ppm 2.20 (s, 3H) 2.52 (s, 3H) 3.15 (dt, J=3.28, 1.64 Hz, 1H) 3.50 (dt, J=3.28, 1.64 Hz, 1H) 3.57 (d, J=5.31 Hz, 3H) 3.55 (s, 1H) 3.82 (s, 1H) 3.81 (d, J=5.05 Hz, 3H) 4.10 (s, 2H) 5.59 (s, 1H) 7.12 (s, 1H) 7.26 (s, 1H) 7.55 (s, 1H).

Example 18

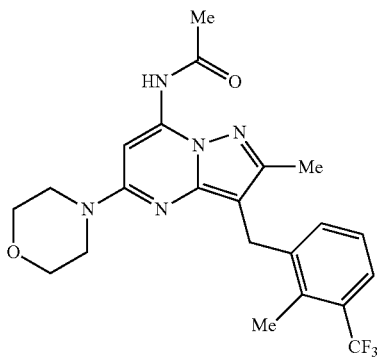 [SMILES: CC(=O)Nc1cc(N2CCOCC2)nc2c(Cc3cccc(C(F)(F)F)c3C)c(C)nn12]

Preparation of N-[2-methyl-3-{[2-methyl-3-(trifluoromethyl)phenyl]methyl}-5-(4-morpholinyl)pyrazolo[1,5-a]pyrimidin-7-yl]acetamide To a solution of 2-methyl-3-{[2-methyl-3-(trifluoromethyl)phenyl]methyl}-5-(4-morpholinyl)pyrazolo[1,5-a]pyrimidin-7-amine (120 mg, 0.3 mmol), prepared as described in Example 17, in DMF (1 mL) was added acetic anhydride (30 mg, 0.3 mmol). Reaction mixture was stirred overnight. Reaction mixture was concentrated to dryness and dissolved with DMSO (1 mL). The crude product was purified by reversed phase HPLC to provide the titled compound (15 mg, 11%); LC/MS: MS (ES$^+$) m/e 448 (MH$^+$); $^1$H NMR (400 MHz, DMSO-d$_6$) δ ppm 2.25 (s, 3H) 2.30 (s, 3H) 2.44-2.48 (m, 3H) 3.38-3.50 (m, 4H) 3.61-3.70 (m, 4H) 3.95 (s, 2H) 7.20 (s, 1H) 7.28 (d, J=7.83 Hz, 1H) 7.37 (d, J=7.07 Hz, 1H) 7.51 (d, J=7.83 Hz, 1H) 10.60 (s, 1H).

Example 19

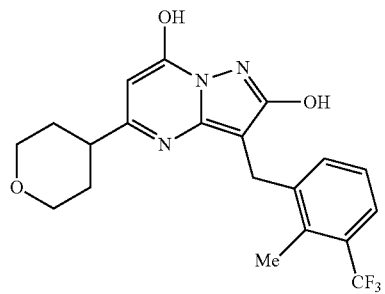

Preparation of 3-(2-methyl-3-(trifluoromethyl)benzyl)-5-(tetrahydro-2H-pyran-4-yl)pyrazolo[1,5-a]pyrimidine-2,7-diol a) methyl 2-cyano-3-[2-methyl-3-(trifluoromethyl)phenyl]propanoate

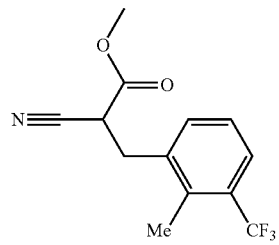 [SMILES: COC(=O)C(C#N)Cc1cccc(C(F)(F)F)c1C]

To a solution of methyl cyanoacetate in N,N-Dimethylformamide (DMF) (100 mL) stirred under nitrogen at 0° C. was added a solution of 2-methyl 3-trifluoromethylbenzylebromide (10 g, 39.5 mmol) in DMF (10 mL). The reaction mixture was stirred at 50° C. for 15 h. Then this solution was cooled to 0° C. in an ice bath. Half volume of DMF was removed. Reaction mixture was poured into 300 mL of cold icy water. Some solid was formed, filtered and collected. The filtrate was extracted with ethyl acetate (150 mL×3). Combined organic layers were dried and concentrated. The crude product was purified by silica gel column (Ethyl acetate/hexane). The titled product was obtained and used in next step. (2.2 g, 20.5%); $^1$H NMR (400 MHz, CHLOROFORM-d) δ ppm 2.49 (s, 3H) 3.26 (dd, J=14.27, 9.73 Hz, 1H) 3.48

(dd, J=14.27, 5.68 Hz, 1H) 3.71 (dd, J=9.73, 5.68 Hz, 1H) 3.86 (s, 3H) 7.30-7.36 (m, 1H) 7.46 (d, J=7.58 Hz, 1H) 7.64 (d, J=7.83 Hz, 1H).

b) 5-amino-4-{[2-methyl-3-(trifluoromethyl)phenyl]methyl}-1,2-dihydro-3H-pyrazol-3-one

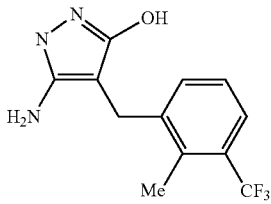

A mixture of methyl 2-cyano-3-[2-methyl-3-(trifluoromethyl)phenyl]propanoate (2.2 g, 8.1 mmol) and hydrazine monohydrate (4.1 g, 81 mmol) in ethanol (150 mL) was heated to 85° C. overnight. Reaction mixture was concentrated to dryness. The residue was redissolved with DCM (200 mL) and water (30 mL). Two layers were separated. Organic layers were dried and concentrated to dryness. Desired product was obtained and used in next step. (2.11 g, 96%); LC/MS: MS (ES$^+$) m/e 272 (MH$^+$).

c) Preparation of 3-(2-methyl-3-(trifluoromethyl)benzyl)-5-(tetrahydro-2H-pyran-4-yl)pyrazolo[1,5-a]pyrimidine-2,7-diol To a suspension of 5-amino-4-{[2-methyl-3-(trifluoromethyl)phenyl]methyl}-1,2-dihydro-3H-pyrazol-3-one (136 mg, 0.5 mmol) in ethanol (1 mL) were added ethyl 3-oxo-3-(tetrahydro-2H-pyran-4-yl)propanoate (100 mg, 0.5 mmol) and 4 M HCl solution in dioxane (25 uL, 0.1 mmol). The reaction mixture was irradiated (microwave) at 110° C. for 30 minutes. Reaction was cooled down. The precipitate was collected by filtration. It was washed with acetic acid (1 mL), then methanol (1 mL) and dried. The titled compound was obtained. (52 mg, 25%); LC/MS: MS (ES$^+$) m/e 408 (MH$^+$); $^1$H NMR (400 MHz, DMSO-d$_6$) δ ppm 1.69 (dd, J=12.51, 4.17 Hz, 1H) 1.73-1.80 (m, 3H) 2.46 (s, 3H) 2.72 (s, 1H) 3.34-3.45 (m, 2H) 3.83 (s, 2H) 3.93 (br. s., 2H) 5.51 (s, 1H) 7.15 (d, J=7.58 Hz, 1H) 7.29 (t, J=7.71 Hz, 1H) 7.54 (d, J=8.34 Hz, 1H) 11.46 (s, 1H).

Example 20

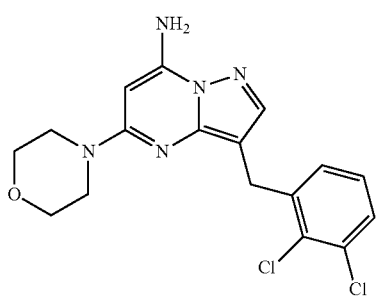 [SMILES: Nc1cc(N2CCOCC2)nc2c(Cc3cccc(Cl)c3Cl)cnn12]

Preparation of 3-(2,3-dichlorobenzyl)-5-morpholinopyrazolo[1,5-a]pyrimidin-7-amine a) 5-chloro-3-[(2,3-dichlorophenyl)methyl]pyrazolo[1,5-a]pyrimidin-7-amine

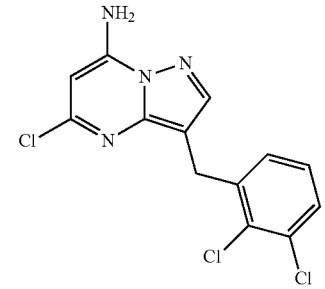 [SMILES: Nc1cc(Cl)nc2c(Cc3cccc(Cl)c3Cl)cnn12]

To a suspension of 5,7-dichloro-3-[(2,3-dichlorophenyl)methyl]pyrazolo[1,5-a]pyrimidine (2 g, 5.8 mmol), and 30% ammonium hydroxide solution (3.32 g, 28.8 mmol) in 1,4-dioxane (25 mL) stirred at 40° C. for 30 hours. Reaction mixture was concentrated in vacuo. The residue was dissolved with ethyl acetate (250 mL) and 5% NaHCO$_3$ solution (35 mL). Organic layer was separated, washed with brine (35 mL) and dried. The titled product was obtained and used for next step. (1.7 g, 90%); LC/MS: MS (ES$^+$) m/e 327 (MH$^+$).

b) Preparation of 3-(2,3-dichlorobenzyl)-5-morpholinopyrazolo[1,5-a]pyrimidin-7-amine 5-chloro-3-[(2,3-dichlorophenyl)methyl]pyrazolo[1,5-a]pyrimidin-7-amine (1.7 g, 4.43 mmol) and morpholine (1.36 g, 15.6 mmol) were mixed in ethanol (10 mL) in a microwave tube. The reaction mixture was irradiated (microwave) and stirred at 150° C. for 3 hours. Reaction mixture was dropped into cold water (100 mL) to precipitate while stirring. Precipitate was collected by filtration. It was washed with water (10 mL) and dried. The titled product was obtained. (1.90 g, 97%); LC/MS: MS (ES$^+$) m/e 378 (MH$^+$); $^1$H NMR (400 MHz, DMSO-d$_6$) δ ppm 3.43 (br. s., 1H) 3.45 (d, J=5.05 Hz, 3H) 3.63-3.71 (m, 4H) 4.00 (s, 2H) 5.55 (s, 1H) 7.16 (s, 2H) 7.22-7.30 (m, 1H) 7.30-7.40 (m, 1H) 7.46 (dd, J=7.83, 1.77 Hz, 1H) 7.72 (s, 1H).

Example 21

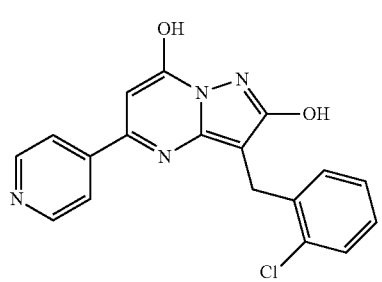 [SMILES: Oc1nn2c(O)cc(-c3ccncc3)nc2c1Cc1ccccc1Cl]

Preparation of 3-(2-chlorobenzyl)-5-(pyridin-4-yl) pyrazolo[1,5-a]pyrimidine-2,7-diol a) 5-amino-4-[(2-chlorophenyl)methyl]-1,2-dihydro-3H-pyrazol-3-one

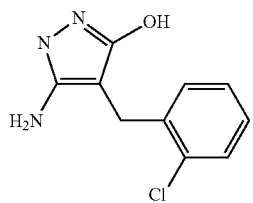 [SMILES: Nc1[nH]nc(O)c1Cc1ccccc1Cl]

To a solution of ethyl 3-(2-chlorophenyl)-2-cyanopropanoate (2.37 g, 10 mmol) in ethanol (20 mL) and acetic acid (20 mL) under nitrogen was added hydrazine monohydrate (2.5 g, 49.9 mmol). The reaction mixture was heated and stirred at 100° C. overnight. Reaction mixture was concentrated. Oily residue was dissolved with ethyl acetate (60 mL) and 5% HCl solution (15 mL). Two layers were separated. Organic layer was washed with brine (15 mL), dried and concentrated to give product. It was used in next step without purification. (1.98 g, 89%); LC/MS: MS (ES$^+$) m/e 224 (MH$^+$)

b) Preparation of 3-(2-chlorobenzyl)-2-hydroxy-5-(pyridin-4-yl)pyrazolo[1,5-a]pyrimidin-7(4H)-one To a suspension of 5-amino-4-[(2-chlorophenyl)methyl]-2,4-dihydro-3H-pyrazol-3-one (500 mg, 2.23 mmol) in acetic acid (2 mL) was added ethyl 3-oxo-3-(4-pyridinyl)propanoate (432 mg, 2.23 mmol). The reaction mixture was irradiated (microwave) and stirred at 140° C. for 60 minutes. Reaction mixture was cooled down, diluted with acetic acid (2 mL) and stood still for 2 hours. Precipitate was collected by filtration. The solid was washed with acetic acid (1 mL), ethanol (1 mL×2) and dried. The titled product was obtained. (177 mg, 22%); LC/MS: MS (ES$^+$) m/e 353 (MH$^+$); 1H NMR (400 MHz, DMSO-d$_6$) δ ppm 3.96 (s, 2H) 6.06 (d, J=1.52 Hz, 1H) 7.02 (s, 1H) 7.23 (dd, J=5.94, 3.41 Hz, 2H) 7.45 (dd, J=5.68, 3.66 Hz, 1H) 7.75 (d, J=6.06 Hz, 2H) 8.76 (d, J=6.06 Hz, 2H) 12.05 (s, 1H).

Example 22

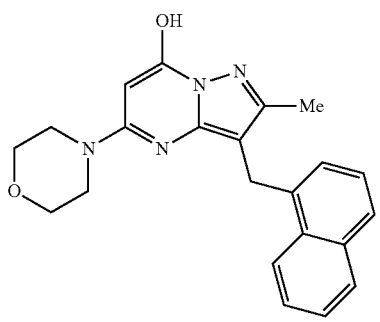 [SMILES: Cc1nn2c(O)cc(N3CCOCC3)nc2c1Cc1cccc2ccccc12]

Preparation of 2-methyl-5-morpholino-3-(naphthalen-1-ylmethyl)pyrazolo[1,5-a]pyrimidin-7-ol To a solution of 5,7-dichloro-2-methyl-3-(1-naphthalenylmethyl)pyrazolo[1,5-a]pyrimidine (0.06 g, 0.175 mmol), prepared using a similar route as was used in Example 1 step c, in Tetrahydrofuran (THF) (5 mL), was added sodium hydroxide (0.877 mL, 1.753 mmol). The reaction was stirred at rt for 18 and 50° C. for 7 h. The reaction mixture was acidified and extracted with EtOAc (80 mL×2). The organic phases were combined, dried and concentrated. To the crude mixture in ethanol (1 mL) was added morpholine (0.076 mL, 0.877 mmol). The reaction mixture was subjected to MW irradiation at 150° C. for 3 h. The reaction mixture was concentrated. The residue was purified by reverse-phase HPLC (25~55% CH3CN (0.1% TFA)/Water (0.1% TFA)) to give the product (0.02 g, 9%). $^1$H NMR (400 MHz, DMSO-d$_6$) δ ppm 2.05 (br. s., 3H) 3.30 (m, 4H) 3.67 (m, 4H) 4.37 (br. s., 2H) 5.03 (br. s., 1H) 7.01 (br. s., 1H) 7.40 (t, J=7.71 Hz, 1H) 7.56 (m, 2H) 7.79 (d, J=8.34 Hz, 1H) 7.95 (d, J=7.33 Hz, 1H) 8.27 (m, 1H); LC/MS: MS (ES+) m/e 375.1 [M+H]$^+$.

Example 23

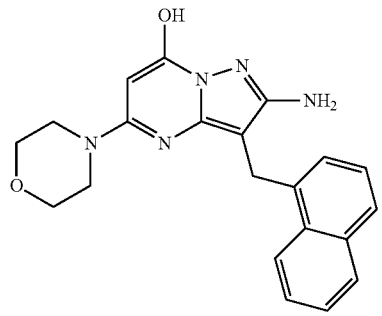 [SMILES: Nc1nn2c(O)cc(N3CCOCC3)nc2c1Cc1cccc2ccccc12]

Preparation of 2-amino-5-morpholino-3-(naphthalen-1-ylmethyl)pyrazolo[1,5-a]pyrimidin-7-ol a) 4-(1-naphthalenylmethyl)-1H-pyrazole-3,5-diamine

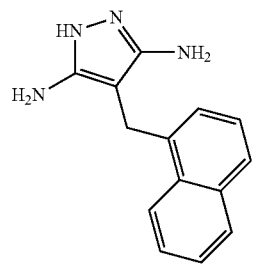 [SMILES: Nc1n[nH]c(N)c1Cc1cccc2ccccc12]

To a mixture of malononitrile (1.32 g, 20 mmol) in Ethanol (50 mL) and Water (2.50 mL) was added 1-naphthalenecarbaldehyde (3.12 g, 20 mmol). The reaction was stirred at rt for 7 days. The mixture was cooled to 0° C. in an ice bath. Sodium borohydride (0.204 g, 5.40 mmol) was introduced to the vigorously stirred mixture and the reduction was complete in about 10 min. To the reaction mixture was added water (20 mL). 1N HCl was added in to quench the excess hydride. More water was added in until precipitation was complete. Filtration gave (1-naphthalenylmethyl)propanedinitrile (3.3 g, 80%). To a solution of (1-naphthalenylmethyl)propanedinitrile (3.3 g, 16 mmol) in Ethanol (80 mL) was added hydrazine hydrate (0.785 mL, 16.00 mmol). The mixture was heated at reflux temperature for 8 h. The reaction mixture was concentrated. The crude material was purified on a silica column (MeOH/DCM: 0~10%) to give the product (2.18 g, 57%). $^1$H NMR (400 MHz, DMSO-d$_6$) δ ppm 3.96 (s, 2H) 7.26 (d, J=7.07 Hz, 1H) 7.31-7.44 (m, 1H) 7.45-7.58 (m, 2H) 7.74 (d, J=8.08 Hz, 1H) 7.85-7.97 (m, 1H) 8.12-8.26 (m, 1H) 10.05 (bs, 1H). LC/MS: MS (ES+) m/e 239.0 [M+H]$^+$.

b) 2-amino-3-(1-naphthalenylmethyl)pyrazolo[1,5-a]pyrimidine-5,7(4H,6H)-dione

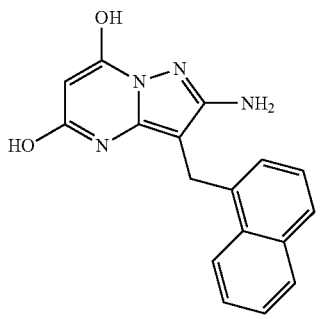 [SMILES: Nc1nn2c(O)cc(O)nc2c1Cc1cccc2ccccc12]

To a solution of 4-(1-naphthalenylmethyl)-1H-pyrazole-3,5-diamine (2.18 g, 9.15 mmol), dimethyl propanedioate (3.63 g, 27.4 mmol) in Methanol (30 mL) was added sodium methoxide (1.68 g, 31.1 mmol). The reaction mixture was stirred at 65° C. for 18 h. After the reaction mixture was cooled down, the solvent was evaporated. Water (10 mL) was added in. The solid precipitated. The mixture was neutralized with 1 N HCl. The precipitated product was filtered and dried in vacuo (2.7 g, 96%). $^1$H NMR (400 MHz, DMSO-d$_6$) δ ppm 3.65 (s, 2H) 4.21 (s, 2H) 5.59 (br. s., 2H) 7.08 (d, J=6.82 Hz, 1H) 7.27-7.45 (m, 1H) 7.48-7.66 (m, 2H) 7.79 (d, J=8.34 Hz, 1H) 7.88-8.00 (m, 1H) 8.16 (d, J=8.34 Hz, 1H) 11.34 (s, 1H). LC/MS: MS (ES+) m/e 307.0 [M+H]$^+$.

c) 2-(1,3-dioxo-1,3-dihydro-2H-isoindol-2-yl)-3-(1-naphthalenylmethyl)pyrazolo[1,5-a]pyrimidine-5,7(4H,6H)-dione

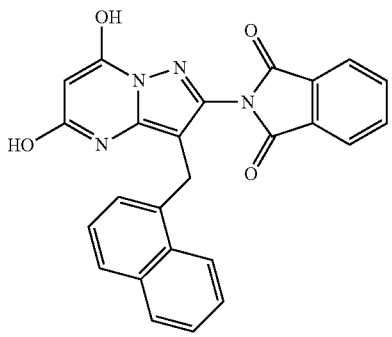 [SMILES: O=C1c2ccccc2C(=O)N1c1nn2c(O)cc(O)nc2c1Cc1cccc2ccccc12]

The solution of 2-amino-3-(1-naphthalenylmethyl)pyrazolo[1,5-a]pyrimidine-5,7(4H,6H)-dione (2.7 g, 8.81 mmol), phthalic anhydride (3.00 g, 20.27 mmol) in Acetonitrile (100 mL) was stirred at 80° C. for 2 days. Additional phthalic anhydride (3.00 g, 20.27 mmol) was added in. The reaction was stirred at 80° C. for 5 days. The reaction was concentrated. To the crude was added DCM (20 mL). The insoluble solid was collected. The filtrate was purified on a silica column (20-60% EtOAc/Hexane) which was combined with the solid from filtration to give the product (2.8 g, 71%). LC/MS: MS (ES+) m/e 437.2 [M+H]$^+$ d) 2-[5,7-dichloro-3-(1-naphthalenylmethyl)pyrazolo[1,5-a]pyrimidin-2-yl]-1H-isoindole-1,3(2H)-dione

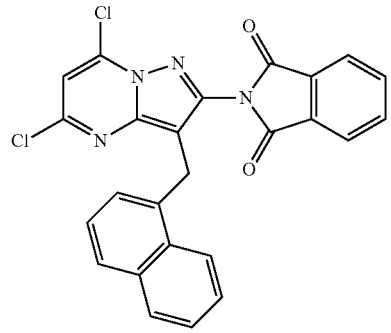 [SMILES: O=C1c2ccccc2C(=O)N1c1nn2c(Cl)cc(Cl)nc2c1Cc1cccc2ccccc12]

A mixture of 2-(1,3-dioxo-1,3-dihydro-2H-isoindol-2-yl)-3-(1-naphthalenylmethyl)pyrazolo[1,5-a]pyrimidine-5,7(4H,6H)-dione (2.8 g, 4.56 mmol) and POCl$_3$ (42.5 ml, 456 mmol) was stirred at 90° C. for 18 h. The reaction mixture was concentrated. Water (15 mL) was added in to quench the reaction. The product precipitated. Filtration and washing with water gave the product (2.5 g, 87%). $^1$H NMR (400 MHz, DMSO-d$_6$) δ ppm 4.49 (s, 2H) 6.93-7.10 (m, 2H) 7.33-7.45 (m, 2H) 7.56 (d, J=8.34 Hz, 1H) 7.77 (d, J=7.58 Hz, 1H) 7.82-7.92 (m, 5H) 7.98 (d, 1H). LC/MS: MS (ES+) m/e 473.1 [M+H]$^+$ e) 5: 2-({[5-chloro-7-hydroxy-3-(1-naphthalenylmethyl)pyrazolo[1,5-a]pyrimidin-2-yl]amino}carbonyl)benzoic acid

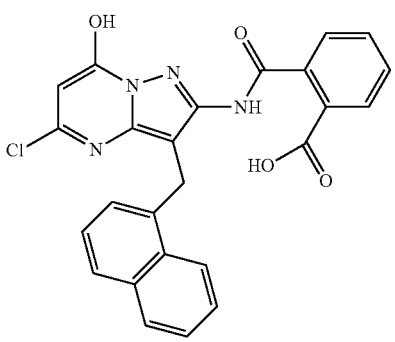 [SMILES: O=C(O)c1ccccc1C(=O)Nc1nn2c(O)cc(Cl)nc2c1Cc1cccc2ccccc12]

To a solution of 2-[5,7-dichloro-3-(1-naphthalenylmethyl)pyrazolo[1,5-a]pyrimidin-2-yl]-1H-isoindole-1,3(2H)-dione (2.1 g, 4.44 mmol) in Tetrahydrofuran (THF) (60 mL) was added in sodium hydroxide (26.6 mL, 26.6 mmol). The reaction mixture was stirred at rt for 18 h. Water (20 mL) and EtOAc (60 mL) was added in. The reaction was acidified with acetic acid (2.54 mL, 44.4 mmol). The aqueous phase was extracted with EtOAc (60 mL×2). The combined organic phases were washed with brine (30 mL), dried (MgSO$_4$) and concentrated. The crude was used for the next step. $^1$H NMR (400 MHz, DMSO-d$_6$) δ ppm 4.37 (s, 2H) 5.31 (s, 1H) 7.21 (s, 2H) 7.33 (m, 1H) 7.46 (m, 4H) 7.72 (m, 2H) 7.82-7.97 (m, 1H) 8.35 (m, 1H); LC/MS: MS (ES+) m/e 473.1 [M+H]$^+$.

f) 2-amino-5-(4-morpholinyl)-3-(1-naphthalenylmethyl)pyrazolo[1,5-a]pyrimidin-7-ol To a solution of 2-amino-5-(4-morpholinyl)-3-(1-naphthalenylmethyl)pyrazolo[1,5-a]pyrimidin-7-ol (0.2 g, 0.423 mmol) in Ethanol (1 mL) was added morpholine (0.553 mL, 6.34 mmol). The reaction was subjected to MW irradiation at 150° C. for 3 h. The reaction mixture was concentrated. The crude was purified by reverse-phase HPLC (20~50% CH3CN (0.1% TFA)/Water (0.1% TFA)) to give the titled product (0.032 g, 19%). $^1$H NMR (400 MHz, DMSO-d$_6$) δ ppm 3.26 (m, 4H) 3.62 (m, 4H) 4.27 (br. s., 2H) 5.00 (s, 1H) 7.11 (m, 1H) 7.39 (t, J=7.71 Hz, 1H) 7.47-7.63 (m, 2H) 7.78 (d, J=8.08 Hz, 1H) 7.94 (d, J=7.33 Hz, 1H) 8.30 (m, 1H); LC/MS: MS (ES+) m/e 376.1 [M+H]$^+$.

Example 24

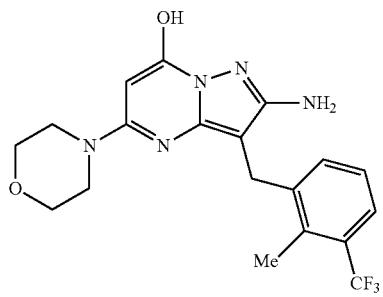 [SMILES: Cc1c(Cc2c(N)nn3c(O)cc(N4CCOCC4)nc23)cccc1C(F)(F)F]

Preparation of 2-amino-3-(2-methyl-3-(trifluoromethyl)benzyl)-5-morpholinopyrazolo[1,5-a]pyrimidin-7-ol a) 4-{[2-methyl-3-(trifluoromethyl)phenyl]methyl}-1H-pyrazole-3,5-diamine

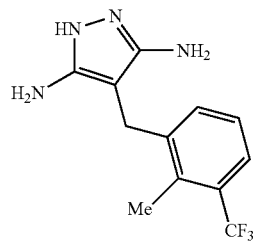 [SMILES: Cc1c(Cc2c(N)n[nH]c2N)cccc1C(F)(F)F]

To a mixture of malononitrile (2.352 g, 35.6 mmol) in 95% Ethanol (50 mL) was added 2-methyl-3-(trifluoromethyl) benzaldehyde (6.7 g, 35.6 mmol). The reaction was stirred at rt for 18 h. Additional EtOH (20 mL) was added and the mixture was stirred for 20 minutes and cooled to 0° C. in an ice bath. Sodium borohydride (0.364 g, 9.61 mmol) was introduced to the vigorously stirred mixture and the reduction was complete in about 10 min. To the reaction mixture was added water (40 mL). 1N HCl was added in to quench the excess hydride. More water was added in until precipitation was complete. Filtration gave {[2-methyl-3-(trifluoromethyl) phenyl]methyl}propanedinitrile (6.5 g, 77%). To a mixture of {[2-methyl-3-(trifluoromethyl)phenyl] methyl}propanedinitrile (6.5 g, 27.3 mmol) in Ethanol (80 mL) was added hydrazine hydrate (2.68 mL, 54.6 mmol). The reaction mixture was heated at reflux temperature for 8 h. The reaction mixture was concentrated. The crude material was purified on a silica column (eluting with MeOH/DCM: 0~10%) to give the product (3.5 g, 47%). $^1$H NMR (400 MHz, METHANOL-d$_4$) δ ppm 2.47 (s, 3H) 3.69 (s, 2H) 7.11-7.37 (m, 2H) 7.51 (d, 1H); LC/MS: MS (ES+) m/e 271.2 [M+H]$^+$.

b) 2-amino-3-{[2-methyl-3-(trifluoromethyl)phenyl] methyl}pyrazolo[1,5-a]pyrimidine-5,7(4H,6H)-dione

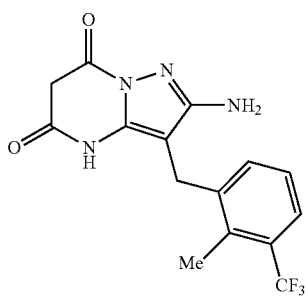 [SMILES: Cc1c(Cc2c(N)nn3c2NC(=O)CC3=O)cccc1C(F)(F)F]

To a solution of 4-{[2-methyl-3-(trifluoromethyl)phenyl] methyl}-1H-pyrazole-3,5-diamine (1 g, 3.70 mmol), dimethyl propanedioate (1.467 g, 11.10 mmol) in methanol (30 mL) was added sodium methoxide (0.680 g, 12.58 mmol). The reaction mixture was stirred at 65° C. for 18 h. After the reaction mixture was cooled to room temperature, the solvent was evaporated. Water (10 mL) was added in. The mixture was neutralized with 1 N HCl. Filtration gave the product (1.2 g, 96%). $^1$H NMR (400 MHz, DMSO-d$_6$) δ ppm 2.41 (s, 3H) 3.59-3.67 (s, 2H) 3.73 (s, 2H) 5.64 (br. s., 2H) 7.14 (d, J=7.83

Hz, 1H) 7.30 (m, 1H) 7.54 (d, J=7.83 Hz, 1H) 11.26 (s, 1H); LC/MS: MS (ES+) m/e 339.1 [M+H]+ c) 2-(1,3-dioxo-1,3-dihydro-2H-isoindol-2-yl)-3-{[2-methyl-3-(trifluoromethyl)phenyl]methyl}pyrazolo[1,5-a]pyrimidine-5,7(4H,6H)-dione

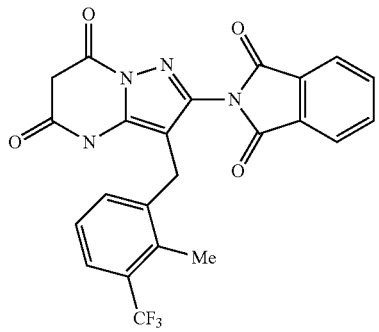 [SMILES: Cc1c(Cc2c(N3C(=O)c4ccccc4C3=O)nn3c2NC(=O)CC3=O)cccc1C(F)(F)F]

To the solution of 2-amino-3-{[2-methyl-3-(trifluoromethyl)phenyl]methyl}pyrazolo[1,5-a]pyrimidine-5,7(4H,6H)-dione (1.5 g, 4.43 mmol) in acetonitrile (100 mL) was added phthalic anhydride (1.511 g, 10.20 mmol). The reaction mixture was stirred at 80° C. for 4 days. The reaction was concentrated. To the crude was added DCM (20 mL). The insoluble solid was filtered which is the pure product. The filtrate was purified on a silica column (eluting with 20-60% EtOAc/Hexane) which was combined with the solid from filtration to give the product (1.0 g, 48%). $^1$H NMR (400 MHz, DMSO-$d_6$) δ ppm 2.20 (s, 3H) 3.93 (br. s., 2H) 6.89 (t, J=7.83 Hz, 1H) 7.10 (m, 1H) 7.22 (m, 1H) 7.49-7.62 (m, 1H) 7.62-7.70 (m, 1H) 7.79-7.94 (m, 4H); LC/MS: MS (ES+) m/e 469.1 [M+H]+.

d) 2-(5,7-dichloro-3-{[2-methyl-3-(trifluoromethyl)phenyl]methyl}pyrazolo[1,5-a]pyrimidin-2-yl)-1H-isoindole-1,3(2H)-dione

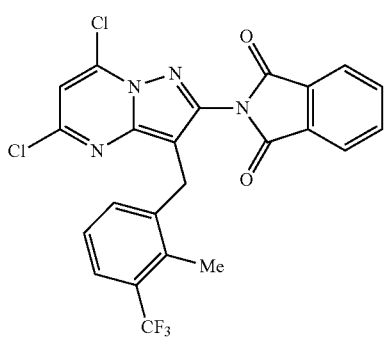 [SMILES: Cc1c(Cc2c(N3C(=O)c4ccccc4C3=O)nn3c(Cl)cc(Cl)nc23)cccc1C(F)(F)F]

A mixture of 2-(1,3-dioxo-1,3-dihydro-2H-isoindol-2-yl)-3-{[2-methyl-3-(trifluoromethyl)phenyl]methyl}pyrazolo[1,5-a]pyrimidine-5,7(4H,6H)-dione (1 g, 2.135 mmol) in POCl$_3$ (19.90 ml, 213 mmol) was heated at 90° C. for 18 h. The reaction mixture was concentrated. Water (15 mL) was added to quench the reaction. The product precipitated. Filtration and washing with water gave the product (1.0 g, 93%). $^1$H NMR (400 MHz, DMSO-$d_6$) δ ppm 2.21 (s, 3H) 4.15 (s, 2H) 6.90 (t, J=7.83 Hz, 1H) 7.21 (t, J=8.21 Hz, 2H) 7.75-7.95 (m, 5H); LC/MS: MS (ES+) m/e 504.8 [M+H]+.

e) 2-amino-3-(2-methyl-3-(trifluoromethyl)benzyl)-5-morpholinopyrazolo[1,5-a]pyrimidin-7-ol To a solution of 2-(5,7-dichloro-3-{[2-methyl-3-(trifluoromethyl)phenyl]methyl}pyrazolo[1,5-a]pyrimidin-2-yl)-1H-isoindole-1,3(2H)-dione (1.0 g, 1.979 mmol) in Tetrahydrofuran (THF) (30 mL) was added sodium hydroxide (1.187 mL, 5.94 mmol). The reaction mixture was stirred at rt for 18 h. Sodium hydroxide (1.187 mL, 5.94 mmol) was added to the reaction. The reaction mixture was stirred at rt for 3 h. Water (20 mL) and EtOAc (20 mL) was added in. The reaction mixture was acidified with acetic acid (0.680 mL, 11.87 mmol). The aqueous phase was extracted with EtOAc (30 mL). The combined organic phases were washed with brine (30 mL), dried (MgSO$_4$) and concentrated. To the crude in Ethanol (5 mL) was added morpholine (1.035 mL, 11.87 mmol). The reaction was subjected to MW irradiation at 150° C. for 7 h. The reaction was concentrated. To the crude was added Ethanol (20 mL) and hydrazine (0.097 mL, 1.979 mmol). The reaction mixture was refluxed for 3 h. The reaction was concentrated and purified by reversed phase HPLC (20~50% CH3CN (0.1% TFA)/Water (0.1% TFA)). NMR is not clean. To the solution of 2-amino-3-{[2-methyl-3-(trifluoromethyl)phenyl]methyl}-5-(4-morpholinyl)pyrazolo[1,5-a]pyrimidin-7(4H)-one (0.13 g, 0.319 mmol) in Acetonitrile (4 mL) was added phthalic anhydride (0.142 g, 0.957 mmol). The reaction mixture was stirred at 100° C. for 6 h. The reaction was concentrated. The residue was purified on a silica column (20~60% EtOAc/Hexane) and then (0~10% MeOH/DCM). To the purified material was added Ethanol (10 mL) and hydrazine (0.020 mL, 0.638 mmol). The reaction mixture was refluxed for 1 h. The reaction mixture was concentrated and purified by reverse phase HPLC (20~50% CH3CN (0.1% TFA)/Water (0.1% TFA)). $^1$H NMR (400 MHz, DMSO-$d_6$) δ ppm 2.45 (s, 3H) 3.25 (m, 4H) 3.64 (m, 4H) 3.81 (s, 2H) 4.99 (s, 1H) 7.11-7.24 (m, 1H) 7.25-7.33 (m, 1H) 7.53 (m, 1H); LC/MS: MS (ES+) m/e 408.1 [M+H]+.

Example 25

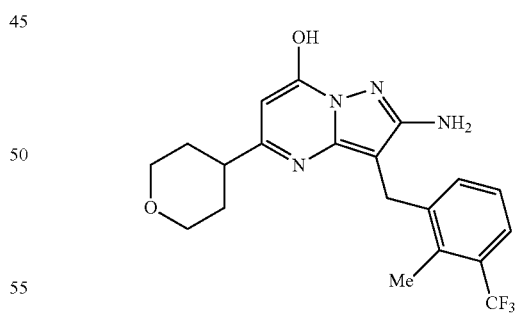

Preparation of 2-amino-3-(2-methyl-3-(trifluoromethyl)benzyl)-5-(tetrahydro-2H-pyran-4-yl)pyrazolo[1,5-a]pyrimidin-7-ol To a mixture of ethyl 3-oxo-3-(tetrahydro-2H-pyran-4-yl)propanoate (0.2 g, 0.999 mmol) and 4-{[2-methyl-3-(trifluoromethyl)phenyl]methyl}-1H-pyrazole-3,5-diamine (0.270 g, 0.999 mmol) was added Methanol (4 mL) and hydrochloric acid (0.4 mL, 0.500 mmol) in methanol (1.25 N). The reaction vessel was sealed and heated at 65° C. for 6 days. The reaction mixture was concentrated to 1 mL. The solid was filtered and wash with methanol (2 ml×3) and dried (0.19 g, 45%). ¹H NMR (400 MHz, DMSO-d₆) δ ppm 1.51-1.84 (m, 4H) 2.47 (s, 3H) 2.58-2.75 (m, 1H) 3.34-3.39 (m, 2H) 3.85 (s, 2H) 3.93 (dd, J=11.24, 3.16 Hz, 2H) 5.28 (s, 2H) 5.41 (d, J=1.52 Hz, 1H) 7.01 (d, J=7.83 Hz, 1H) 7.28 (m, 1H) 7.54 (d, J=7.83 Hz, 1H) 11.18 (s, 1H); LC/MS: MS (ES+) m/e 407.2 [M+H]⁺.

Example 26

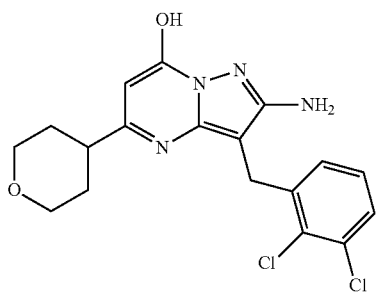 [SMILES: Nc1nn2c(O)cc(C3CCOCC3)nc2c1Cc1cccc(Cl)c1Cl]

a) 4-[(2,3-dichlorophenyl)methyl]-1H-pyrazole-3,5-diamine

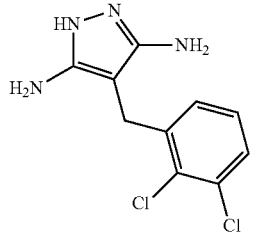 [SMILES: Nc1n[nH]c(N)c1Cc1cccc(Cl)c1Cl]

To a mixture of malononitrile (2.64 g, 40 mmol) in 95% Ethanol (50 mL) was added 2,3-dichlorobenzaldehyde (7.00 g, 40.0 mmol). The reaction was stirred at rt for 18 h. EtOH (20 mL) was added and the mixture was stirred at rt for 20 min and cooled to 0° C. in an ice bath. Sodium borohydride (0.424 g, 11.20 mmol) was introduced to the vigorously stirred mixture and the reduction was complete in about 10 min. To the reaction mixture was added water (40 mL). 1N HCl was added in to quench the excess hydride. More water was added in until precipitation was complete. Filtration gave [(2,3-dichlorophenyl)methyl]propanedinitrile (7.86 g, 87%). To a solution of [(2,3-dichlorophenyl)methyl]propanedinitrile (7.86 g, 34.9 mmol) in Ethanol (80 mL) was added hydrazine hydrate (2.57 mL, 52.4 mmol). The mixture is heated at reflux temperature for 8 h. The reaction mixture was concentrated. The crude material was purified on a silica column (MeOH/DCM: 0~10%) to give the product (4.2 g, 47%). ¹H NMR (400 MHz, METHANOL-d₄) δ ppm 3.77 (s, 2H) 7.09 (m, 1H) 7.19 (t, J=7.96 Hz, 1H) 7.38 (m, 1H); LC/MS: MS (ES+) m/e 257.0 [M+H]⁺.

b) 2-amino-3-(2,3-dichlorobenzyl)-5-(tetrahydro-2H-pyran-4-yl)pyrazolo[1,5-a]pyrimidin-7-ol hydrochloride To a mixture of ethyl 3-oxo-3-(tetrahydro-2H-pyran-4-yl) propanoate (0.100 g, 0.498 mmol) and 4-[(2,3-dichlorophenyl)methyl]-1H-pyrazole-3,5-diamine (0.128 g, 0.498 mmol) was added in Acetic Acid (2 mL). The reaction vessel was subjected to MW irradiation at 100° C. for 40 min then 70° C. for 180 min. The mixture was concentrated. The residue was purified by reversed phase HPLC (25% CH3CN (0.1% TFA)/Water (0.1% TFA)) and then repurified (10~50% CH3CN (0.1% TFA)/Water (0.1% TFA) to give the product. 1 M ether/HCl (3 mL) was added to the solution of the product in MeOH (10 mL). The mixture was stirred for 3 h. The solvent was removed to give the titled product as solid (55 mg, 27%). ¹H NMR (400 MHz, DMSO-d₆) δ ppm 1.53-1.84 (m, 4H) 2.63-2.83 (m, 1H) 3.22-3.46 (m, 2H) 3.93 (m, 2H) 4.01 (s, 2H) 5.63 (s, 1H) 6.90 (d, J=7.07 Hz, 1H) 7.25 (t, J=7.96 Hz, 1H) 7.43-7.59 (m, 1H) 11.92 (br. s., 1H). LC/MS: MS (ES+) m/e 393.0 [M+H]⁺.

Example 27

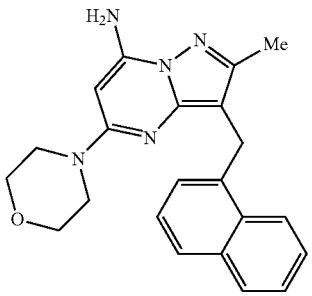 [SMILES: Cc1nn2c(N)cc(N3CCOCC3)nc2c1Cc1cccc2ccccc12]

Preparation of 2-methyl-5-morpholino-3-(naphthalen-1-ylmethyl)pyrazolo[1,5-a]pyrimidin-7-amine To the solution of 5,7-dichloro-2-methyl-3-(1-naphthalenylmethyl)pyrazolo[1,5-a]pyrimidine (0.05 g, 0.146 mmol) in 1,4-Dioxane (5 mL) was added ammonium hydroxide (0.508 mL, 3.65 mmol). The reaction was stirred at rt for 3 days. The reaction was concentrated to give the solid. To the mixture of the solid in Ethanol (1 mL) was added morpholine (0.382 mL, 4.38 mmol). The mixture was subjected to MW irradiation at 150° C. for 6 h. The reaction mixture was concentrated. The crude was purified by reversed phase HPLC (20~50% CH3CN (0.1% TFA)/Water (0.1% TFA)). The fractions from purification were concentrated. NaHCO₃ solution (3 mL) was added in and extracted with EtOAc (20 mL). The organic phase was washed with Brine (5 mL), dried (MgSO₄) and concentrated to give the product as solid. ¹H NMR (400 MHz, DMSO-d₆) δ ppm 2.18 (s, 3H) 3.46-3.52 (t, J=5.24 Hz, 4H) 3.65-3.74 (t, J=4.52 Hz, 3H) 4.28 (s, 2H) 5.49 (s, 1H) 7.07 (br. s., 2H) 7.31 (m, 1H) 7.37-7.43 (m, 1H)

7.45-7.52 (m, 2H) 7.75 (d, J=8.34 Hz, 1H) 7.85-7.93 (m, 1H) 8.54 (m, 1H); LC/MS: MS (ES+) m/e 374.0 [M+H]+.

Example 28

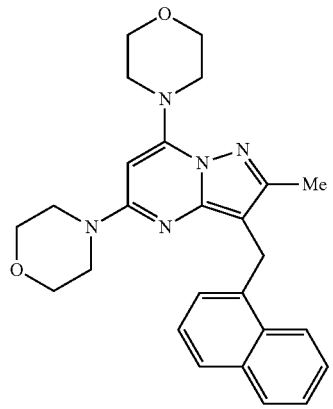 [SMILES: Cc1nn2c(N3CCOCC3)cc(N3CCOCC3)nc2c1Cc1cccc2ccccc12]

Preparation of 4,4'-(2-methyl-3-(naphthalen-1-ylmethyl)pyrazolo[1,5-a]pyrimidine-5,7-diyl)dimorpholine To the solution of 5,7-dichloro-2-methyl-3-(1-naphthalenylmethyl)pyrazolo[1,5-a]pyrimidine (0.2 g, 0.584 mmol) in Tetrahydrofuran (THF) (5 mL) was added sodium hydroxide (2.045 mL, 4.09 mmol). The reaction was stirred at rt for 18 h. The reaction was acidified. The reaction was extracted with EtOAc (80 mL×2). The organic phases were combined, washed with Brine, dried and concentrated. The mixture was transferred to 5 mL MW vial. Morpholine (0.509 mL, 5.84 mmol) and Ethanol (1 mL) was added in. The reaction mixture was subjected to MW irradiation at 150° C. for 3 h. 6 N HCl was added to the reaction to acidify the solution. The reaction mixture was extracted with EtOAc (50 mL×2). The organic phases were combined, washed with Brine, dried and concentrated. The residue was purified by reversed phase HPLC (25~55% CH3CN (0.1% TFA)/Water (0.1% TFA)) to give the product (30 mg, 11%). 1H NMR (400 MHz, DMSO-d6) δ ppm 2.17 (s, 3H) 3.52-3.64 (m, 8H) 3.66-3.73 (t, J=4.63 Hz, 4H) 3.74-3.82 (t, J=4.44 Hz, 4H) 4.30 (s, 2H) 5.78 (s, 1H) 7.31 (d, J=6.57 Hz, 1H) 7.37-7.43 (m, 1H) 7.43-7.53 (m, 2H) 7.75 (d, J=8.08 Hz, 1H) 7.84-7.94 (m, 1H) 8.46-8.56 (m, 1H); LC/MS: MS (ES+) m/e 444.2 [M+H]+.

Example 29

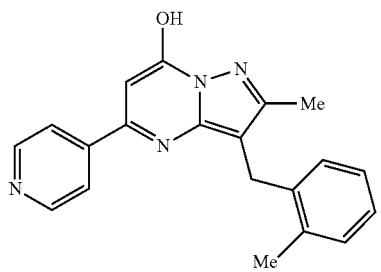 [SMILES: Cc1ccccc1Cc1c(C)nn2c(O)cc(-c3ccncc3)nc12]

Preparation 2-methyl-3-(2-methylbenzyl)-5-(pyridin-4-yl)pyrazolo[1,5-a]pyrimidin-7-ol a) (1-cyano-2-oxopropyl)sodium

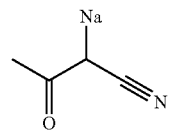

Sodium (7.36 g, 320 mmol) was reacted with ethanol (368 ml) and then 5-methylisoxazole (26.56 g, 320 mmol) was added to the mixture at 20° C. The mixture was stirred at 20° C. for 1.5 h and at 0° C. for 1.5 h. The white solid was collected by filtration, washed with ether, dried in vacuo to provide the titled compound (10.168 g, 30%) as a white solid.

b) 2-(2-methylbenzyl)-3-oxobutanenitrile

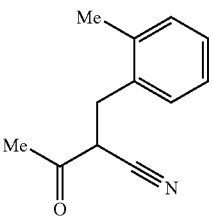 [SMILES: CC(=O)C(C#N)Cc1ccccc1C]

To a solution of (1-cyano-2-oxopropyl)sodium (525 mg, 5 mmol) in DMF (15 mL) was added 1-(bromomethyl)-2-methylbenzene (648 mg, 3.5 mmol) dropwise over a period of 15 min at 0° C. The mixture was stirred at 0° C. for 1 h and at room temperature for 2 h. Then this solution was diluted with saturated aq. ammonium chloride solution. This solution was extracted with ethyl acetate (30 mL×3). The combined organic layers were washed with water and brine, dried over Na2SO4, concentrated under reduced pressure. The residue was purified by a silica gel chromatography (petroleum ether/ethyl acetate=15/1) to give the titled product (181 mg, 28%) as a colorless oil; LC/MS: MS (ES+) m/e 188 (MH+); 1H NMR (300 MHz, CDCl3) δ ppm 2.35 (s, 3H), 2.38 (s, 3H), 3.06 (dd, J=9.6, 14.1 Hz, 1H), 3.28 (dd, J=5.4, 14.1 Hz, 1H), 3.60 (dd, J=5.4, 9.6 Hz, 1H), 7.18-7.22 (m, 4H).

c) 3-methyl-4-(2-methylbenzyl)-1H-pyrazol-5-amine

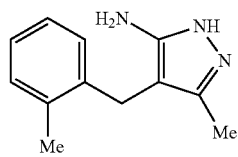 [SMILES: Cc1ccccc1Cc1c(C)n[nH]c1N]

To a solution of 2-(2-methylbenzyl)-3-oxobutanenitrile (7.39 g, 39.5 mmol) in ethanol (400 mL) was added hydrazine hydrate (1.97 g, 39.5 mmol) and stirred under reflux for 16 h. The mixture was cooled to room temperature and concentrated. The residue was purified by silica gel column (petroleum ether/ethyl acetate=1/1 then DCM:methanol=40:1) to provide the titled compound (3.005 g, 38%) as a yellow solid; LC/MS: MS (ES⁺) m/e 202 (MH⁺); ¹H NMR (300 MHz, CDCl₃) δ ppm 2.12 (s, 3H), 2.33 (s, 3H), 3.63 (s, 2H), 7.07-7.17 (m, 4H).

d) 2-methyl-3-(2-methylbenzyl)-5-(pyridin-4-yl)pyrazolo[1,5-a]pyrimidin-7-ol acetate

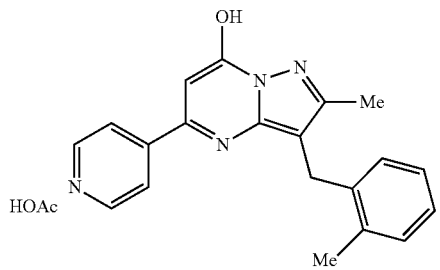 [SMILES: Cc1ccccc1Cc1c(C)nn2c(O)cc(-c3ccncc3)nc12 ; "HOAc"]

A solution of 3-methyl-4-(2-methylbenzyl)-1H-pyrazol-5-amine (3.005 g, 14.93 mmol) and ethyl 3-oxo-3-(pyridin-4-yl)propanoate (3.17 g, 16.42 mmol) in acetic acid (50 mL) was stirred under reflux for 48 h. After cooled to room temperature, the mixture was concentrated. The residue was diluted with ethyl acetate (30 mL). The resulting precipitate was filtered, washed with ethyl acetate, dried in vacuo to give the titled product (4.02 g, 69%); LC/MS: MS (ES⁺) m/e 331 (MH⁺); ¹H NMR (300 MHz, DMSO-d₆) δ ppm 1.91 (s, 3H), 2.09 (s, 3H), 2.36 (s, 3H), 3.99 (s, 2H), 6.08 (s, 1H), 6.78 (d, J=7.8 Hz, 1H), 7.04-7.21 (m, 3H), 7.77 (d, J=4.8 Hz, 1H), 8.76 (d, J=4.8 Hz, 1H), 11.95 (s, 1H), 12.16 (s, 1H).

e) 2-methyl-3-(2-methylbenzyl)-5-(pyridin-4-yl)pyrazolo[1,5-a]pyrimidin-7-ol

A mixture of 3-methyl-4-(2-methylbenzyl)-1H-pyrazol-5-amine (120 mg, 0.307 mmol), sodium bicarbonate (0.5 g) in methanol/water (20 mL/10 mL) was stirred at room temperature for 16 h. Then the mixture was concentrated. The residue was purified by silica gel column to give the titled product (82 mg, 73%); LC/MS: MS (ES⁺) m/e 331 (MH⁺); ¹H NMR (300 MHz, DMSO-d₆) δ ppm 2.11 (s, 3H), 2.37 (s, 3H), 3.97 (s, 2H), 6.09 (s, 1H), 6.83 (d, J=7.8 Hz, 1H), 7.03-7.19 (m, 3H), 7.81 (d, J=4.8 Hz, 1H), 8.73 (d, J=4.8 Hz, 1H), 12.16 (s, 1H).

Example 30

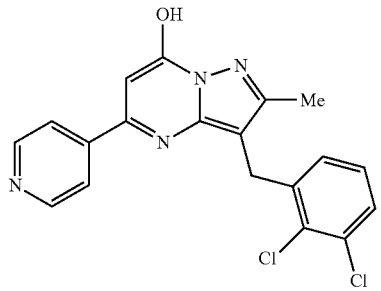

Preparation 3-(2,3-dichlorobenzyl)-2-methyl-5-(pyridin-4-yl)pyrazolo[1,5-a]pyrimidin-7-ol a) 2-(2,3-dichlorobenzyl)-3-oxobutanenitrile

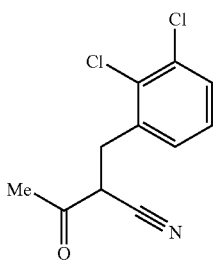 [SMILES: CC(=O)C(C#N)Cc1cccc(Cl)c1Cl]

To a solution of (1-cyano-2-oxopropyl)sodium (1.28 g, 12.16 mmol) in DMF (80 mL) was added 1-(bromomethyl)-2,3-dichlorobenzene (2.043 g, 8.51 mmol) dropwise over a period of 30 min at 0° C. The mixture was stirred at 0° C. for 1 h and at room temperature for 2 h. Then this solution was diluted with saturated aq. ammonium chloride solution. The resulting solution was extracted with ethyl acetate (80 mL×3). The combined organic layers were washed with water and brine, dried over sodium sulphate, concentrated under reduced pressure to give the crude product (2.19 g, 100%), which was used for the next step without further purification. LC/MS: MS (ES⁺) m/e 242 (MH⁺).

b) 4-(2,3-dichlorobenzyl)-3-methyl-1H-pyrazol-5-amine

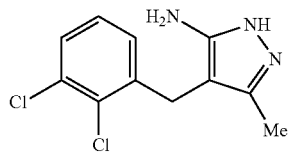 [SMILES: Cc1n[nH]c(N)c1Cc1cccc(Cl)c1Cl]

To a solution of 2-(2,3-dichlorobenzyl)-3-oxobutanenitrile (2.19, 9.05 mmol) in ethanol (400 mL) was added hydrazine hydrate (0.452 g, 9.05 mmol) and the resulting solution was stirred under reflux for 16 h. Then the mixture was cooled to room temperature and concentrated. The residue was purified by silica gel column (petroleum ether/ethyl acetate=1/1 then DCM:methanol=40:1) to provide the titled compound (1.21 g, 52%) as a yellow solid; LC/MS: MS (ES⁺) m/e 256 (MH⁺);

¹H NMR (300 MHz, CDCl₃) δ ppm 2.13 (s, 3H), 3.77 (s, 2H), 6.97 (dd, J=1.2, 7.8 Hz, 1H), 7.10 (t, J=7.8 Hz, 1H), 7.33 (dd, J=1.2, 7.8 Hz, 1H)

c 3-(2,3-dichlorobenzyl)-2-methyl-5-(pyridin-4-yl)pyrazolo[1,5-a]pyrimidin-7-ol acetate

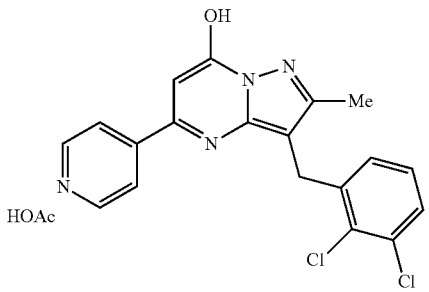 [SMILES: Cc1nn2c(O)cc(-c3ccncc3)nc2c1Cc1cccc(Cl)c1Cl ; "HOAc"]

A mixture of 4-(2,3-dichlorobenzyl)-3-methyl-1H-pyrazol-5-amine (1.21 g, 4.72 mmol), ethyl 3-oxo-3-(pyridin-4-yl)propanoate (1.004 g, 5.195 mmol) in acetic acid (50 mL) was stirred under reflux overnight. After cooled to room temperature, the mixture was concentrated. The residue was diluted with ethyl acetate (20 mL). The resulting precipitate was filtered, washed with ethyl acetate, dried in vacuo to give the titled product (1.266 g, 60%); LC/MS: MS (ES⁺) m/e 385 (MH⁺); ¹H NMR (300 MHz, DMSO-d₆) δ ppm 1.91 (s, 3H), 2.12 (s, 3H), 4.16 (s, 2H), 6.10 (s, 1H), 6.91 (dd, J=1.2, 7.8 Hz, 1H), 7.26 (t, J=7.8 Hz, 1H), 7.51 (dd, J=1.2, 7.8 Hz, 1H), 7.77 (d, J=5.7 Hz, 2H), 8.77 (d, J=5.7 Hz, 2H), 11.94 (s, 1H), 12.18 (s, 1H).

d) 3-(2,3-dichlorobenzyl)-2-methyl-5-(pyridin-4-yl)pyrazolo[1,5-a]pyrimidin-7-ol A mixture of 3-(2,3-dichlorobenzyl)-2-methyl-5-(pyridin-4-yl)pyrazolo[1,5-a]pyrimidin-7(4H)-one acetate (100 mg, 0.225 mmol), sodium bicarbonate (0.5 g) in methanol/water (20 mL/10 mL) was stirred at room temperature overnight. Then the mixture was concentrated. The residue was purified by silica gel column to give the titled product (75 mg, 87%); LC/MS: MS (ES⁺) m/e 385 (MH⁺); ¹H NMR (300 MHz, DMSO-d₆) δ ppm 2.15 (s, 3H), 4.14 (s, 2H), 6.11 (s, 1H), 6.97-7.00 (m, 1H), 7.25 (t, J=8.1 Hz, 1H), 7.48-7.50 (m, 1H), 7.82-7.82 (m, 2H), 8.71-8.74 (m, 2H), 12.20 (s, 1H).

Example 31

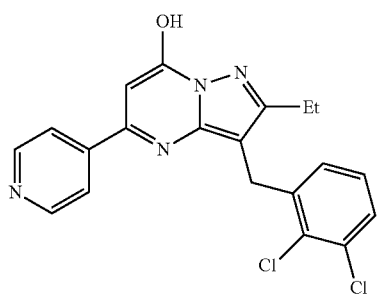

Preparation 3-(2,3-dichlorobenzyl)-2-ethyl-5-(pyridin-4-yl)pyrazolo[1,5-a]pyrimidin-7-ol a) 2-(2,3-dichlorobenzyl)-3-oxopentanenitrile

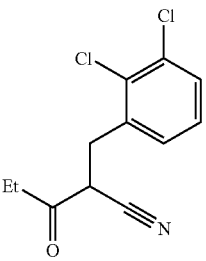 [SMILES: CCC(=O)C(C#N)Cc1cccc(Cl)c1Cl]

To a solution of 3-oxopentanenitrile (500 mg, 5.2 mmol) in DMF (10 mL) was added NaH (248 mg, 6.2 mmol) and stirred at 0° C. for 1 h. Then 1-(bromomethyl)-2,3-dichlorobenzene (1.23 g, 5.2 mmol) was added to the mixture and warmed to room temperature, stirred for 20 h. The mixture was concentrated under reduced pressure to give the crude titled product (1.2 g, 92%), which was used for next step without further purification.

b) 4-(2,3-dichlorobenzyl)-3-ethyl-1H-pyrazol-5-amine

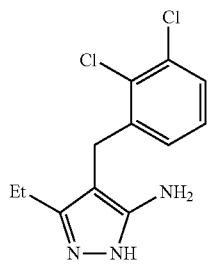 [SMILES: CCc1n[nH]c(N)c1Cc1cccc(Cl)c1Cl]

To a solution of 2-(2,3-dichlorobenzyl)-3-oxopentanenitrile (1.2 g, 4.7 mmol) in EtOH (10 mL) was added hydrazine hydrate (285 mg, 5.7 mmol) and stirred at 90° C. for 20 h. The mixture was cooled to room temperature and concentrated. The residue was purified by silica gel column (PE:EA=10:1) to give the titled compound (500 mg, 36% over two steps); LC/MS: MS (ES⁺) m/e 270 (MH⁺); ¹H NMR (300 MHz, CDCl₃) δ ppm 1.16 (t, J=7.5 Hz, 3H), 2.53 (q, J=7.5 Hz, 2H), 3.78 (s, 2H), 4.26 (s, 2H), 6.94-6.97 (m, 1H), 7.10 (t, J=7.8 Hz, 1H), 7.32-7.35 (m, 1H).

c) 3-(2,3-dichlorobenzyl)-2-ethyl-5-(pyridin-4-yl)pyrazolo[1,5-a]pyrimidin-7-ol

A mixture of 4-(2,3-dichlorobenzyl)-3-ethyl-1H-pyrazol-5-amine (250 mg, 0.93 mmol), ethyl 3-oxo-3-(pyridin-4-yl)propanoate (198 mg, 1.03 mmol) in acetic acid (10 mL) and water (0.5 mL) was stirred at 120° C. for 20 h, cooled and the pH was carefully adjusted to 8. The mixture was extracted with DCM (100 mL×3). The combined organic layers were dried over Na₂SO₄, filtered and concentrated. The residue was purified by silica gel column (PE:EA=10:1) to give the titled compound (95 mg, 26%); LC/MS: MS (ES⁺) m/e 399 (MH⁺); ¹H NMR (300 MHz, DMSO-d₆) δ ppm 1.12 (t, J=7.5

Hz, 3H), 2.56 (q, J=7.5 Hz, 2H), 4.07 (s, 2H), 5.97 (s, 1H), 7.16-7.21 (m, 2H), 7.42 (d, 2.1 Hz, 1H), 7.90 (dd, J=1.5, 4.5 Hz, 1H), 8.56 (dd, J=1.5, 4.5 Hz, 1H).

Example 32

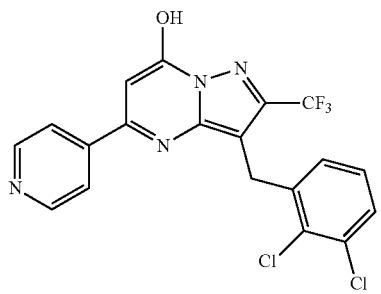 [SMILES: Oc1cc(-c2ccncc2)nc2c(Cc3cccc(Cl)c3Cl)c(C(F)(F)F)nn12]

Preparation 3-(2,3-dichlorobenzyl)-5-(pyridin-4-yl)-2-(trifluoromethyl)pyrazolo[1,5-a]pyrimidin-7-ol a) ethyl 2-cyano-3-(2,3-dichlorophenyl)propanoate

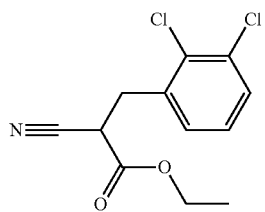 [SMILES: CCOC(=O)C(C#N)Cc1cccc(Cl)c1Cl]

A mixture of ethyl 2-cyanoacetate (4.52 g, 40 mmol), 1-(bromomethyl)-2,3-dichlorobenzene (4.8 g, 20 mmol) and potassium carbonate (11.04 g, 80 mmol) in THF (80 mL) was under reflux for 30 h. After cooled to room temperature, the solvent was removed in vacuo and the resulting mixture was acidified with 2 N hydrochloric acid. The resulting solution was extracted with ethyl acetate (80 mL×3). The combined organic layers were washed with water and brine, dried over sodium sulphate, concentrated under reduced pressure. The residue was crystallized with MeOH to give the titled product (1.0 g, 18%) as a white solid. The mother liquor was concentrated in vacuo and the residue was purified by a silica gel chromatography eluted with PE/EA=20/1 to give the titled product (1.53 g, 33%) as a colorless oil; LC/MS: MS (ES$^+$) m/e 272 (MH$^+$); $^1$H NMR (300 MHz, CDCl$_3$) δ ppm 1.31 (t, J=7.2 Hz, 3H), 3.24 (dd, J=9.6, 13.8 Hz, 1H), 3.56 (dd, J=6.3, 13.8 Hz, 1H), 3.90-3.96 (dd, J=6.3, 9.6 Hz, 1H), 4.28 (dq, J=0.9, 7.2 Hz, 2H), 7.18-7.29 (m, 2H), 7.44 (dd, J=1.8, 7.8 Hz, 1H).

b) 2-cyano-3-(2,3-dichlorophenyl)propanoic acid

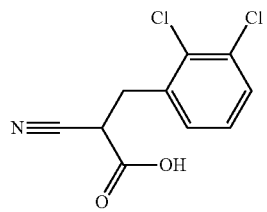 [SMILES: N#CC(Cc1cccc(Cl)c1Cl)C(=O)O]

To a solution of ethyl 2-cyano-3-(2,3-dichlorophenyl)propanoate (1.02 g, 3.63 mmol) in methanol/water (15 mL/15 mL) was added sodium carbonate (1.54 g, 14.5 mmol). The mixture was stirred at 65° C. overnight. After cooled to room temperature, the mixture was concentrated under vacuo to remove MeOH, the resulting mixture was then acidified with 4 N hydrochloric acid. This solution was extracted with ethyl acetate (50 mL×3). The combined organic layers were washed with water and brine, dried over sodium sulphate, concentrated under reduced pressure to give the titled product (0.87 g, 98%) as a white solid; LC/MS: MS (ES$^+$) m/e 244 (MH$^+$); $^1$H NMR (300 MHz, CDCl$_3$) δ ppm 3.21 (dd, J=10.2, 13.8 Hz, 1H), 3.59 (dd, J=5.4, 13.8 Hz, 1H), 3.87-3.92 (dd, J=5.4, 10.2 Hz, 1H), 4.74 (s, br, 1H), 7.18-7.32 (m, 2H), 7.44 (dd, J=1.8, 7.8 Hz, 1H).

c) 3-(2,3-dichlorophenyl)propanenitrile

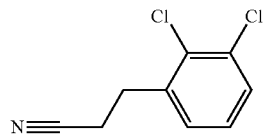 [SMILES: N#CCCc1cccc(Cl)c1Cl]

2-cyano-3-(2,3-dichlorophenyl)propanoic acid (0.87 g, 3.56 mmol) was heated at 180° C. for 45 min. After cooled to room temperature, the residue was purified by a silica gel chromatography eluted with PE/EA=10/1 to give the titled product (376 g, 53%) as a colorless oil; LC/MS: MS (ES$^+$) m/e 200 (MH$^+$); $^1$H NMR (300 MHz, CDCl$_3$) δ ppm 2.70 (t, J=7.2 Hz, 2H), 3.13 (t, J=7.2 Hz, 2H), 7.17-7.23 (m, 2H), 7.42 (dd, J=2.4, 7.2 Hz, 1H).

d) 2-(2,3-dichlorobenzyl)-4,4,4-trifluoro-3-oxobutanenitrile

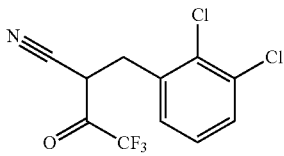 [SMILES: N#CC(Cc1cccc(Cl)c1Cl)C(=O)C(F)(F)F]

To a mixture of 3-(2,3-dichlorophenyl)propanenitrile (100 mg, 0.5 mmol) in THF (20 mL) was added LDA (0.5 mL, 2 N in hexane, 1 mmol) dropwise at −78° C. under nitrogen. The mixture was stirred at −78° C. for 0.5 h. Then ethyl 2,2,2-trifluoroacetate (177.5 mg, 1.25 mmol) was added to the mixture dropwise. This solution was stirred at −78° C. for 5 h and diluted with sat. aq. ammonium chloride solution and 1N hydrochloric acid. This solution was extracted with EA (30 mL*3). The combined organic layers were washed with water and brine, dried over sodium sulphate, concentrated under reduced pressure. The residue was purified by a silica gel chromatography to give the titled product (82 mg, 55%) as a yellow solid; LC/MS: MS (ES+) m/e 296 (MH+); $^1$H NMR (300 MHz, CDCl$_3$) δ ppm 3.03 (dd, J=12.9, 14.1 Hz, 1H), 3.52-3.60 (m, 2H), 7.20-7.32 (m, 2H), 7.43-7.51 (m, 1H).

e) 4-(2,3-dichlorobenzyl)-3-(trifluoromethyl)-1H-pyrazol-5-amine

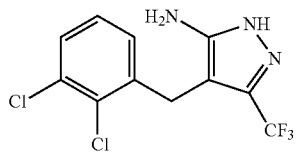 [SMILES: Nc1[nH]nc(C(F)(F)F)c1Cc1cccc(Cl)c1Cl]

To a solution of 2-(2,3-dichlorobenzyl)-4,4,4-trifluoro-3-oxobutanenitrile (10.0 g, 33.77 mmol) in ethanol (800 mL) was added hydrazine hydrate (1.86 g, 37.15 mmol) and the resulting solution was stirred under reflux for 16 h. The mixture was cooled to room temperature and concentrated. The residue was purified by silica gel column (petroleum ether/ethyl acetate=2/1) and reverse-phase Prep-HPLC to provide the titled compound (1.6 g, 15%) as a yellow oil; LC/MS: MS (ES+) m/e 310 (MH+); $^1$H NMR (300 MHz, DMSO-d$_6$) δ ppm 3.85 (s, 2H), 6.78 (dd, J=1.2, 7.8 Hz, 1H), 7.25 (t, J=7.8 Hz, 1H), 7.47 (dd, J=1.2, 7.8 Hz, 1H).

f) 3-(2,3-dichlorobenzyl)-5-(pyridin-4-yl)-2-(trifluoromethyl)pyrazolo[1,5-a]pyrimidin-7-ol A mixture of 4-(2,3-dichlorobenzyl)-3-(trifluoromethyl)-1H-pyrazol-5-amine (100 mg, 0.332 mmol), ethyl 3-oxo-3-(pyridin-4-yl)propanoate (75 mg, 0.387 mmol) in conc. H$_2$SO$_4$ (1.5 mL) and dioxane (15 mL) was placed in a sealed tube and stirred at 120° C. for 16 h. After cooled to room temperature, the pH of the mixture was carefully adjusted to 8 with saturated aq. sodium bicarbonate solution. The resulting mixture was extracted with DCM (50 mL×3). The combined organic layers were washed with water and brine, dried over sodium sulphate, filtered and concentrated. The residue was purified by silica gel column and reverse-phase Prep-HPLC to give the title product (14 mg, 10%) as a yellow solid; LC/MS: MS (ES+) m/e 439 (MH+); $^1$H NMR (300 MHz, DMSO-d$_6$) δ ppm 4.29 (s, 2H), 6.35 (s, 1H), 6.89 (dd, J=1.2, 7.8 Hz, 1H), 7.23 (t, J=7.8 Hz, 1H), 7.52 (dd, J=1.2, 7.8 Hz, 1H), 7.83 (d, J=6.0 Hz, 2H), 8.80 (d, J=6.0 Hz, 2H), 12.81 (s, 1H).

Example 33 & Example 34

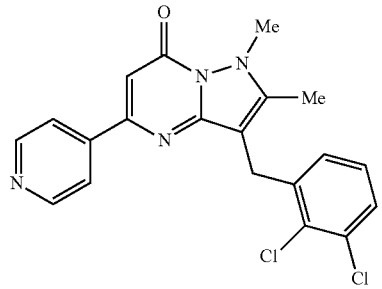

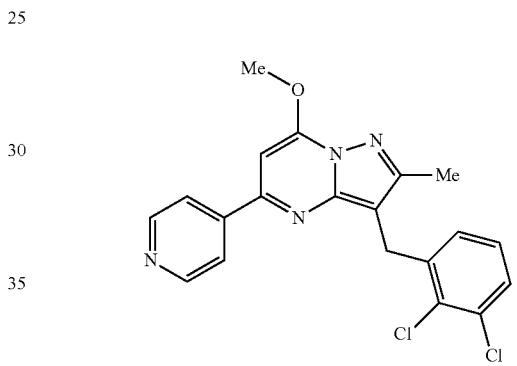

Preparation of 3-(2,3-dichlorobenzyl)-1,2-dimethyl-5-(pyridin-4-yl)pyrazolo[1,5-a]pyrimidin-7(1H)-one (37) and 3-(2,3-dichlorobenzyl)-7-methoxy-2-methyl-5-(pyridin-4-yl)pyrazolo[1,5-a]pyrimidine (38)

To a solution of 3-(2,3-dichlorobenzyl)-2-methyl-5-(pyridin-4-yl)pyrazolo[1,5-a]pyrimidin-7(4H)-one acetate (600 mg, 1.347 mmol) in dichloromethane/methanol (30 mL/15 mL) was added trimethylsilyldiazomethane (2 mL, 4.04 mmol). The mixture was stirred at room temperature overnight. Then the mixture was concentrated under reduced pressure. The residue was purified by a silica gel chromatography to give 3-(2,3-dichlorobenzyl)-1,2-dimethyl-5-(pyridin-4-yl)pyrazolo[1,5-a]pyrimidin-7(1H)-one (214 mg, 40%) and 3-(2,3-dichlorobenzyl)-7-methoxy-2-methyl-5-(pyridin-4-yl)pyrazolo[1,5-a]pyrimidine (83 mg, 15%). The structures of the two products were assigned according to NOESY. Example 33: 3-(2,3-dichlorobenzyl)-1,2-dimethyl-5-(pyridin-4-yl)pyrazolo[1,5-a]pyrimidin-7(1H)-one: LC/MS: MS (ES+) m/e 399 (MH+); $^1$H NMR (300 MHz, DMSO-d$_6$) □ ppm 2.42 (s, 3H), 4.15 (s, 2H), 4.21 (s, 3H), 6.59 (s, 1H), 7.28 (t, J=7.8 Hz, 1H), 7.36 (dd, J=1.8, 7.8 Hz, 1H), 7.51 (dd, J=1.8, 7.8 Hz, 1H), 7.95 (d, J=6.3 Hz, 2H), 8.66 (d, J=6.3 Hz, 2H). Example 34: 3-(2,3-dichlorobenzyl)-7-methoxy-2-methyl-5-(pyridin-4-yl)pyrazolo[1,5-a]pyrimidine: LC/MS: MS (ES+); $^1$H NMR (300 MHz, CDCl$_3$) δ ppm 2.44 (s, 3H), 4.31 (s, 5H), 6.58 (s, 1H), 7.04-7.07 (m, 2H), 7.32 (dd, J=3.0, 6.6 Hz, 1H), 7.50 (dd, J=1.5, 4.5 Hz, 2H), 8.76 (dd, J=1.5, 4.5 Hz, 2H).

Example 35

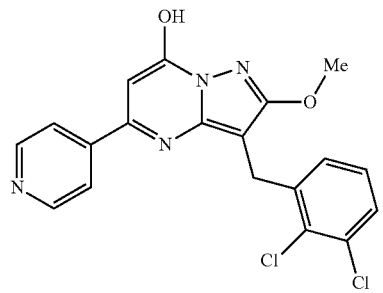 [SMILES: COc1nn2c(O)cc(-c3ccncc3)nc2c1Cc1cccc(Cl)c1Cl]

Preparation of 3-(2,3-dichlorobenzyl)-2-methoxy-5-(pyridin-4-yl)pyrazolo[1,5-a]pyrimidin-7-ol a) methyl 2,3-dichlorobenzoate

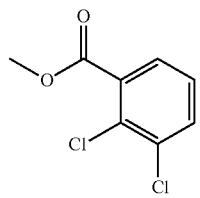

A solution of 2,3-dichlorobenzoic acid (100 g, 0.526 mol) in methanol (1 L), was added H₂SO₄ (20 mL). The solution was stirred under reflux overnight. The reaction mixture was cooled and concentrated. The resulting residue was diluted with water (100 mL) and ethyl acetate (1 L). Then the organic layer was washed with aq. NaHCO₃ and brine, dried over Na₂SO₄, filtered and the filtrate was concentrated to provide the titled compound (99 g, 92%), as a white solid; ¹H NMR (300 MHz, CDCl₃) δ ppm 3.95 (s, 3H), 7.27 (t, J=7.8 Hz, 1H), 7.60 (dd, J=1.8, 7.8 Hz, 1H), 7.66 (dd, J=1.8, 7.8 Hz, 1H).

b) (2,3-dichlorophenyl)methanol

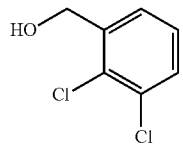

A suspension of LiAlH₄ (7.4 g, 0.195 mol) in THF (500 mL) was stirred at 0° C. A solution of methyl 2,3-dichlorobenzoate (49 g, 0.244 mol) in THF (50 mL) was added dropwise into the above mixture at 0-5° C. Then the mixture was stirred at room temperature for 2 h. The reaction mixture was quenched with ethyl acetate (15 mL), water (7.5 mL), 15% NaOH (7.5 mL) and water (22.5 mL), filtered and the filtrate was concentrated. The resulting residue was dissolved with DCM (500 mL) and washed with brine. The organic layer was dried over Na₂SO₄, filtered and the filtrate was concentrated to provide the titled compound (37 g, 88%), as a white solid; ¹H NMR (300 MHz, CDCl₃) δ ppm 4.81 (d, J=6.3 Hz, 2H), 7.24 (t, J=7.8 Hz, 1H), 7.42-7.45 (m, 2H).

c) 1-(bromomethyl)-2,3-dichlorobenzene

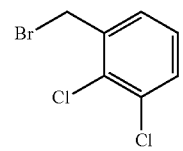

To a solution of (2,3-dichlorophenyl)methanol (75 g, 0.431 mol), in toluene (800 mL), tribromophosphine (40.7 g, 0.151 mol) was added dropwise at room temperature with stirring. Then the reaction mixture was stirred at room temperature for 2 h and concentrated. The resulting residue was neutralized with aq. NaHCO₃ and extracted with DCM (300 mL*3). The organic layer was washed with brine, dried over Na₂SO₄, filtered and the filtrate was concentrated to provide the titled compound (84.7 g, 83%), as a deep red solid.

d) ethyl 2-cyano-3-(2,3-dichlorophenyl)propanoate

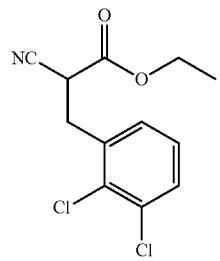 [SMILES: CCOC(=O)C(C#N)Cc1cccc(Cl)c1Cl]

A mixture of 1-(bromomethyl)-2,3-dichlorobenzene (82 g, 0.34 mol), ethyl 2-cyanoacetate (82 g, 0.34 mol) and K₂CO₃ (187.7 g, 1.36 mol) in THF (1.5 L), was stirred at 60° C. for 16 h. The reaction mixture was cooled and adjusted pH to 2-3 with 4N aq. HCl. The mixture was diluted with water (1 L) and extracted with ethyl acetate (400 mL*3). The combined organic layers were washed with brine, dried over Na₂SO₄, filtered and the filtrate was concentrated. The resulting residue was purified by silica gel chromatography eluted with PE:EA=15:1 to provide the titled compound (45 g, 48%), as a white solid; ¹H NMR (300 MHz, CDCl₃) δ ppm 1.32 (t, J=7.2 Hz, 3H), 3.23 (dd, J=9.6, 13.8 Hz, 1H), 3.56 (dd, J=6.0, 13.8 Hz, 1H), 3.91 (dd, J=6.0, 9.6 Hz, 1H), 4.28 (q, J=7.2 Hz, 2H), 7.21 (t, J=7.8 Hz, 1H), 7.28 (dd, J=1.8, 7.5 Hz, 1H), 7.45 (dd, J=1.8, 7.8 Hz, 1H).

e) 3-amino-4-(2,3-dichlorobenzyl)-1H-pyrazol-5-ol

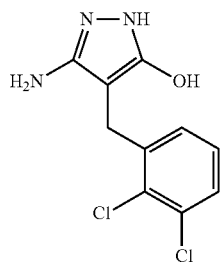 [SMILES: Nc1n[nH]c(O)c1Cc1cccc(Cl)c1Cl]

A mixture of ethyl 2-cyano-3-(2,3-dichlorophenyl)propanoate (30 g, 0.11 mol) and hydrazine hydrate (11 g, 0.22 mol) in ethanol (300 mL), was stirred under reflux for 16 h. The reaction mixture was cooled and filtered to provide the titled compound (19 g) and the filtrate was concentrated to provide the crude titled compound (18 g); LC/MS: MS (ES+) m/e 258 (MH+); $^1$H NMR (300 MHz, DMSO-$d_6$) δ ppm 3.47 (s, 2H), 4.12 (s, 2H), 7.02 (dd, J=1.5, 7.8 Hz, 1H), 7.23 (t, J=7.8 Hz, 1H), 7.36 (s, 1H), 7.44 (dd, J=1.5, 7.8 Hz, 1H), 9.06 (s, 1H).

f) 2-(4-(2,3-dichlorobenzyl)-3-hydroxy-1H-pyrazol-5-yl)isoindoline-1,3-dione

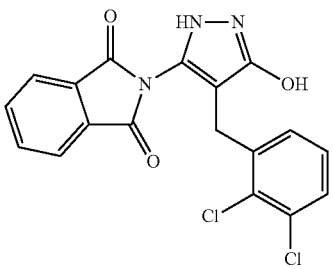 [SMILES: O=C1c2ccccc2C(=O)N1c1[nH]nc(O)c1Cc1cccc(Cl)c1Cl]

A mixture of 3-amino-4-(2,3-dichlorobenzyl)-1H-pyrazol-5-ol (18 g, 70 mmol) and isobenzofuran-1,3-dione (20 g, 140 mmol) in acetic acid (100 mL), was stirred under reflux for 16 h. The reaction mixture was cooled and filtered to provide the titled compound (13 g, 50%); LC/MS: MS (ES+) m/e 388 (MH+); $^1$H NMR (300 MHz, DMSO-$d_6$) δ ppm 3.66 (s, 2H), 7.20-7.31 (m, 2H), 7.51 (d, J=7.5 Hz, 1H), 7.99-8.02 (m, 2H), 8.11 (s, 2H), 8.25-8.28 (m, 2H).

g) 2-(4-(2,3-dichlorobenzyl)-3-methoxy-1H-pyrazol-5-yl)isoindoline-1,3-dione

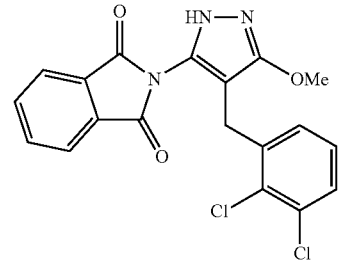 [SMILES: COc1n[nH]c(N2C(=O)c3ccccc3C2=O)c1Cc1cccc(Cl)c1Cl]

A mixture of DIAD (1.14 g, 5.67 mmol), PPh$_3$ (1.49 g, 5.67 mmol) and methanol (0.18 g, 5.67 mmol) in THF (30 mL) was stirred at 0° C. for 1 h. Then, the mixture was added dropwise to a solution of 2-(4-(2,3-dichlorobenzyl)-3-hydroxy-1H-pyrazol-5-yl)isoindoline-1,3-dione (2 g, 5.15 mmol) in THF (500 mL) and DCM (500 mL), and the mixture was stirred at room temperature for 2 h. It was quenched with water (50 mL), and the solvent was evaporated in vacuo to dryness. The residue was purified by silica gel chromatography eluted with EA:PE=1:1 to give the titled compound (620 mg, 30%) as a white solid. LC/MS: MS (ES+) m/e 402 (MH+); $^1$H NMR (300 MHz, DMSO-$d_6$) δ ppm 3.74 (s, 2H), 3.84 (s, 3H), 7.08 (d, J=4.8 Hz, 2H), 7.27-7.31 (m, 1H), 7.94 (s, 5H), 12.27 (s, 1H).

h) 4-(2,3-dichlorobenzyl)-5-methoxy-1H-pyrazol-3-amine

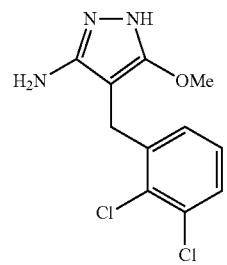 [SMILES: COc1[nH]nc(N)c1Cc1cccc(Cl)c1Cl]

To a solution of 2-(4-(2,3-dichlorobenzyl)-3-methoxy-1H-pyrazol-5-yl)isoindoline-1,3-dione (620 mg, 1.54 mmol) in THF (20 mL) was added hydrazine hydrate (1.0 g, 20 mmol) dropwise with stirring at room temperature. Then, the mixture was stirred at room temperature for 2 hours and 50° C. for another 2 hours. Then the reaction mixture was concentrated under vacuo and the residue was purified by silica gel chromatography eluted with EA to give the titled compound (301 mg, 72%) as a colorless viscous liquid. LC/MS: MS (ES+) m/e 272 (MH+); $^1$H NMR (300 MHz, CDCl$_3$) δ ppm 3.71 (s, 2H), 3.86 (s, 3H), 7.07-7.14 (m, 2H), 7.29-7.32 (m, 1H).

i) 3-(2,3-dichlorobenzyl)-2-methoxy-5-(pyridin-4-yl)pyrazolo[1,5-a]pyrimidin-7-ol A solution of 4-(2,3-dichlorobenzyl)-5-methoxy-1H-pyrazol-3-amine (301 mg, 1.1 mmol) and ethyl 3-oxo-3-(pyridin- 4-yl)propanoate (223 mg, 1.15 mmol) in acetic acid (15 mL) was stirred at 100° C. for 4 h. Then the reaction mixture was concentrated under vacuo and the residue was purified by silica gel chromatography eluted with EA to EA/MeOH=4/1, and further recrystallized with DMSO/H$_2$O to give the titled compound (57 mg, 13%) as a yellowish solid. LC/MS: MS (ES$^+$) m/e 402 (MH$^+$); $^1$H NMR (300 MHz, DMSO-d$_6$) δ ppm 3.89 (s, 3H), 4.00 (s, 2H), 6.07 (s, 1H), 7.03 (d, J=8.4 Hz, 1H), 7.25 (t, J=8.4 Hz, 1H), 7.48 (d, J=8.4 Hz, 1H), 7.79 (d, J=5.1 Hz, 2H), 8.71 (d, J=5.1 Hz, 2H), 12.15 (s, 1H).

Example 36

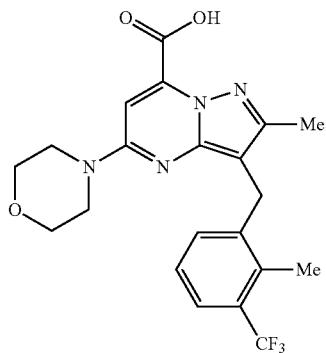 [SMILES: Cc1nn2c(C(=O)O)cc(N3CCOCC3)nc2c1Cc1cccc(C(F)(F)F)c1C]

Preparation of 2-methyl-3-(2-methyl-3-(trifluoromethyl)benzyl)-5-morpholinopyrazolo[1,5-a]pyrimidine-7-carboxylic acid To a solution of 7-chloro-2-methyl-3-{[2-methyl-3-(trifluoromethyl)phenyl]methyl}-5-(4-morpholinyl)pyrazolo[1,5-a]pyrimidine (2.82 g, 6.64 mmol), prepared using the same procedure used to prepare Example 10, in N,N-Dimethylformamide (50 mL) and methanol (34.1 mL, 843 mmol) was added palladium(II) acetate (0.224 g, 0.996 mmol), DPPF (0.552 g, 0.996 mmol). The reaction mixture was purged with carbon monoxide for 5 min and then TEA (2.78 mL, 19.91 mmol) was added in. The reaction mixture was stirred at 70° C. under CO atmosphere for 6 h. Additional palladium(II) acetate (0.224 g, 0.996 mmol) and DPPF (0.552 g, 0.996 mmol) was added in. The reaction mixture was purged with carbon monoxide for 5 min and then TEA (2.78 mL, 19.91 mmol) was added in. The reaction mixture was stirred at 70° C. under CO atmosphere for 16 h. The reaction was filtered through Celite, and the filtrate was concentrated. The residue was dissolved in Tetrahydrofuran (THF) (100 mL). To the solution of residue in THF was added sodium hydroxide (5.31 mL, 26.6 mmol). The reaction mixture was stirred at rt for 2 h. Water (50 mL) was added in. The reaction was acidified with 5 N HCl, then extracted with DCM (500 mL×3), dried and concentrated. The crude was purified on a silica column (EtOAc/Hexane: 20~60%) to give the product (1.6 g, 53%). $^1$H NMR (400 MHz, DMSO-d$_6$) δ ppm 2.23 (s, 3H) 2.44 (s, 3H) 3.50-3.62 (m, 4H) 3.62-3.71 (m, 4H) 3.97 (s, 2H) 6.98 (s, 1H) 7.22-7.33 (m, 1H) 7.38 (d, J=7.58 Hz, 1H) 7.52 (d, 1H), 14.60 (b.s., 1H); LC/MS: MS (ES+) m/e 435.4 [M+H]$^+$.

Example 37

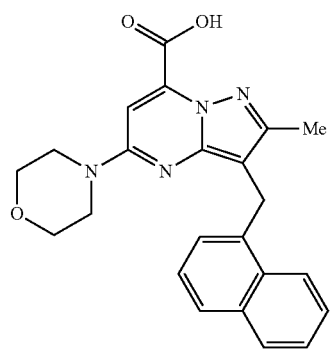 [SMILES: Cc1nn2c(C(=O)O)cc(N3CCOCC3)nc2c1Cc1cccc2ccccc12]

Preparation of 2-methyl-5-morpholino-3-(naphthalen-1-ylmethyl)pyrazolo[1,5-a]pyrimidine-7-carboxylic acid a) 4-(7-chloro-2-methyl-3-(naphthalen-1-ylmethyl)pyrazolo[1,5-a]pyrimidin-5-yl)morpholine

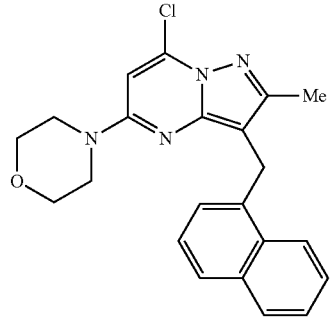 [SMILES: Cc1nn2c(Cl)cc(N3CCOCC3)nc2c1Cc1cccc2ccccc12]

To the solution of 5,7-dichloro-2-methyl-3-(1-naphthalenylmethyl)pyrazolo[1,5-a]pyrimidine (1.5 g, 4.38 mmol) in Tetrahydrofuran (THF) (40 mL) was added sodium hydroxide (21.92 mL, 43.8 mmol). The reaction was stirred at rt for 18 h and heated at 50° C. for 7 h. The reaction was concentrated and acidified. The reaction mixture was extracted with EtOAc (80 mL×2). The organic phases were combined, dried and concentrated. The mixture was transferred to a 20 mL MW vial. Morpholine (1.909 mL, 21.92 mmol) and Ethanol (2 mL) was added in. The mixture was subjected to MW irradiation at 150° C. for 3 h. Water (10 mL) was added to the reaction mixture which was acidified with 6 N HCl. The reaction was extracted with EtOAc (100 mL×3). The organic phases were combined, dried and concentrated. To the resulted solid was added POCl$_3$ (6.13 mL, 65.7 mmol) and N,N-diethylaniline (1.308 g, 8.77 mmol). The reaction was heated at 90° C. for 5 h. The reaction was cooled down. Crushed ice was added in. The aqueous mixture was extracted with EtOAc (100 mL×3). The organic phases were combined, dried and concentrated. The crude was purified on silica column (EtOAc/Hexane: 20~40%) to give the product (1.02 g, 59%). $^1$H NMR (400 MHz, DMSO-d$_6$) δ ppm 2.20 (s, 3H)

3.54-3.74 (m, 8H) 4.33 (s, 2H) 7.00 (s, 1H) 7.32 (d, J=6.57 Hz, 1H) 7.37-7.44 (m, 1H) 7.45-7.55 (m, 2H) 7.76 (d, J=8.08 Hz, 1H) 7.90 (m, 1H) 8.44 (m, 1H); LC/MS: MS (ES+) m/e 393.1 [M+H]$^+$.

b) 2-methyl-5-morpholino-3-(naphthalen-1-ylmethyl)pyrazolo[1,5-a]pyrimidine-7-carboxylic acid To the solution of 7-chloro-2-methyl-5-(4-morpholinyl)-3-(1-naphthalenylmethyl)pyrazolo[1,5-a]pyrimidine (0.8 g, 2.036 mmol) in N,N-Dimethylformamide (25 mL) and methanol (8 mL, 198 mmol) was added PdCl$_2$(PPh$_3$)$_3$ (0.143 g, 0.204 mmol). The mixture was purged with carbon monoxide for 5 min and then TEA (0.851 mL, 6.11 mmol) was added in. The reaction mixture was stirred at 70° C. under CO atmosphere for 14 h. Very little product was detected. To the reaction mixture was added additional palladium(II) acetate (0.078 g, 0.346 mmol) and DPPF (0.192 g, 0.346 mmol). The mixture was purged with carbon monoxide for 5 min and then TEA (0.851 mL, 6.11 mmol) was added in. The reaction mixture was stirred at 70° C. under CO atmosphere for 6 h. Palladium(II) acetate (0.078 g, 0.346 mmol) and DPPF (0.192 g, 0.346 mmol) was added in. The mixture was purged with carbon monoxide for 5 min and then TEA (0.851 mL, 6.11 mmol) was added in. The reaction mixture was stirred at 70° C. under CO atmosphere for 14 h. The reaction mixture was filtered through Celite, and the filtrate was concentrated. To the solution of the residue in Tetrahydrofuran (THF) (25 ml) was added sodium hydroxide (8.14 mL, 8.14 mmol). The reaction mixture was stirred at rt for 2 h. The reaction was acidified with 1 N HCl, then extracted with EtOAc (30 mL×2). The combined organic phases were dried and concentrated. The crude was purified on silica column (MeOH/DCM: 0~10%) then reversed phase HPLC (27~57% CH3CN (0.1% TFA)/Water (0.1% TFA)) to give the titled product (0.2 g, 23%). $^1$H NMR (400 MHz, DMSO-d$_6$) δ ppm 2.24 (s, 3H) 3.67 (m, 8H) 4.35 (s, 2H) 7.01 (s, 1H) 7.24-7.57 (m, 4 H) 7.68-7.85 (m, 1H) 7.83-7.96 (m, 1H) 8.42 (m, 1H); LC/MS: MS (ES+) m/e 403.2 [M+H]$^+$.

Example 38

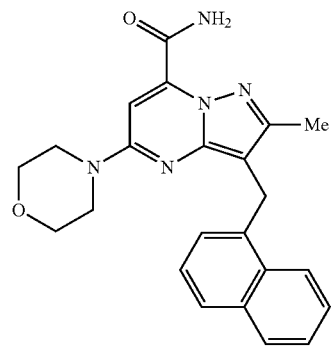 [SMILES: Cc1nn2c(C(N)=O)cc(N3CCOCC3)nc2c1Cc1cccc2ccccc12]

Preparation of 2-methyl-5-morpholino-3-(naphthalen-1-ylmethyl)pyrazolo[1,5-a]pyrimidine-7-carboxamide To the mixture of 2-methyl-5-(4-morpholinyl)-3-(1-naphthalenylmethyl)pyrazolo[1,5-a]pyrimidine-7-carboxylic acid (120 mg, 0.298 mmol) in Dichloromethane (DCM) (5 mL) was added oxalyl chloride (0.157 mL, 1.789 mmol) and two drops of DMF. The reaction was stirred at rt for 10 minutes and concentrated to give the acid chloride. To the crude acid chloride was added Tetrahydrofuran (THF) (5 mL). The reaction was bubbled with NH$^3$ gas. The reaction was stirred at rt for 10 min. Brine (5 mL) and EtOAc (20 mL) was added in. The aqueous phase was extracted with EtOAc (20 mL). The organic phases were dried and concentrated. The crude was purified on silica column (EtOAc/Hexane: 20~30%) to give the product (94 mg, 75%). $^1$H NMR (400 MHz, DMSO-d$_6$) δ ppm 2.26 (s, 3H) 3.53-3.78 (m, 8H) 4.37 (s, 2H) 7.16 (s, 1H) 7.29-7.56 (m, 4H) 7.77 (d, J=8.08 Hz, 1H) 7.84-7.96 (m, 1H) 8.38-8.49 (m, 1H) 8.54 (br. s., 1H) 9.65 (br. s., 1H); LC/MS: MS (ES+) m/e 402.0 [M+H]$^+$.

Example 39

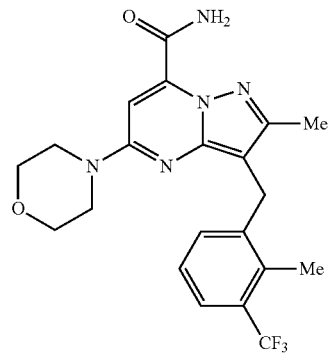

Preparation of 2-methyl-3-(2-methyl-3-(trifluoromethyl)benzyl)-5-morpholinopyrazolo[1,5-a]pyrimidine-7-carboxamide To the mixture of 2-methyl-3-{[2-methyl-3-(trifluoromethyl)phenyl]methyl}-5-(4-morpholinyl)pyrazolo[1,5-a]pyrimidine-7-carboxylic acid (1.6 g, 3.68 mmol) in Dichloromethane (DCM) (20 mL) was added oxalyl chloride (2.58 mL, 29.5 mmol) and followed by the addition of two drops of DMF. The reaction was stirred at rt for 10 minutes and concentrated. To the crude acid chloride was added Tetrahydrofuran (THF) (20 mL). The reaction was bubbled with NH$_3$ gas. The reaction was stirred at rt for 10 minutes. Brine (5 mL) and EtOAc (150 mL) was added in. The aqueous phase was extracted with EtOAc (150 mL). The organic phases were combined and concentrated (1.6 g, 95%). $^1$H NMR (400 MHz, DMSO-d$_6$) δ ppm 2.26 (s, 3H) 2.44 (s, 3H) 3.55-3.62 (m, 4H) 3.63-3.69 (m, 4H) 3.99 (s, 2H) 7.14 (s, 1H) 7.25-7.32

(m, 1H) 7.38 (d, J=7.58 Hz, 1H) 7.52 (d, J=7.33 Hz, 1H) 8.54 (br. s., 1H) 9.66 (br. s., 1H); LC/MS: MS (ES+) m/e 434.2 [M+H]⁺.

Example 40

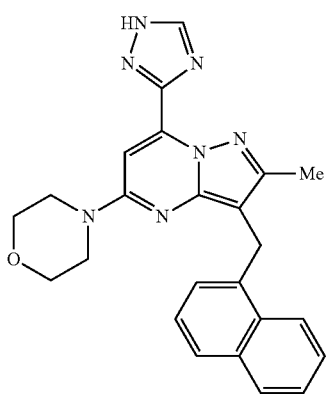

Preparation of 4-(2-methyl-3-(naphthalen-1-ylmethyl)-7-(1H-1,2,4-triazol-3-yl)pyrazolo[1,5-a]pyrimidin-5-yl)morpholine A mixture of 2-methyl-5-(4-morpholinyl)-3-(1-naphthalenylmethyl)pyrazolo[1,5-a]pyrimidine-7-carboxamide (55 mg, 0.137 mmol) in N,N-dimethylformamide dimethyl acetal (2 mL, 14.94 mmol) was stirred at 105° C. for 3 days and concentrated to give the crude. To the crude was added Acetic Acid (2 mL) and hydrazine hydrate (0.047 mL, 0.959 mmol). The reaction mixture was heated at 100° C. for 1 h and concentrated. Brine (10 mL) and EtOAc (20 mL) was added in. The aqueous phase was extracted with EtOAc (20 mL×4). The organic phases were combined and concentrated. The crude was purified on silica column (EtOAc/Hexane: 10~40%) to give the product (20 mg, 33%). ¹H NMR (400 MHz, DMSO-d₆) δ ppm 2.27 (s, 3H) 3.56-3.82 (m, 8H) 4.39 (s, 2H) 7.14 (s, 1H) 7.29-7.59 (m, 4H) 7.77 (d, J=8.08 Hz, 1H) 7.85-7.98 (m, 1H) 8.38-8.61 (m, 2H); LC/MS: MS (ES+) m/e 426.0 [M+H]⁺.

Example 41

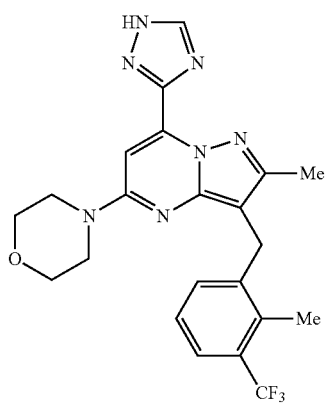 [SMILES: Cc1nn2c(-c3nc[nH]n3)cc(N3CCOCC3)nc2c1Cc1cccc(C(F)(F)F)c1C]

Preparation of 4-(2-methyl-3-(2-methyl-3-(trifluoromethyl)benzyl)-7-(1H-1,2,4-triazol-3-yl)pyrazolo[1,5-a]pyrimidin-5-yl)morpholine A mixture of 2-methyl-3-{[2-methyl-3-(trifluoromethyl)phenyl]methyl}-5-(4-morpholinyl)pyrazolo[1,5-a]pyrimidine-7-carboxamide (0.45 g, 1.038 mmol) in N,N-dimethylformamide dimethyl acetal (15 mL, 112 mmol) was stirred at 105° C. for 18 h. The reaction mixture was concentrated. To the crude material was added Acetic Acid (10 mL) and hydrazine monohydrate (0.228 mL, 7.27 mmol). The reaction mixture was heated at 100° C. for 1 h and concentrated. The crude material was purified on a silica column (EtOAc/Hexane: 20~60%). The product is inseparable with the side product. To the mixture was added THF (30 mL) and sodium hydroxide (2.076 mL, 2.076 mmol). The reaction mixture was stirred at rt for 2 h. EtOAc (100 mL) was added in. The reaction was acidified with 1 N HCl. The aqueous phase was extracted with EtOAc (100 mL×2). The organic phases were combined, dried (MgSO₄) and concentrated. The crude was purified on silica column (eluting with EtOAc/Hexane: 20~60%) then (5% MeOH/DCM) to give the product (0.23 g, 46%). ¹H NMR (400 MHz, DMSO-d₆) δ ppm 2.27 (s, 3H) 2.46 (s, 3H) 3.50-3.76 (m, 8H) 4.00 (s, 2H) 7.13 (br. s., 1H) 7.21-7.33 (m, 1H) 7.41 (d, J=7.58 Hz, 1H) 7.52 (d, J=7.83 Hz, 1H) 8.54 (br. s., 1H) 14.55 (br. s., 1H); LC/MS: MS (ES+) m/e 458.2 [M+H]⁺.

Example 42

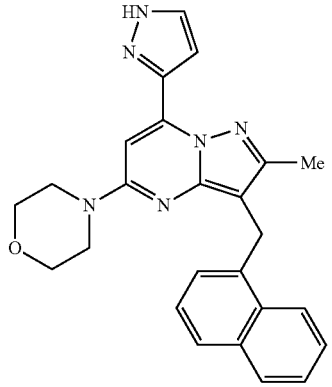 [SMILES: Cc1nn2c(-c3cc[nH]n3)cc(N3CCOCC3)nc2c1Cc1cccc2ccccc12]

Preparation of 4-(2-methyl-3-(naphthalen-1-ylmethyl)-7-(1H-pyrazol-3-yl)pyrazolo[1,5-a]pyrimidin-5-yl)morpholine In 5 mL MW vial was added in 7-chloro-2-methyl-5-(4-morpholinyl)-3-(1-naphthalenylmethyl)pyrazolo[1,5-a]pyrimidine (70 mg, 0.178 mmol), 1H-pyrazol-3-ylboronic acid (59.8 mg, 0.535 mmol), PdCl₂(dppf)-CH₂Cl₂ adduct (17.46 mg, 0.021 mmol) and potassium carbonate (98 mg, 0.713 mmol) in 1,2-Dimethoxyethane (DME) (1.6 mL) and Water (0.400 mL). The reaction vessel was heated with microwave irradiation at 140° C. for 15 min. LC-MS showed 15% conversion. 1H-pyrazol-3-ylboronic acid (59.8 mg, 0.535 mmol) and PdCl₂(dppf)-CH₂Cl₂ adduct (17.46 mg, 0.021 mmol) was added in. The reaction vessel was heated with microwave irradiation at 140° C. for 35 min. LC-MS showed 50% conversion. 1H-pyrazol-3-ylboronic acid (59.8 mg, 0.535 mmol), potassium carbonate (98 mg, 0.713 mmol) and PdCl₂

(dppf)-CH₂Cl₂ adduct (17.46 mg, 0.021 mmol) was added in. The reaction vessel was heated with microwave irradiation at 140° C. for 50 min. The reaction mixture was filtered through celite and washed with EtOAc (50 mL). The organic phase was washed with brine (10 mL). The aqueous phase was extracted with DCM (20 mL). The organic phases were combined, dried (MgSO₄) and concentrated. The crude was purified on silica column (EtOAc/Hexane: 20~40%) to give the product (16 mg, 20%). ¹H NMR (400 MHz, DMSO-d₆) δ ppm 2.26 (s, 3H) 3.61-3.79 (m, 8H) 4.38 (s, 2H) 7.12 (br. s., 1H) 7.33-7.46 (m, 2H) 7.46-7.53 (m, 2H) 7.57 (d, J=2.27 Hz, 1H) 7.76 (d, J=8.08 Hz, 1H) 7.86-8.00 (m, 2H) 8.46-8.55 (m, 1H). LC/MS: MS (ES+) m/e 425.0 [M+H]⁺.

Example 43

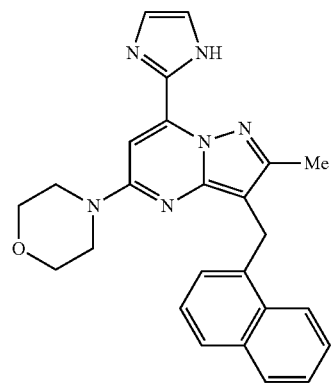 [SMILES: Cc1nn2c(-c3ncc[nH]3)cc(N3CCOCC3)nc2c1Cc1cccc2ccccc12]

Preparation of 4-(7-(1H-imidazol-2-yl)-2-methyl-3-(naphthalen-1-ylmethyl)pyrazolo[1,5-a]pyrimidin-5-yl)morpholine Three 5 mL microwave vials were charged 7-chloro-2-methyl-5-(4-morpholinyl)-3-(1-naphthalenylmethyl) pyrazolo[1,5-a]pyrimidine (50 mg, 0.127 mmol), imidazole (130 mg, 1.909 mmol), potassium iodide (42.3 mg, 0.255 mmol), copper(I) iodide (48.5 mg, 0.255 mmol) and palladium(II) acetate (8.57 mg, 0.038 mmol) in N,N-Dimethylformamide (DMF) (0.75 mL). The reaction was purged with nitrogen, sonicated for 3 min and subjected to microwave irradiation at 185° C. for 10 min. The reactions were combined and filtered through a pad of celite. The filter pad was washed with DCM (10 mL×4), and the filtrate was concentrated. Two products with same molecular weight were detected. The residue was purified by reversed phase HPLC (10~90% CH3CN (0.1% TFA)/Water (0.1% TFA)) to give the product (18 mg, 11%). ¹H NMR (400 MHz, DMSO-d₆) δ ppm 2.34 (s, 3H) 3.68 (m, 4H) 3.70-3.76 (m, 4H) 4.39 (s, 2H) 7.17-7.55 (m, 7H) 7.77 (d, J=8.08 Hz, 1H) 7.86-7.94 (m, 1H) 8.45-8.53 (m, 1H) 12.95 (s, 1H); LC/MS: MS (ES+) m/e 425.0 [M+H]⁺.

Example 44

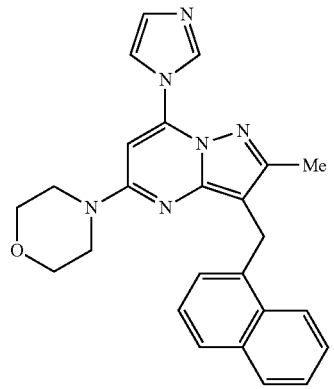 [SMILES: Cc1nn2c(-n3ccnc3)cc(N3CCOCC3)nc2c1Cc1cccc2ccccc12]

Preparation of 4-(7-(1H-imidazol-1-yl)-2-methyl-3-(naphthalen-1-ylmethyl)pyrazolo[1,5-a]pyrimidin-5-yl)morpholine A 20 mL microwave vial was charged with 7-chloro-2-methyl-5-(4-morpholinyl)-3-(1-naphthalenylmethyl) pyrazolo[1,5-a]pyrimidine (200 mg, 0.509 mmol), imidazole (243 mg, 3.56 mmol), potassium phosphate (324 mg, 1.527 mmol), copper(I) iodide (58.2 mg, 0.305 mmol) and (1R,2R)-diaminomethylcyclohexane (87 mg, 0.611 mmol) in 1,4-Dioxane (5 mL). The reaction was purged with nitrogen and sealed. The reaction mixture was stirred at 100° C. for 5 days. After cooling the reaction, EtOAc (30 mL) was added in. The reaction was filtered and the filtrate was washed with brine (10 mL×3), dried (MgSO₄) and concentrated to give the crude. The residue was purified on silica column (EtOAc/Hexane: 20~60%), then (0~3% MeOH/DCM) to give the product (32 mg, 14%). ¹H NMR (400 MHz, DMSO-d₆) δ ppm 2.24 (s, 3H) 3.71 (s, 8H) 4.37 (s, 2H) 6.90 (s, 1H) 7.19 (s, 1H) 7.30-7.60 (m, 4H) 7.77 (d, J=7.83 Hz, 1H) 7.84-7.97 (m, 1H) 8.08 (t, J=1.39 Hz, 1H) 8.35-8.55 (m, 1H) 8.70 (s, 1H); LC/MS: MS (ES+) m/e 425.0 [M+H]⁺.

Example 45

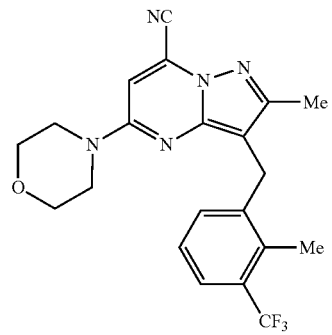 [SMILES: Cc1nn2c(C#N)cc(N3CCOCC3)nc2c1Cc1cccc(C(F)(F)F)c1C]

Preparation of 2-methyl-3-(2-methyl-3-(trifluoromethyl)benzyl)-5-morpholinopyrazolo[1,5-a]pyrimidine-7-carbonitrile To the solution of 2-methyl-3-{[2-methyl-3-(trifluoromethyl)phenyl]methyl}-5-(4-morpholinyl)pyrazolo[1,5-a]pyrimidine-7-carboxamide (200 mg, 0.461 mmol) in N,N-Dimethylformamide (DMF) (6 mL) was added thionyl chloride (0.067 mL, 0.923 mmol). The reaction mixture was stirred at rt for 2 h. Water was added in. The solid precipitated. Filtration gave the crude product. The crude was purified on silica column (20~50% EtOAc/Hexane) to give the titled product (0.14 g, 77%). MS (ES+) m/e 416.2 [M+H]+.

Example 46

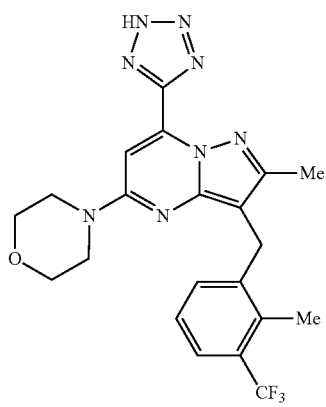 [SMILES: Cc1nn2c(-c3nn[nH]n3)cc(N3CCOCC3)nc2c1Cc1cccc(C(F)(F)F)c1C]

Preparation of 4-(2-methyl-3-(2-methyl-3-(trifluoromethyl)benzyl)-7-(2H-tetrazol-5-yl)pyrazolo[1,5-a]pyrimidin-5-yl)morpholine To a 5 mL microwave vial was added in 2-methyl-3-{[2-methyl-3-(trifluoromethyl)phenyl]methyl}-5-(4-morpholinyl)pyrazolo[1,5-a]pyrimidine-7-carbonitrile (68 mg, 0.164 mmol), sodium azide (85 mg, 1.310 mmol) and ammonium chloride (70.0 mg, 1.310 mmol) in N,N-Dimethylformamide (DMF) (1 mL). The reaction was subjected to microwave irradiation at 180° C. for 15 min. The reaction mixture was added to a saturated NH4Cl solution and extracted with DCM (30 mL×2). The combined organic phases were dried and concentrated. The residue was purified on silica column (20~60% EtOAc/Hexane) and then (5% MeOH/DCM) to give the titled product (32 mg, 41%). 1H NMR (400 MHz, DMSO-d6) δ ppm 2.29 (s, 3H) 2.46 (s, 3H) 3.47-3.79 (m, 8H) 4.01 (s, 2H) 7.15-7.34 (m, 2H) 7.40 (d, J=8.15 Hz, 1H) 7.53 (d, J=7.74 Hz, 1H); LC/MS: MS (ES+) m/e 459.3 [M+H]+.

Example 47

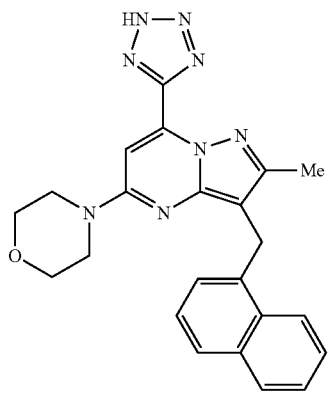 [SMILES: Cc1nn2c(-c3nn[nH]n3)cc(N3CCOCC3)nc2c1Cc1cccc2ccccc12]

Preparation of 4-(2-methyl-3-(naphthalen-1-ylmethyl)-7-(1H-tetrazol-5-yl)pyrazolo[1,5-a]pyrimidin-5-yl)morpholine a) 2-methyl-5-(4-morpholinyl)-3-(1-naphthalenylmethyl)pyrazolo[1,5-a]pyrimidine-7-carbonitrile

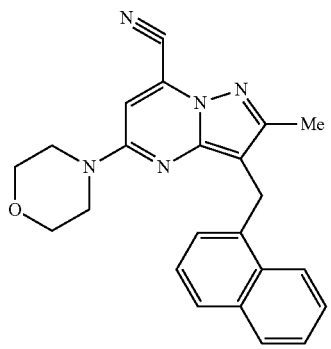 [SMILES: Cc1nn2c(C#N)cc(N3CCOCC3)nc2c1Cc1cccc2ccccc12]

To the solution of 2-methyl-5-(4-morpholinyl)-3-(1-naphthalenylmethyl)pyrazolo[1,5-a]pyrimidine-7-carboxamide (0.2 g, 0.498 mmol) in N,N-Dimethylformamide (DMF) (4 mL) was added thionyl chloride (0.055 mL, 0.747 mmol). The reaction was stirred at rt for 1 h. Additional thionyl chloride (0.055 mL, 0.747 mmol) was added in. The reaction was stirred at rt for 1 h. Water was added in. The solid precipitated. Filtration gave the crude product. The crude was purified on silica column (20~50% EtOAc/Hexane) to give the product (0.06 g, 31%). 1H NMR (400 MHz, DMSO-d6) δ ppm 2.25 (s, 3H) 3.58-3.72 (m, 8H) 4.34 (s, 2H) 7.30 (d, J=7.07 Hz, 1H) 7.36-7.45 (m, 1H) 7.46-7.54 (m, 2H) 7.58 (s, 1H) 7.77 (d, J=7.83 Hz, 1H) 7.83-7.95 (m, 1H) 8.40 (d, 1H); LC/MS: MS (ES+) m/e 384.2 [M+H]+.

b) 4-(2-methyl-3-(naphthalen-1-ylmethyl)-7-(1H-tetrazol-5-yl)pyrazolo[1,5-a]pyrimidin-5-yl)morpholine In a 5 mL microwave vial was added in 2-methyl-5-(4-morpholinyl)-3-(1-naphthalenylmethyl)pyrazolo[1,5-a]pyrimidine-7-carbonitrile (60 mg, 0.156 mmol), sodium azide (81 mg, 1.252 mmol) and ammonium chloride (67.0 mg, 1.252 mmol) in N,N-Dimethylformamide (DMF) (2 mL). The reaction was subjected to MW irradiation at 180° C. for 15 min. The reaction mixture was added to a saturated NH₄Cl solution and extracted with DCM (30 mL×2). The combined organic phases were dried and concentrated. The residue was purified on silica column (20~60% EtOAc/Hexane) and then (0~10% MeOH/DCM) to give the titled product (22 mg, 31%). ¹H NMR (400 MHz, DMSO-d₆) δ ppm 2.25 (s, 3H) 3.70 (m, 8H) 4.38 (s, 2H) 7.12 (br. s., 1H) 7.29-7.45 (m, 2H) 7.47-7.57 (m, 2H) 7.77 (d, J=8.08 Hz, 1H) 7.85-7.96 (m, 1H) 8.49 (m, 1H); LC/MS: MS (ES+) m/e 427.0 [M+H]⁺.

Example 48

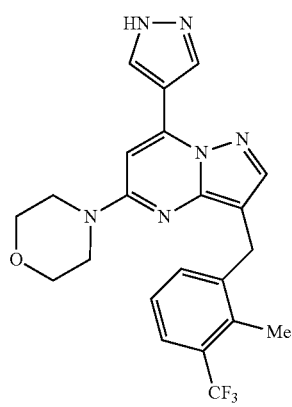 [SMILES: Cc1c(Cc2cnn3c(-c4cn[nH]c4)cc(N4CCOCC4)nc23)cccc1C(F)(F)F]

Preparation of 4-(3-(2-methyl-3-(trifluoromethyl)benzyl)-7-(1H-pyrazol-4-yl)pyrazolo[1,5-a]pyrimidin-5-yl)morpholine In a microwave vial was added Na₂CO₃ (0.049 mL, 0.097 mmol) was added to a suspension of 7-chloro-3-{[2-methyl-3-(trifluoromethyl)phenyl]methyl}-5-(4-morpholinyl)pyrazolo[1,5-a]pyrimidine (20 mg, 0.049 mmol), 1H-pyrazol-4-ylboronic acid (10.89 mg, 0.097 mmol), and PdCl₂(dppf) (3.56 mg, 4.87 µmol) in 1,4-Dioxane (0.6 mL). The reaction mixture was purged with N₂, sealed and irradiated with microwave at 150 C for 3 min (temp didn't reach to 150 C until at 7-8 min, total reaction time 10 min). LCMS showed complete reaction. The reaction mixture was concentrated, and the residue was loaded on a biotage column (10 g), which was eluted with 0-6% MeOH in DCM to give 17 mg (75%) of the product as a light brown solid. ¹H NMR (400 MHz, DMSO-d₆) δ ppm 2.51 (s, 3H), 3.72 (m, 4H), 3.87 (m, 4H), 4.11 (s, 2H), 6.60 (s, 1H), 7.21 (t, 1H), 7.52 (t, 2H), 7.75 (s, 1H), 8.67 (s, 2H); LC/MS: MS (ES+) m/e 443.2 [M+H]⁺.

Example 49

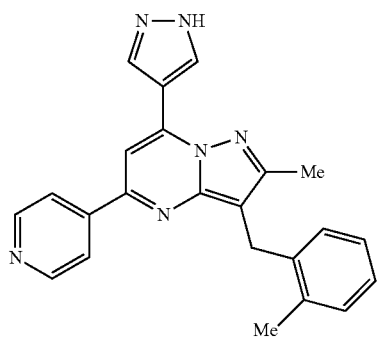 [SMILES: Cc1ccccc1Cc1c(C)nn2c(-c3cn[nH]c3)cc(-c3ccncc3)nc12]

Preparation of 2-methyl-3-(2-methylbenzyl)-7-(1H-pyrazol-4-yl)-5-(pyridin-4-yl)pyrazolo[1,5-a]pyrimidine Procedure: A mixture of 7-chloro-2-methyl-3-(2-methylbenzyl)-5-(pyridin-4-yl)pyrazolo[1,5-a]pyrimidine (170 mg, 0.5 mmol), 4-(4,4,5,5-tetramethyl-1,3,2-dioxaborolan-2-yl)-1H-pyrazole (120 mg, 0.6 mmol), Pd(dppf)Cl₂CH₂Cl₂ (40 mg, 0.05 mmol) and 2 N aq. Na₂CO₃ (5 mL) in dioxane (20 mL), was stirred at 80° C. overnight under a nitrogen atmosphere. The reaction mixture was cooled, concentrated. The resulting residue was purified by silica gel chromatography eluted with PE:EA=3:1 to provide the titled compound (165 mg, 87%), as a yellow solid; LC/MS: MS (ES⁺) m/e 381 (MH⁺); ¹H NMR (300 MHz, DMSO-d₆) δ ppm 2.41 (s, 6H), 4.15 (s, 2H), 7.05-7.12 (m, 3H), 7.14-7.19 (m, 1H), 8.12 (s, 1H), 8.25 (dd, J=1.2, 4.5 Hz, 2H), 8.78 (dd, J=1.2, 4.5 Hz, 2H), 8.87 (s, 1H), 9.19 (s, 1H), 13.62 (s, 1H).

Example 50

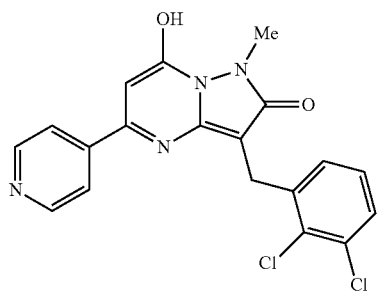 [SMILES: Cn1c(=O)c(Cc2cccc(Cl)c2Cl)c2nc(-c3ccncc3)cc(O)n21]

Preparation of 3-(2,3-dichlorobenzyl)-7-hydroxy-1-methyl-5-(pyridin-4-yl)pyrazolo[1,5-a]pyrimidin-2(1H)-one a) tert-butyl(4-(2,3-dichlorobenzyl)-5-hydroxy-1H-pyrazol-3-yl)carbamate

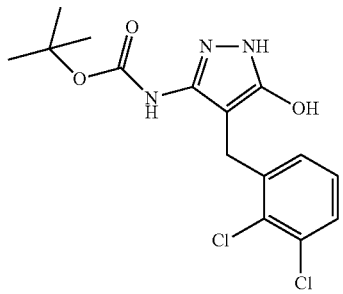 [SMILES: CC(C)(C)OC(=O)Nc1n[nH]c(O)c1Cc1cccc(Cl)c1Cl]

To a solution of 3-amino-4-(2,3-dichlorobenzyl)-1H-pyrazol-5-ol (258 mg, 1 mmol) and triethylamine (213 mg, 2.1 mol) in methanol (10 mL) was added (Boc)$_2$O (458 mg, 2.1 mmol) dropwise at room temperature with stirring. The reaction mixture was stirred at 45° C. for 16 h. Then the reaction mixture was cooled and filtered to provide the titled compound (167 mg, 47%), as a white solid; $^1$H NMR (300 MHz, DMSO-d$_6$) δ ppm 1.54 (s, 9H), 3.58 (s, 2H), 6.60 (s, 2H), 7.03 (d, J=7.8 Hz, 1H), 7.28 (t, J=7.8 Hz, 1H), 7.48 (d, J=7.8 Hz, 1H), 10.32 (s, 1H).

b) tert-butyl(4-(2,3-dichlorobenzyl)-5-hydroxy-1-methyl-1H-pyrazol-3-yl)carbamate

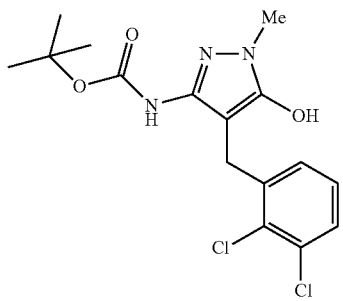 [SMILES: Cn1nc(NC(=O)OC(C)(C)C)c(Cc2cccc(Cl)c2Cl)c1O]

To a solution of tert-butyl(4-(2,3-dichlorobenzyl)-5-hydroxy-1H-pyrazol-3-yl)carbamate (160 mg, 0.447 mmol), triphenylphosphine (128 mg, 0.491 mol) and methanol (16 mg, 0.491 mol) in anhydrous THF (25 mL), a solution of DIAD (99 mg, 0.491 mmol) in anhydrous THF (2 mL) was added dropwise at 0° C. with stirring. The reaction mixture was stirred at room temperature for 1 h. The reaction mixture was concentrated. The resulting residue was purified by silica gel chromatography eluted with PE:EA=2:1 to provide the titled compound (50 mg, 30%), as a white solid; LC/MS: MS (ES$^+$) m/e 372 (MH$^+$); $^1$H NMR (300 MHz, DMSO-d$_6$) δ ppm 1.56 (s, 9H), 3.05 (s, 3H), 3.52 (s, 2H), 7.00 (d, J=7.8 Hz, 1H), 7.11 (s, 2H), 7.25 (t, J=7.8 Hz, 1H), 7.46 (d, J=7.8 Hz, 1H).

c) 3-amino-4-(2,3-dichlorobenzyl)-1-methyl-1H-pyrazol-5-ol

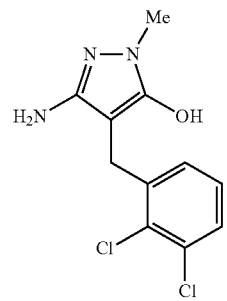 [SMILES: Cn1nc(N)c(Cc2cccc(Cl)c2Cl)c1O]

To a solution of tert-butyl(4-(2,3-dichlorobenzyl)-5-hydroxy-1-methyl-1H-pyrazol-3-yl)carbamate (15 g, 40 mmol) in DCM (150 mL), TFA (10 mL) was added dropwise at room temperature with stirring. The reaction mixture was stirred at room temperature overnight. Then the pH of the reaction mixture was adjusted to 10 with aq. Na$_2$CO$_3$, and extracted with DCM (100 mL*3). The combined organic layers were washed with brine, dried over Na$_2$SO$_4$, filtered and the filtrate was concentrated to provide the titled compound (7 g, 63%), as a white solid; LC/MS: MS (ES$^+$) m/e 272 (MH$^+$); $^1$H NMR (300 MHz, DMSO-d$_6$) δ ppm 2.90 (s, 3H), 3.45 (s, 2H), 6.06 (s, 2H), 7.01 (d, J=7.8 Hz, 1H), 7.25 (t, J=7.8 Hz, 1H), 7.45 (d, J=7.8 Hz, 1H), 8.95 (s, 1H).

d) 3-(2,3-dichlorobenzyl)-7-hydroxy-1-methyl-5-(pyridin-4-yl)pyrazolo[1,5-a]pyrimidin-2(1H)-one A mixture of 3-amino-4-(2,3-dichlorobenzyl)-1-methyl-1H-pyrazol-5-ol (150 mg, 0.551 mmol) and ethyl 3-oxo-3-(pyridin-4-yl)propanoate (128 mg, 0.662 mmol) in acetic acid (10 mL), was stirred under reflux for 6 h. The reaction mixture was cooled, concentrated. The resulting residue was purified by silica gel chromatography eluted with DCM:MeOH=10:1 to provide the titled compound (90 mg, 41%), as a white solid; LC/MS: MS (ES$^+$) m/e 401 (MH$^+$); $^1$H NMR (300 MHz, DMSO-d$_6$) δ ppm 3.55 (s, 3H), 3.82 (s, 2H), 6.07 (s, 1H), 7.12 (dd, J=1.2, 7.8 Hz, 1H), 7.26 (t, J=7.8 Hz, 1H), 7.50 (dd, J=1.2, 7.8 Hz, 1H), 7.71 (dd, J=1.8, 4.8 Hz, 2H), 7.76 (dd, J=1.8, 4.8 Hz, 1H), 11.94 (s, 1H).

Example 51

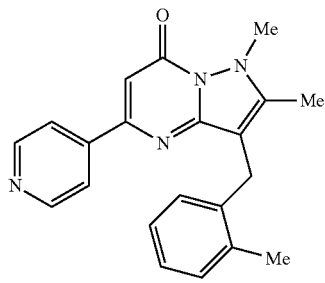 [SMILES: Cc1ccccc1Cc1c(C)n(C)n2c(=O)cc(-c3ccncc3)nc12]

Preparation of 1,2-dimethyl-3-(2-methylbenzyl)-5-(pyridin-4-yl)pyrazolo[1,5-a]pyrimidin-7(1H)-one To a solution of 2-methyl-3-(2-methylbenzyl)-5-(pyridin-4-yl)pyrazolo[1,5-a]pyrimidin-7(4H)-one acetate (500 mg, 1.281 mmol) in dichloromethane/methanol (30 mL/15 mL) was added trimethylsilyldiazomethane (1.3 mL, 2.561 mmol). The mixture was stirred at room temperature for 16 h. Then the mixture was concentrated under reduced pressure. The residue was purified by a silica gel chromatography to give the titled compound (223 mg, 51%); LC/MS: MS (ES+) m/e 345 (MH+); $^1$H NMR (300 MHz, CDCl$_3$) δ ppm 2.27 (s, 3H), 2.42 (s, 3H), 4.04 (s, 2H), 4.24 (s, 3H), 6.51 (s, 1H), 7.10-7.20 (m, 4H), 7.88 (d, J=5.7 Hz, 2H), 8.70 (d, J=5.7 Hz, 2H).

Exemplary Capsule Composition

An oral dosage form for administering the present invention is produced by filing a standard two piece hard gelatin capsule with the ingredients in the proportions shown in Table I, below.

TABLE I

| INGREDIENTS | AMOUNTS |
| --- | --- |
| Compound of example 1 | 25 mg |
| Lactose | 55 mg |
| Talc | 16 mg |
| Magnesium Stearate | 4 mg |

Exemplary Injectable Parenteral Composition

An injectable form for administering the present invention is produced by stirring 1.5% by weight of compound of example 1 in 10% by volume propylene glycol in water.

Exemplary Tablet Composition

The sucrose, calcium sulfate dihydrate and an PI3K inhibitor as shown in Table II below, are mixed and granulated in the proportions shown with a 10% gelatin solution. The wet granules are screened, dried, mixed with the starch, talc and stearic acid; screened and compressed into a tablet.

TABLE II

| INGREDIENTS | AMOUNTS |
| --- | --- |
| Compound of example 1 | 20 mg |
| calcium sulfate dehydrate | 30 mg |
| Sucrose | 4 mg |
| Starch | 2 mg |
| Talc | 1 mg |
| stearic acid | 0.5 mg |

While the preferred embodiments of the invention are illustrated by the above, it is to be understood that the invention is not limited to the precise instructions herein disclosed and that the right to all modifications coming within the scope of the following claims is reserved.

BIOLOGICAL EXAMPLES

A. Enzyme Assay

HTRF In Vitro Profiling Assays for PI3K Inhibition

The PI3-Kinase profiling assays were developed to measure the compound-dependent inhibition of the alpha, beta, delta, and gamma isoforms of PI3K in an in vitro catalytic assay. This assay was developed and optimized from a kit produced by Upstate (Millipore catalog #33-017). Briefly, this procedure utilizes a pre-formed HTRF (Homogeneous Time-Resolved Fluorescence energy transfer) complex between four binding partners: 1) biotinylated PIP3, 2) GST tagged pleckstrin homology (PH) domain, 3) Europium labeled anti-GST monoclonal antibody, and 4) Streptavidin-Allophycocyanin (APC). The native PIP3 produced by PI 3-Kinase activity displaces biotin-PIP3 from the PH domain, resulting in the dissociation of the HTRF complex and a decrease in the fluorescence signal. The format of this assay is the same for all 4 isoforms of PI3K; the differences lie in the concentration of enzyme used to achieve the most robust signal. The alpha and delta assays are run at 400 pM enzyme; the beta assay is at 200 pM enzyme and the gamma assay is run at 1 nM enzyme. In addition, the alpha, beta and delta assays are run with 150 mM NaCl while the gamma assay is run in the absence of NaCl. The ATP concentration is 100 uM in the alpha, beta, and delta assays and 15 uM ATP in the gamma assay. All reactions are run at 10 uM PIP2

Assay Protocol

Compounds are serially diluted (3-fold in 100% DMSO) across a 384-well polypropylene mother plate from column 1 to column 12 and column 13 to column 24, to yield 11 concentrations for each test compound. Columns 6 and 18 contain only DMSO. Once titrations are made, 0.054 is transferred to a 384-well low-volume assay plate (Greiner 784076). This assay plate contains three pharmacological controls (known PI3K inhibitors) and 3 assay controls: (1) Enzyme without inhibitor; (2) Buffer minus enzyme, and (3) Buffer minus enzyme plus native PIP3. DMSO is stamped into all wells of columns 6 and 18. PIP3 is added at 40 μM in 1× Reaction buffer (1 μL of 200 μM PIP3) to alternating rows of column 18 (wells 18 B, D, F, H, J, L, N, P). The no-enzyme control reactions are run in wells 18 A, C, E, G, I, K, M, O (0.1 μL of 100% DMSO).

The PI3-Kinase profiling assay was optimized using the HTRF kit provided by Upstate (Millipore). The assay kit contains seven reagents: 1) 4× Reaction Buffer; 2) native PIP2 (substrate); 3) Stop A (EDTA); 4) Stop B (Biotin-PIP3); 5) Detection Mix A (Streptavidin-APC); 6) Detection Mix B (Eu-labeled Anti-GST plus GST-tagged PH-domain); 7) Detection Mix C (KF). In addition, the following items were obtained or purchased: PI3Kinase (prepared by GSK BR&AD), dithiothreitol (Sigma, D-5545), Adenosine-5'-triphosphate (ATP, Teknova cat. # A0220), native PIP3 (1,2-dioctanoyl-sn-glycero-3-[phosphoinositil-3,4,5-triphosphate]tetraammonium salt (Avanti polar lipids, 850186P), DMSO (Sigma, 472301).

PI3Kinase Reaction Buffer is prepared by diluting the stock 1:4 with de-ionized water. Freshly prepared DTT is added at a final concentration of 5 mM on the day of use. Enzyme addition and compound pre-incubation are initiated by the addition of 2.5 μL of PI3K (at twice its final concentration) in 1× reaction buffer to all wells using a Multidrop Combi. Plates are incubated at room temperature for 15 minutes. Reactions are initiated by addition of 2.5 μL of 2× substrate solution (PIP2 and ATP in 1× reaction buffer) using a Multidrop Combi. Plates are incubated at room temperature for one hour. Reactions are quenched by the addition of 2.5 μL of stop solution (Stop A and Stop B pre-mixed at a ratio of 5:1, respectively) to all wells using the Multidrop Combi. The quenched reactions are then processed to detect product formation by adding 2.5 μL of Detection Solution to all wells using the Mulitdrop Combi (Detection mix C, Detection mix A, and Detection mix B combined together in an 18:1:1 ratio, i.e.: for a 6000 μL total volume, mix 5400 μL Detection mix C, 300 μL Detection mix A, and 300 μL Detection mix B. Note: this solution should be prepared 2 hours prior to use). Following a one hour incubation in the dark, the HTRF signal is measured on the Envision plate reader set for 330 nm excitation and dual emission detection at 620 nm (Eu) and 665 nm (APC).

Data Analysis

The loss of the HTRF signal is due to the displacement of biotinylated-PIP3 from the PH domain by the PI3K-dependent conversion of PIP2 to PIP3. This loss of signal is non-linear with respect to both increasing product and time. This non-linear detection will impact accuracy of IC50 calculations; therefore, there is a need for a correction factor to obtain more accurate IC50 values This correction is derived from the assay standards in the wells of column 6 and 18 of the assay plate. All data were calculated using the ratio of acceptor (APC) to donor (Europium) fluorescence in each well of the assay plate. The percent inhibition for each compound concentration was calculated as follows: % inhibition=100*(fluorescence ratio−CtrlB)/(CtrlA−CtrlB) where CtrlA=(−) PI3Kinase reaction and CrtlB=PI3Kinase+DMSO. An $IC_{50}$ was then calculated fitting the % inhibition data to the equation: % inhibition=min+(max−min)/(1+([inhibitor]/$IC_{50}$)^n) where min is the % inhibition with no inhibitor (typically 0%), max is the signal in the (−) Enzyme control, and n is the Hill slope (typically 1). Finally, the $IC_{50}$ was converted to $pIC_{50}$ ($pIC_{50}$=−log($IC_{50}$)), and the $pIC_{50}$ value was corrected by using plate controls and the equation below: $pIC_{50}$(corrected)=$pIC_{50}$(observed)+log 10((CtrlA−CtrlB)/(CtrlB−CtrlC)), where CtrlA and CtrlB are as defined above and CrtlC=10 μM PI(3,4,5)P3, 100% displacement of biotinylated PI(3,4,5)P3.

The results are shown in Table III below.

B. Cellular Assay pAKT(Ser473) Assay in MDA-MB-468 Cells

MDA-MB-468 cells were plated in 384-well flat clear bottom tissue culture plates (Corning #3701) at a density of 5000 cells per 0.057 cm2 in 48 ul of RPMI 1640 media supplemented with 10% fetal bovine serum (FBS). Cells were seeded with a Wellmate liquid handler (Matrix). Columns 1 through 23 were plated with cells and column 24 contained media alone. Cells were incubated at 37° C. with 5% $CO_2$ for approximately 16-20 hours. Duplicate compound plates were prepared in 384-well polypropylene V-Bottom plates (Greiner #781280).

Compound titrations were made across the columns (A1-A20). 20 ul of compound was added to the first column and diluted into a 20 point curve with dimethylsulfoxide (DMSO, Thermo #TS2064) using a 2-fold dilution factor with a liquid handling robot (Hamilton). Columns 22 through 24 contained DMSO alone. Titrations were diluted 682-fold for compound treatment with 4 ul of compound added to 105 ul of RPMI media. Two ul of the diluted compound was added to the cell plates containing 48 ul of media using a multimek robot (Beckman Coulter). Final DMSO concentrations were 0.15%. Cells were treated with compound for 30 minutes at 37° C. with 5% $CO_2$.

Following incubation, media was aspirated from dosed cell plates using an ELx405 plate washer (Bio-Tek) and 25 ul of 4° C. Meso Scale Discovery (MSD) lysis buffer with the addition of protease and phosphatase inhibitors (supplied in MSD kit #N31CB-1) was added to each well using a multidrop combi (Thermo). Precoated 4-spot per well MSD ELISA plates coated with total and phospho AKT(Ser473) antibody and BSA (supplied in kit) were blocked for 1 hour at room temperature with 35 ul per well of 1× MSD wash buffer+3% BSA (supplied in kit).

Blocked plates were washed 4 times with 100 ul per well of 1× Tris wash buffer (supplied in MSD kit) using an Elx405 plate washer (Bio-Tek). To each well, 20 ul of cell lysate was added using a multimek robot (Beckman Coulter) and the plate incubated at 4° C. overnight (~12-24 hours). Following incubation, the ELISA plates were washed 4 times (100 ul/well) with 1× Tris wash buffer. Twenty microliters per well of 1× detection antibody (supplied in MSD kit) was added using a multidrop combi (Thermo), followed by a 2 hour incubation at room temperature. Detection antibody was aspirated and the plates washed 4 times (100 ul/well) with 1× Tris wash buffer. Read Buffer (supplied in MSD kit) was added at 1× (35 ul/well) at room temperature using a multidrop (Thermo). Relative luminescence units (RLU) were determined using a SECTOR™ Imager 6000 with MSD Workbench Software.

Data Analysis

Concentration Response Curves for pAKT(Ser473):

For analysis of the pAKT(Ser473) concentration response curves, the data was normalized using Phospho AKT values divided by the sum of corresponding Total AKT and Phospho AKT values. The normalized values are plotted as the percent of the DMSO-treated control values on the corresponding plate. To determine $IC_{50}$ values, the data is fit to a 4 parameter nonlinear sigmoidal dose response (variable slope) using GraphPad Prism version 4 for Windows, (GraphPad Software, San Diego Calif. USA). Criteria for curve fitting and $IC_{50}$ determination include that the $IC_{50}$ values from duplicate runs must be within 2 to 3-fold of each other, the Y min must be less than or equal to 30% of the DMSO-treated control and the Y max must range between 80-120%. Any data point equal to or greater than 40% of the curve was not utilized. The results are shown in Table III below.

TABLE III

| | Enzyme and Cell Activity | |
| --- | --- | --- |
| Ex | PI3K-b Enz Activity | Cell Activity— pAKT $IC_{50}$ in MDA-MB-468 |
| 1 | ++++ | 1-5 uM |
| 2 | +++ | 1-5 uM |
| 3 | + | >20 uM |
| 4 | +++ | 6-10 uM |
| 5 | + | >20 uM |
| 6 | ++ | ND |
| 7 | ++++ | 1-5 uM |
| 8 | +++ | 6-10 uM |
| 9 | +++ | >20 uM |
| 10 | + | ND |
| 11 | +++ | 1-5 uM |
| 12 | + | ND |
| 13 | +++ | 1-5 uM |
| 14 | +++ | 1-5 uM |
| 15 | +++ | >20 uM |
| 16 | ++ | >20 uM |
| 17 | ++ | <1 uM |
| 18 | + | ND |
| 19 | ++ | >20 uM |
| 20 | ++ | <1 uM |
| 21 | + | >20 uM |
| 22 | ++++ | 1-5 uM |
| 23 | ++++ | <1 uM |
| 24 | +++ | <1 uM |
| 25 | +++ | <1 uM |
| 26 | +++ | 1-5 uM |
| 27 | ++ | <1 uM |
| 28 | + | ND |
| 29 | +++ | 1-5 uM |
| 30 | ++++ | 6-10 uM |
| 31 | ++++ | >20 uM |

TABLE III-continued

Enzyme and Cell Activity

| Ex | PI3K-b Enz Activity | Cell Activity—pAKT IC$_{50}$ in MDA-MB-468 |
|---|---|---|
| 32 | +++ | 11-20 uM |
| 33 | + | >20 uM |
| 34 | + | ND |
| 35 | +++ | 11-20 uM |
| 36 | +++ | 1-5 uM |
| 37 | ++ | 1-5 uM |
| 38 | ++ | <1 uM |
| 39 | ++ | >20 uM |
| 40 | +++ | <1 uM |
| 41 | +++ | 6-10 uM |
| 42 | +++ | <1 uM |
| 43 | +++ | <1 uM |
| 44 | + | ND |
| 45 | + | >20 uM |
| 46 | ++ | 1-5 uM |
| 47 | ++ | 1-5 uM |
| 48 | + | >20 uM |
| 49 | + | ND |
| 50 | ++ | 6-10 uM |
| 51 | + | ND |

PI3K-beta Enzyme pIC$_{50}$ Range Key

| | |
|---|---|
| 9.9-9.0 | ++++ |
| 8.9-8.0 | +++ |
| 7.9-7.0 | ++ |
| 6.9-5.9 | + |

What is claimed is:

1. A compound of formula (I):

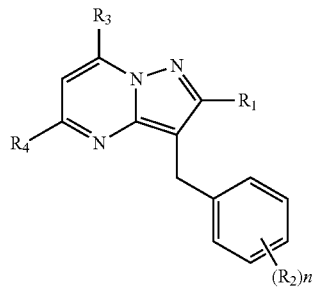

(I)

wherein

R1 is H, C$_{1-6}$alkyl, —OH, C$_{1-6}$alkoxy, NH$_2$, or CF$_3$;

each R2 is selected independently from C$_{1-6}$alkyl, halo, CF$_3$, and the R2s are located ortho and meta on the phenyl group;

R3 is H, —CN, OH, NH$_2$, halo, C$_{1-6}$alkyl, C$_{1-6}$alkoxy, —C(O)Ra, —NH(O)Ra, =O, or a 5 or 6 membered heterocycle containing 1-3 heteroatoms selected from N and O;

R4 is a 5 or 6 membered heterocycle or 5 or 6 membered heteroaryl containing 1-3 heteroatoms selected from N and O, optionally substituted with C$_{1-6}$alkyl or =O;

Ra is OH, NH$_2$, or C$_{1-6}$alkyl; and n is 2, or a pharmaceutically acceptable salt thereof.

2. A compound of Formula (Ia):

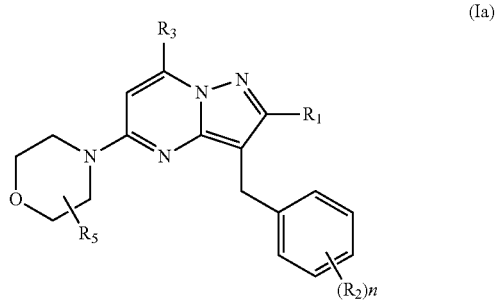

(Ia)

wherein

R1 is H, C$_{1-6}$alkyl, —OH, C$_{1-6}$alkoxy, NH$_2$, or CF$_3$;

each R2 is H, C$_{1-6}$alkyl, halo, CF$_3$, or two R2's combine with the phenyl ring to which they are attached to form napthyl;

R3 is H, —CN, OH, NH$_2$, halo, C$_{1-6}$alkyl, C$_{1-6}$alkoxy, —C(O)Ra, —NH(O)Ra, =O, or a 5 or 6 membered heterocycle containing 1-3 heteroatoms selected from N and O;

R5 is H, C$_{1-6}$alkyl or =O;

Ra is OH, NH$_2$, or C$_{1-6}$alkyl; and n is 0-2, or a pharmaceutically acceptable salt thereof.

* * * * *